(12) United States Patent
Zhang et al.

(10) Patent No.: US 12,358,911 B2
(45) Date of Patent: Jul. 15, 2025

(54) HETEROCYCLIC COMIPOUND AS CDK-HDAC DUAL PATHWAY INHIBITOR

(71) Applicant: Hangzhou Innogate Pharma Co., Ltd., Zhejiang (CN)

(72) Inventors: Hancheng Zhang, Zhejiang (CN); Xiangyang Ye, Zhejiang (CN); Xin Cheng, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 1074 days.

(21) Appl. No.: 17/311,627

(22) PCT Filed: Dec. 9, 2019

(86) PCT No.: PCT/CN2019/124143
§ 371 (c)(1),
(2) Date: Jun. 7, 2021

(87) PCT Pub. No.: WO2020/114519
PCT Pub. Date: Nov. 6, 2020

(65) Prior Publication Data
US 2022/0024916 A1 Jan. 27, 2022

(30) Foreign Application Priority Data
Dec. 7, 2018 (CN) .......... 201811497798.X

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC ..... C07D 471/04; C07D 519/00; A61P 35/00; A61P 35/02; A61K 31/519
See application file for complete search history.

(56) References Cited

FOREIGN PATENT DOCUMENTS

| CN | 1422268 | A | | 6/2003 | |
|---|---|---|---|---|---|
| CN | 101001857 | A | | 7/2007 | |
| CN | 105294681 | A | | 2/2016 | |
| CN | 106831780 | A | | 6/2017 | |
| CN | 108699055 | A | * | 10/2018 | ............. A61P 35/02 |
| WO | 2014150925 | A2 | | 9/2014 | |
| WO | WO-2017101763 | A1 | * | 6/2017 | ............. A61P 35/02 |

OTHER PUBLICATIONS

International Search Report issued Mar. 6, 2020 in PCT/CN2019/124143.

* cited by examiner

*Primary Examiner* — Joseph K McKane
*Assistant Examiner* — Meghan C Heasley
(74) *Attorney, Agent, or Firm* — Ice Miller LLP

(57) ABSTRACT

The invention provides compounds of formula (I) as shown below, as well as pharmaceutically acceptable salts, hydrates or solvates thereof. The invention also provides pharmaceutical compositions of these compounds, methods for their preparation, and their use in the treatment of diseases and disorders (including cancers).

(I)

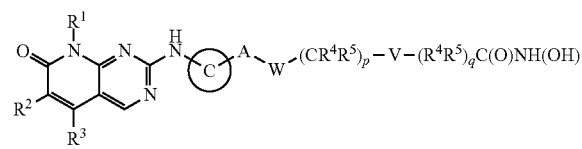

4 Claims, No Drawings

HETEROCYCLIC COMPOUND AS CDK-HDAC DUAL PATHWAY INHIBITOR

CROSS-REFERENCE TO RELATED APPLICATION

This application is a Section 371 of International Application No. PCT/CN2019/124143 filed Dec. 9, 2019, which was published in the Chinese language Jun. 11, 2020, under International Publication No. WO 2020/114519 A1, which claims priority to Chinese Patent Application Number 201811497798.X filed Dec. 7, 2018, the disclosures of which are incorporated herein by reference in their entireties.

BACKGROUND OF THE INVENTION

Cyclin-dependent kinases (CDKs) are protein kinases involved in important cellular processes, such as cell cycle or transcription regulation. There are 13 CDKs and different CDKs are responsible for the activation of the cell cycle of quiescent cells, as well as for the progression of the cell cycle from G1 to mitosis. Each of the CDKs controls a specific checkpoint of the cell cycle. CDKs are activated by the binding to the cyclins and thus form specific complexes. In many human cancers, CDKs are overactive or CDK-inhibiting proteins are not functional. Therefore, it is rational to target CDK function to prevent unregulated proliferation of cancer cells. For example, CDK4 is the key regulator of the G1-S transition. In complex with Cyclin D, CDK4 phosphorylates Rb and drives cell cycle progression, a process inhibited by p16. The p16-CDK4-cyclin D-Rb is aberrant in the majority of cancers and thus is an attractive target for anti-cancer therapy.

At present, the US FDA has approved two CDK4/6 selective inhibitors Palbociclib (Pfizer) and Ribocicilib (Novatis) for the first line treatment of HR+/HER2− advanced breast cancer. Besides strong inhibition against CDK4 and CDK6, Abemaciclib developed by Lilly also inhibits other CDKs such as CDK2. In September 2017, FDA approved Abemaciclib for the treatment of some breast cancers in the United States. There are many cell cycling modulators entering into clinical studies now.

Histone deacetylases (HDACs) are a class of enzymes that remove the acetyl group from the ε-amino groups of lysine residues located in the $NH_2$ terminal tails of core histones. There are 18 known human histone deacetylases, grouped into four classes based on the structure of their accessory domains. Class I includes HDAC1, HDAC2, HDAC3 and HDAC8, and have homology to yeast RPD3. HDAC4, HDAC5, HDAC7 and HDAC9 belong to class II, and have homology to yeast HDA1. HDAC6 and HDAC10 contain two catalytic sites and are classified as class IIa, whereas HDAC11 has conserved residues in its catalytic center that are shared by both class I and class II deacetylases and it is sometimes placed in class IV. Histone deacetylase inhibitors (HDACIs) are emerging as a new class of potential anticancer agents and have been shown to induce differentiation, cell-cycle arrest and apoptosis, and to inhibit migration, invasion and angiogenesis in many cancer cell lines. In addition, HDAC inhibitors inhibit tumor growth in animal models and show antitumor activity in patients. There is also growing evidence that HDAC inhibitors have potential therapeutic application in nonmalignant diseases, such as for treatment of inflammatory and neurodegenerative diseases.

Study has shown that pan-HDAC inhibitor could effectively induce cell cycle arrest in G1 phase in many lung cancer cell lines, thus inhibiting cell proliferation. This inhibitor significantly reduced the protein levels of Cyclin D1, CDK2 and CDK4 in cells, and upregulated the expression of P21WAF1/CIP1 and cyclin E. Further experiments proved this inhibitor suppresses the activity of HDAC6 through down regulating its expression. Pan-HDAC inhibitor induced super acetylation of HSP90 in lung cancer cells, thus increasing the cellular degradation of Cyclin D1 and CDK4.

Another study demonstrates that Retinoblastoma (Rb) could form nucleosome remodeling complex with HDAC and hSWI/SNF, inhibit the transcription of Cyclin E and Cyclin A, and induce cell cycle arrest in G1 phase. Rb phosphorylation catalyzed by Cyclin D1/CDK4 prevents it from interacting with HDAC, leading to the release of Cyclin E expression repression and G1 cell cycle arrest. Renier Heijkants et al. reported that combined inhibition of CDK and HDAC is a promising therapeutic strategy for the treatment of cutaneous and uveal metastatic melanoma.

In summary, small molecule CDK inhibitors (which inhibit one or more subtypes of CDKs) can be used to treat many different cancers. In particular, a single small molecule designed to inhibit CDK and HDAC at the same time may have a synergetic effect in the treatment of cancer.

On the other hand, study has reported that CDK inhibitors can also be used in combination with other targeted anti-cancer drugs or antibodies, which have synergetic effects on cancer treatment. The CDK-HDAC dual-pathway inhibitor of the present invention can also be used in combination with other targeted antitumor drugs or antibodies, and such a combination treatment scheme of two drugs provides the possibility of acting on three targets at the same time, thus reducing the clinical complexity and technical problems of simple single drug combination (i.e., combination of three drugs: CDK inhibitor+HDAC inhibitor+targeted antitumor drugs or antibodies). In addition, the combination of CDK-HDAC dual pathway inhibitor and other targeted antitumor drugs (or antibodies) can delay the generation of drug resistance and increase the anti-tumor effect, which has certain advantages in the treatment of various cancers.

CDK and HDAC dual pathway inhibitors have been reported in the literature.

But up to now, there is still a need to develop more dual-pathway inhibitors of CDK and HDAC in this field.

SUMMARY OF THE INVENTION

The present invention provides novel heterocyclic compounds and their uses, for example as inhibitors of protein kinase (such as CDKs) and HDACs. In particular, the present invention relates to the skills of medicinal chemistry design, wherein different pharmacophores are fused to a single small molecule, and the compounds simultaneously inhibiting different subtypes of CDK and different subtypes of HDAC were designed and synthesized.

The present invention provides a compound of formula (I), its diastereomers or enantiomers, when possible, comprise its deuterated derivatives, and/or its corresponding pharmaceutically acceptable salts, prodrugs, hydrates, and solvate thereof.

In the first aspect of the present invention, a compound of the following formula (I), or the deuterated derivative at any possible position in the molecule, diastereomers and enantiomers (possible any) thereof:

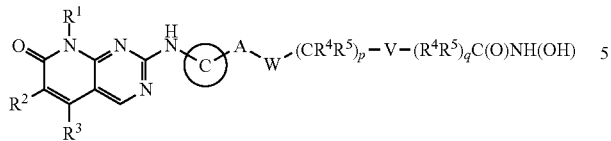

(I)

or the pharmaceutically acceptable salts, prodrugs, hydrates, solvates thereof is provided,
wherein $C$ is phenyl ring, 5- to 6-membered monocyclic heteroaromatic ring, or 8- to 10-membered fused heteroaromatic ring (including aromatic-aromatic fused ring, aromatic-(saturated or unsaturated alkane rings or heterocyclic ring) fused ring), the mono-heteroaromatic ring and bicyclic heteroaromatic ring described herein may optionally comprise 1 to 5 heteroatoms independently selected from N, O, and S;

A is a bond, —O—, —C(O)—, —(CR$^6$R$^7$)$_m$—, —N(R$^8$)—, C$_{2-8}$ alkenylene, C$_{3-8}$ cycloalkane structure, 3 to 9-membered heterocyclic ring (optionally containing 1-3 heteroatoms selected from N, O, or S), aromatic ring, or heteroaromatic ring; the cycloalkane structure, heterocyclic ring, aromatic ring, and heteroaromatic ring can be optionally and independently substituted by 0-4 substituents selected from the group consisting of hydroxy, halogen, C$_{1-4}$ alkyl, C$_{1-4}$ haloalkyl, cyano, provided that the chemical structure formed being stable and meaningful. When two hydroxyl groups are simultaneously connected to the same carbon atom of the cycloalkane structure or heterocycle, it means that the two hydroxyl groups and the carbon atom form a carbon group (ie, —C(O)—) structure; preferably, A is selected from the group consisting of: —N(R$^8$)—, —O—, and bicyclic 3- to 9-membered heterocycle (optionally containing 1-3 heteroatoms selected from N, O, S) structure;

W is bond, —C(O)—, —(CR$^6$R$^7$)$_m$—, —(CR$^6$R$^7$)$_m$NR$^8$—, —N(R$^8$)—, —OC(O)—, —C(O)O—, —C(O)NH—, —NHC(O)—, —S(O)$_2$—, —S(O)$_2$NH—, —NHS(O)$_2$—, C$_{3-8}$ cycloalkane structure, 3 to 9-membered heterocycle (optionally containing 1-3 heteroatoms selected from N, O or S), aromatic ring, or heteroaromatic ring; with the proviso that $C$, W, V, R$^4$, R$^5$, p and q together form a stable chemical structure; when A and W are both bond, (CR$^4$R$^5$)$_p$—V—(CR$^4$R$^5$)$_q$C(O)NH(OH) is directly connected to $C$;

R$^1$ is independently hydrogen, C$_{1-8}$ alkyl, C$_{2-8}$ alkenyl, C$_{2-8}$ alkynyl, C$_{3-8}$ cycloalkyl, 3- to 9-membered heterocyclic group (optionally containing 1-3 heteroatoms selected from N, O or S), aryl, or heteroaryl;

R$^2$ is hydrogen, deuterium, halogen, C$_{1-8}$ alkyl, C$_{2-8}$ alkenyl, C$_{2-8}$ alkynyl, C$_{3-8}$ cycloalkyl, 3- to 9-membered heterocyclic group (optionally containing 1-3 heteroatoms selected from N, O or S), aryl, heteroaryl, CN, NO$_2$, (CR$^4$R$^5$)$_m$OR$^{12}$, (CR$^4$R$^5$)$_m$SR$^{12}$, (CR$^4$R$^5$)$_m$N(R$^{13}$)$_2$, (CR$^4$R$^5$)$_m$C(O)R$^9$, (CR$^4$R$^5$)$_m$C(O)OR$^{12}$, (CR$^4$R$^5$)$_m$C(O)N(R$^{13}$)$_2$, (CR$^4$R$^5$)$_m$OC(O)R$^9$, (CR$^4$R$^5$)$_m$OC(O)OR$^{12}$, (CR$^4$R$^5$)$_m$OC(O)N(R$^{13}$)$_2$, (CR$^4$R$^5$)$_m$NR$^8$C(O)R$^9$, (CR$^4$R$^5$)$_m$NR$^{13}$C(O)OR$^{12}$, (CR$^4$R$^5$)$_m$NR$^{13}$C(O)N(R$^{13}$)$_2$, (CR$^4$R$^5$)$_m$S(O)R$^9$, and (CR$^4$R$^5$)$_m$S(O)$_2$R$^9$;

R$^3$ is hydrogen, deuterium, halogen, C$_{1-8}$ alkyl, C$_{2-8}$ alkenyl, C$_{2-8}$ alkynyl, C$_{3-8}$ cycloalkyl, 3- to 9-membered heterocyclic group (optionally containing 1-3 heteroatoms selected from N, O or S), aryl, heteroaryl, OR$^6$, NR$^6$R$^7$, or CN;

each R$^4$ and R$^5$ is independently hydrogen, deuterium, halogen, or C$_{1-4}$ alkyl;

or R$^4$ and R$^5$ together with the carbon atom they attached to form a 3- to 9-membered cyclic structure which optionally containing 0-3 additional heteroatoms selected from N, O or S); or R$^4$ and R$^5$ together with the carbon atom they attached to form carbonyl (i.e., CR$^4$R$^5$ is C(O));

each of R$^6$ and R$^7$ is independently hydrogen, deuterium, halogen, C$_{1-4}$ alkyl, C$_2$-4 alkenyl, C$_{2-4}$ alkynyl, C$_{3-8}$ cycloalkyl, 3- to 9-membered heterocyclic (optionally containing 1-3 heteroatoms selected from N, O or S), aryl, or heteroaryl;

or R$^6$ and R$^7$ together with the carbon atom they attached form a 3- to 9-membered cyclic structure which optionally containing 0-3 additional heteroatoms each independently selected from N, O or S;

R$^8$ is hydrogen, C$_{1-4}$ alkyl, R$^9$C(O)—, R$^9$S(O)$_2$—, C$_{3-8}$ cycloalkyl, 3- to 9-membered heterocyclic group (optionally containing 1-3 heteroatoms selected from N, O or S), aryl, or heteroaryl; wherein R$^9$ is hydrogen, C$_{1-4}$ alkyl, C$_{2-4}$ alkenyl, C$_{2-4}$ alkynyl, C$_{3-8}$ cycloalkyl, 3- to 9-membered heterocyclic group (optionally containing 1-3 heteroatoms selected from N, O or S), aryl, or heteroaryl;

V is —CR$^{10}$R$^{11}$—, —CH═CH—, —C≡C—, —O—, —S—, —N(R$^8$)—, —C(O)—, —OC(O)—, —C(O)O—, —OC(O)O—, —C(O)NH—, —NHC(O)—, —NHC(O)NH—, —S(O)—, —S(O)$_2$—, —S(O)$_2$NH—, —NHS(O)$_2$—, C$_{3-8}$ cycloalkyl, 3- to 9-membered heterocyclic group (optionally containing 1-3 heteroatoms selected from N, O or S), aryl, heteroaryl, or —V$^1$(CR$^4$R$^5$)$_t$V$^2$—;

wherein R$^{10}$ and R$^{11}$ are each independently hydrogen, deuterium, halogen, C$_{1-4}$ alkyl, C$_{2-4}$ alkenyl, C$_{2-4}$ alkynyl, C$_{3-8}$ cycloalkyl, 3- to 9-membered heterocyclic group (optionally containing 1-3 heteroatoms selected from N, O or S), aryl, heteroaryl, —CN, —OR$^{12}$, —SR$^{12}$, —N(R$^{13}$)$_2$, —C(O)R$^9$, —C(O)OR$^{12}$, —C(O)N(R$^{13}$)$_2$, —OC(O)R$^9$, —NR$^{13}$C(O)R$^9$, or —S(O)$_2$R$^9$; or R$^{10}$ and R$^{11}$ together with the carbon atom they attached to form a 3- to 9-membered cyclic which optionally containing 0-3 additional heteroatoms selected from N, O or S); wherein R$^{12}$ is hydrogen, C$_{1-4}$ alkyl, C$_{3-8}$ cycloalkyl, 3- to 9-membered heterocyclic group (optionally containing 1-3 heteroatoms selected from N, O or S), aryl, or heteroaryl; each R$^{13}$ is hydrogen, C$_{1-4}$ alkyl, C$_{3-8}$ cycloalkyl, 3- to 9-membered heterocyclic group (optionally containing 1-3 heteroatoms selected from N, O or S), aryl, or heteroaryl; or two $R^{13}$ together with the nitrogen atom they attached to form a 3- to 9-membered cyclic structure which optionally containing 0-3 additional heteroatoms selected from N, O, or S;

$V^1$ and $V^2$ are each independently bond, —$CR^{10}R^{11}$—, —CH=CH—, —C≡C—, —O—, —S—, —N($R^8$)—, —C(O)NH—, —NHC(O)—, —S(O)$_2$—, —S(O)$_2$NH—, —NHS(O)$_2$—, $C_{3-8}$ cycloalkyl structure, 3- to 9-membered heterocyclic group (optionally containing 1-3 heteroatoms selected from N, O or S), aryl, or heteroaryl;

p and q are each independently 0, 1, 2, 3, 4, 5, 6, 7, 8, 9, or 10;

m is 0, 1, 2, 3, or 4;

t is 0, 1, 2, 3, 4, or 5;

with the proviso that the group formed by V, $V^1$, $V^2$, p, q and t is chemically stable structure;

wherein each of the above mentioned alkyl, alkenyl, alkynyl, cycloalkyl, heterocyclic group, aryl, heteroaryl, cycloalkane structure, heterocyclic, aromatic cyclic and heteroaryl cyclic are optionally and each independently substituted by 1-3 substituents selected from the group consisting of deuterium, halogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O or S), aryl, heteroaryl, —CN, —NO$_2$, —OR$^{12}$, —SR$^{12}$, —N(R$^{13}$)$_2$, —C(O)R$^9$, —C(O)OR$^{12}$, —C(O)N(R$^{13}$)$_2$, —SO$_2$N(R$^{13}$)$_2$; for the substituents, the definition of each group is as described above.

unless otherwise specified, the above aryl group is aryl group having 6 to 12 carbon atoms; the heteroaryl group and heteroaryl cyclic is 5- to 15-membered heteroaryl group comprising hetero atom.

with the proviso that the compounds described in this patent are other than these structures:

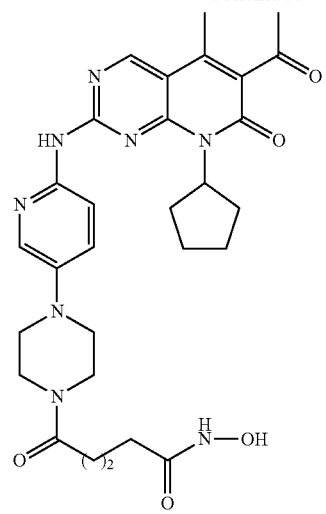

-continued

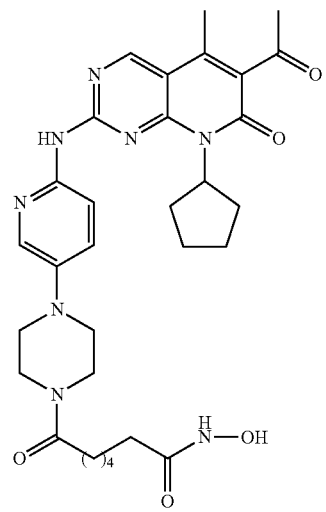

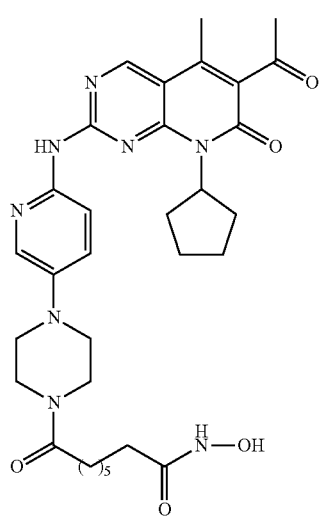

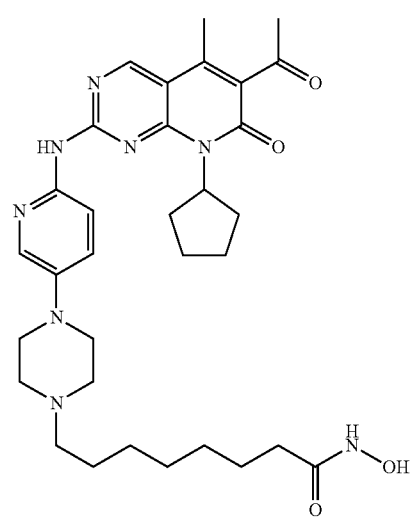

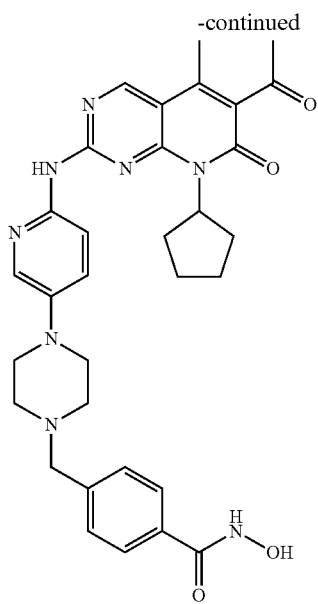
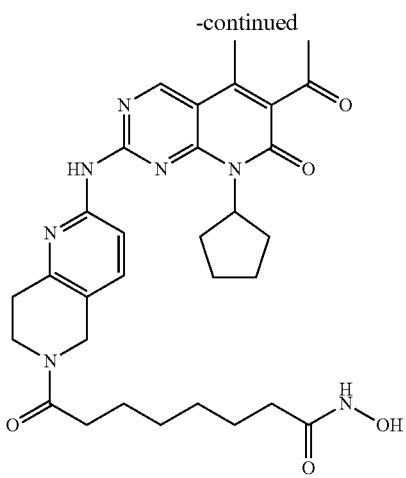
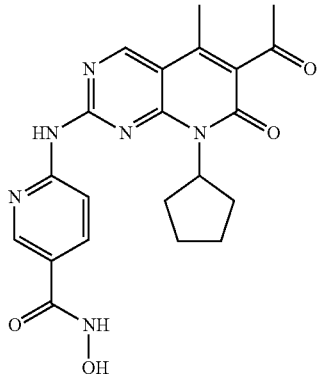
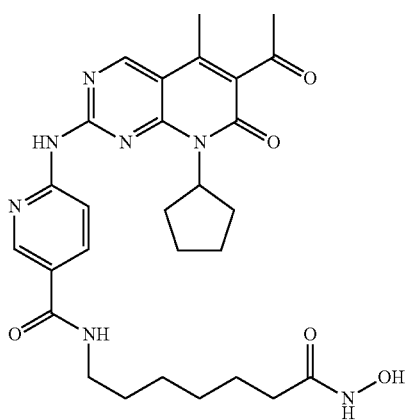
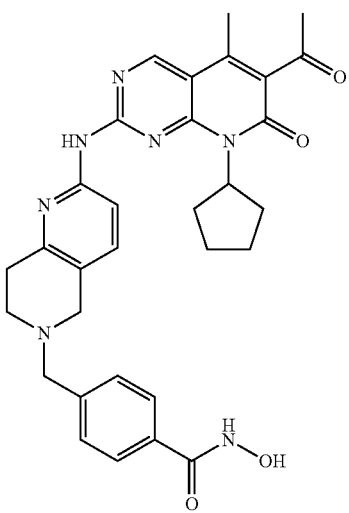

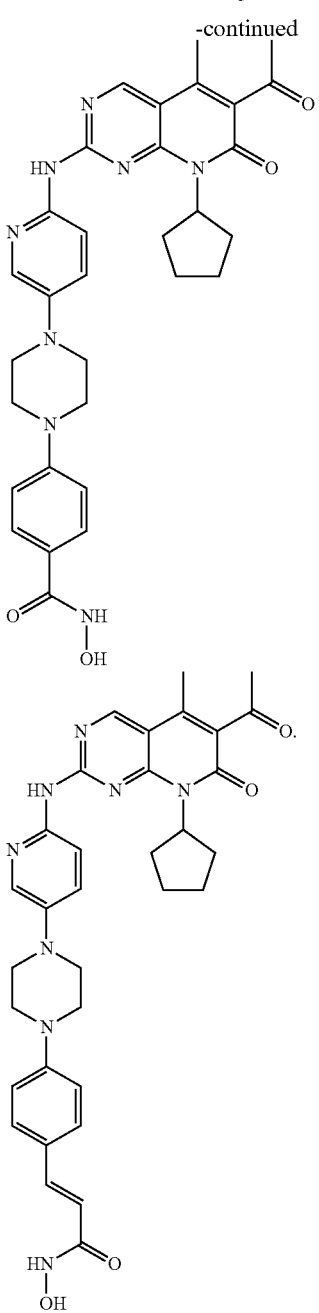

In another preferred embodiment,
A is —O—, —N(R⁸)—, 3- to 9-membered heterocyclic group (optionally containing 1-3 heteroatoms selected from N, O, or S), $C_{2-8}$ alkenyl; preferably, A is selected from —O—, —N(R⁸)—.

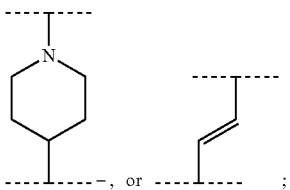

W is bond, —(CR⁶R⁷)$_m$—, —(CR⁶R⁷)$_m$NR⁸—, or —N(R⁸)—, with the proviso that

,

A, W, V, R⁴, R⁵, p, and q together form a stable chemical structure.
In another preferred embodiment,

is phenyl ring, 5- to 6-membered monocyclic heteroaromatic ring, wherein the mono-heteroaromatic ring described herein may optionally comprise 1 to 4 heteroatoms independently selected from N, O and S;
A is —O—, —N(R⁸)—, $C_{2-8}$ alkenyl, 3- to 9-membered heterocyclic group (optionally containing 1-3 heteroatoms selected from N, O or S); preferably, A is selected from —O—, —N(R₈)—,

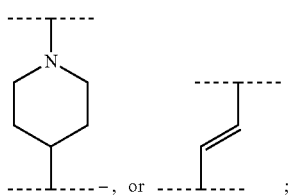

W is bond, —(CR⁶R⁷)$_m$—, —(CR⁶R⁷)$_m$NR⁸—, or —N(R⁸)—, with the proviso that

,

A, W, V, R⁴, R⁵, p and q together form a stable chemical structure;
R¹ is independently hydrogen, $C_{1-8}$ alkyl, $C_{3-8}$ cycloalkyl, 3- to 9-membered heterocyclic group (optionally containing 1-3 heteroatoms selected from N, O or S);
R² is hydrogen, deuterium, halogen, $C_{1-8}$ alkyl, $C_{2-8}$ alkenyl, $C_{2-8}$ alkynyl, $C_{3-8}$ cycloalkyl, 3- to 9-membered heterocyclic group (optionally containing 1-3 heteroatoms selected from N, O or S), (CR⁴R⁵)$_m$C(O)R⁹;
R³ is hydrogen, deuterium, halogen, $C_{1-8}$ alkyl, $C_{3-8}$ cycloalkyl;
each R⁴ and R⁵ is independently hydrogen, halogen, or $C_{1-4}$ alkyl;
each R⁶ and R⁷ is independently hydrogen, halogen, $C_{1-4}$ alkyl;
R⁸ is hydrogen, $C_{1-4}$ alkyl, R⁹C(O)—, R⁹S(O)₂—, $C_{3-8}$ cycloalkyl, 3- to 9-membered heterocyclic group (optionally containing 1-3 heteroatoms selected from N, O or S), aryl, or heteroaryl; wherein R⁹ is hydrogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O or S), aryl, or heteroaryl;

V is —V¹(CR⁴R⁵)ₜV²—; V¹ and V² are each independently —CR¹⁰R¹¹—, —CH=CH—, C≡C, —O—, —S—, —N(R⁸)—, —C₃₋₈ cycloalkane structure, 3- to 9-membered heterocyclic group (optionally containing 1-3 heteroatoms selected from N, O or S), aryl, or heteroaryl; wherein R¹⁰ and R¹¹ are each independently hydrogen, halogen, or C₁₋₄ alkyl;
p and q are each independently 0, 1, 2, 3, 4, 5 or 6;
m is 0, 1, 2;
t is 0, 1, 2, 3;
with the proviso that the group formed by V, V¹, V², p, q and t is chemically stable structure;

In another preferred embodiment,

is a benzene ring or a pyridine ring. while the remaining groups are defined as above.

In another preferred embodiment, the groups are as defined as following: R¹ is cyclopentyl; R² is CH₃C(O)—; R³ is methyl; and other groups are as described above.

In another preferred embodiment, A is —O— or —N(R⁸)—.

In another preferred embodiment, W is bond, (CR⁶R⁷)ₘ—, or —(CR⁶R⁷)ₘNR⁸—.

In another preferred embodiment, R⁴ and R⁵ are each independently hydrogen or C₁₋₄ alkyl; p and q are each independently 0, 1, 2, 3, 4, 5 or 6.

In another preferred embodiment, V is preferrably selected from the group consisting of bond, —CH₂—, —CH=CH—, —C≡C—, —O—, —S—, —N(R⁸)—, 3- to 9-membered heterocyclic ring (optionally containing 1-3 heteroatoms selected from N, O or S), aryl, heteroaryl, or —V¹(CR⁴R⁵)ₜV²—;

In another preferred embodiment, V is V¹(CH₂)ₜV²—; V¹ and V² are each independently bond, —CH₂—, —CH=CH—, —C≡C—, —O—, —N(R⁸)—, aryl, or heteroaryl; preferably, V¹ and V² are each independently —CH=CH—, —C≡C—, —O—, —N(R⁸)—, aryl, or heteroaryl; t is 0, 1, 2 or 3.

In another preferred embodiment, the combination of A, W and (CR⁴R⁵)ₚ—V—(CR⁴R⁵)qC(O)NH(OH) is of the following structure:
-A-(CH₂)ₚ—V¹—V²—(CH₂)q—C(O)NH(OH); wherein A is —O— or —N(R⁸)—; V¹ is —N(R⁸)— or —O—; V² is aryl or heteroaryl; p is 2, 3 or 4; q is 0, 1, 2, 3 or 4.

In another preferred embodiment, the combination of A, W and (CR⁴R⁵)ₚ—V—(CR⁴R⁵)qC(O)NH(OH) is of the following structure:
-A-(CH₂)ₚ—V¹—V²—(CH₂)q—C(O)NH(OH); wherein A is —O— or —N(R⁸)—; V¹ is aryl or heteroaryl; V² is —CH₂—, —CH=CH— or —C≡C—; p and q are each independently 0, 1, 2, 3 or 4.

In another preferred embodiment, the combination of W and A

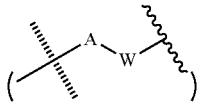

is selected from the following group:

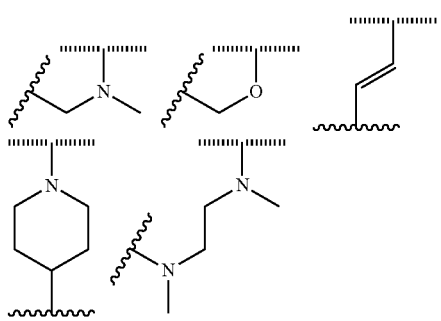

wherein ⌇ is the connecting point to (CR⁴R⁵)ₚ—V—(CR⁴R⁵)qC(O)NH(OH), ⌇ is the connecting point to

.

In another preferred embodiment, the combination of A, W and (CR⁴R⁵)ₚ—V—(CR⁴R⁵)qC(O)NH(OH), i.e,

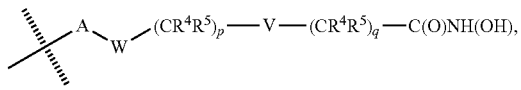

is selected from the following group:

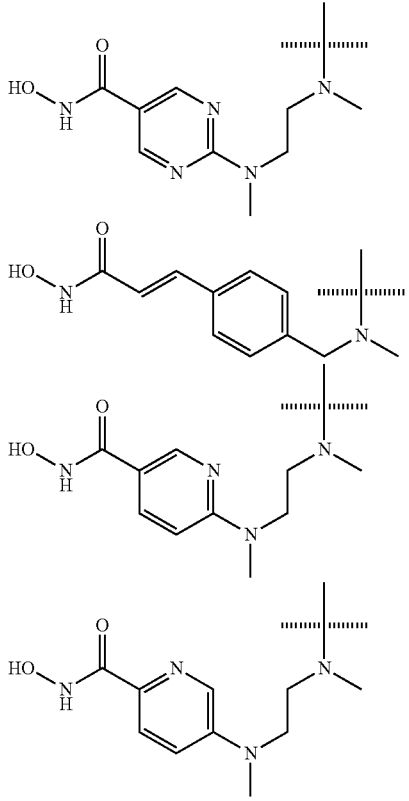

-continued
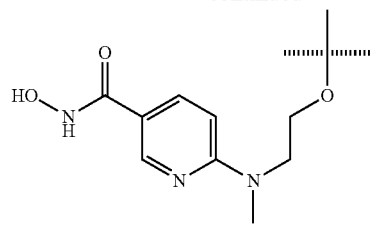
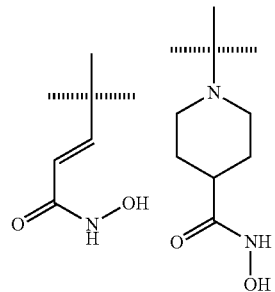
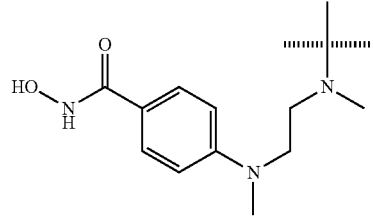
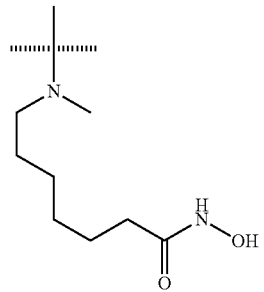
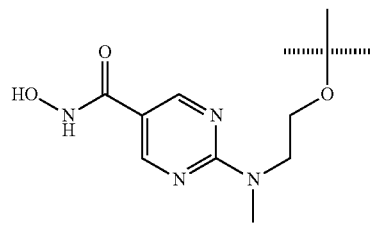
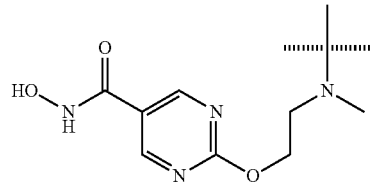
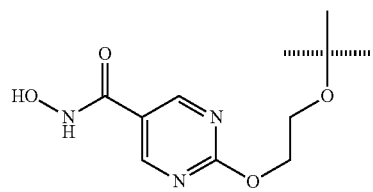
-continued
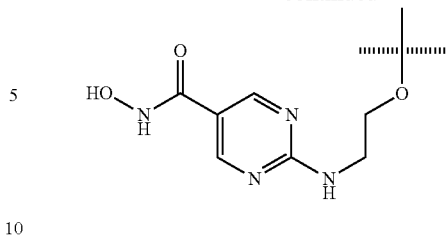
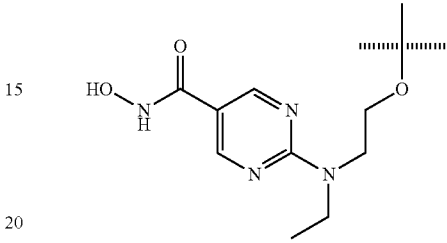
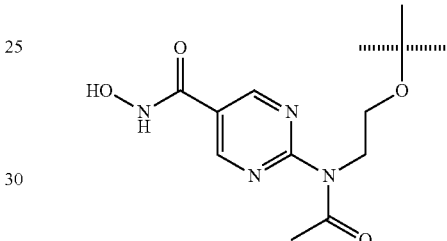
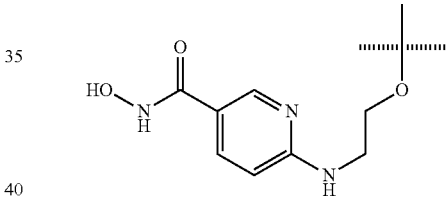
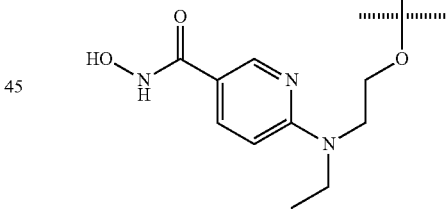
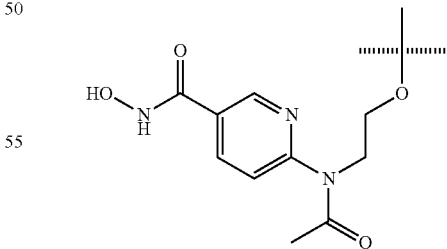
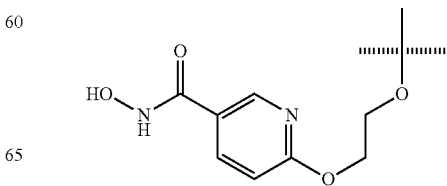

-continued
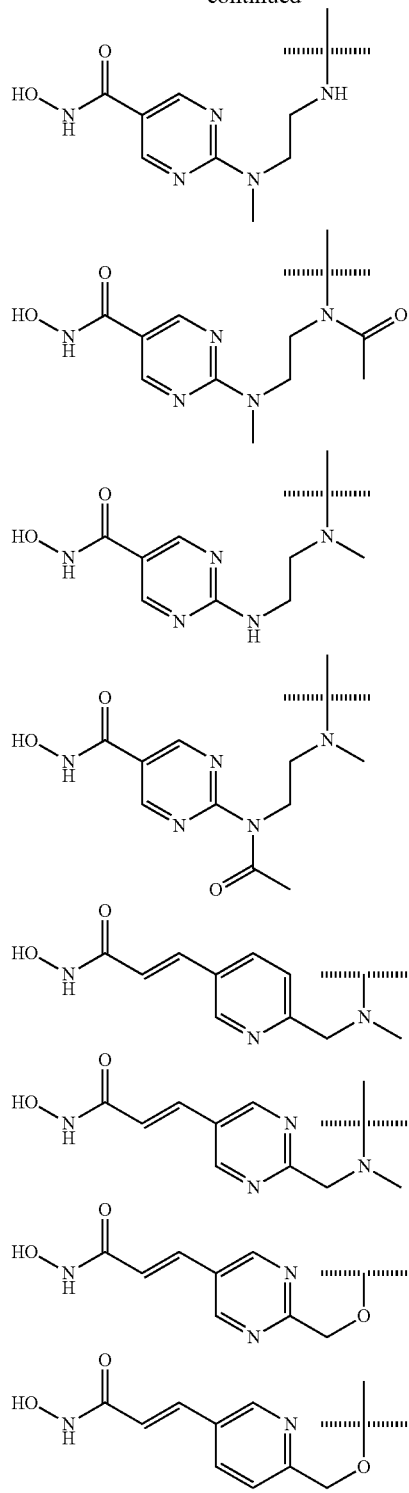
wherein  is the connecting point to C.
In another preferred embodiment, the compounds of formula (I) are:
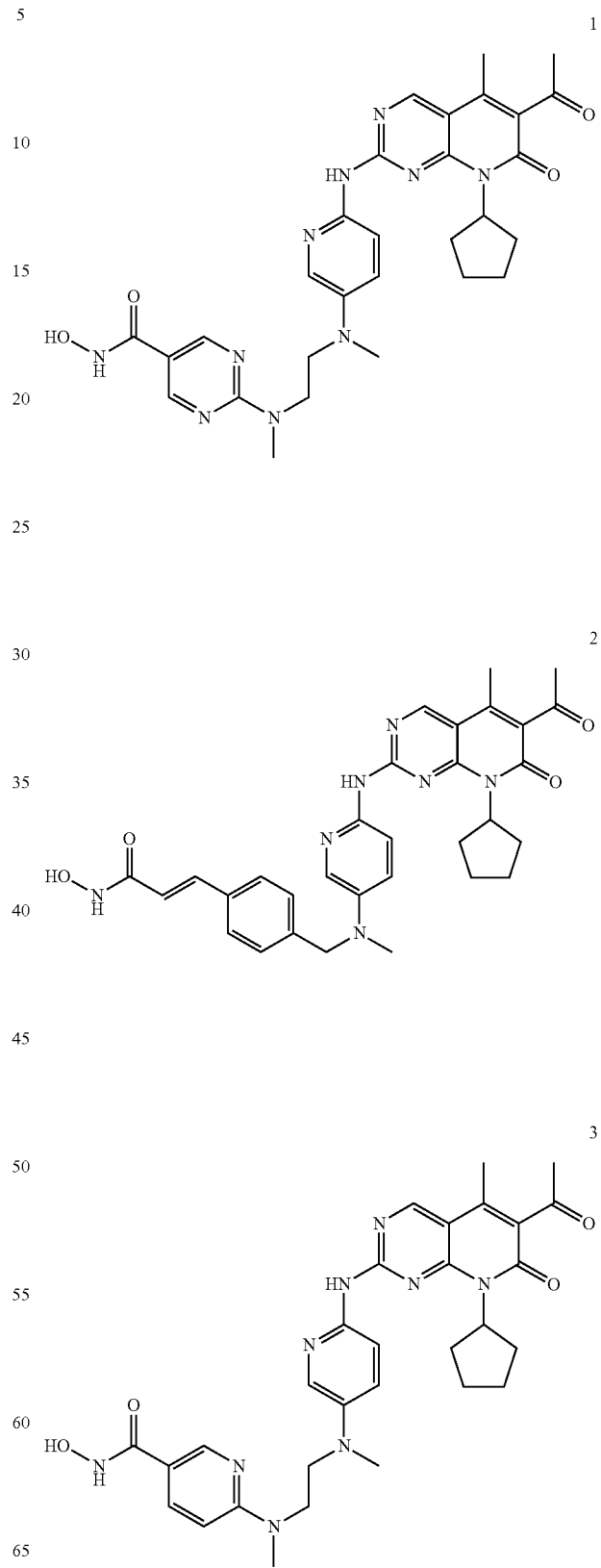

-continued
4
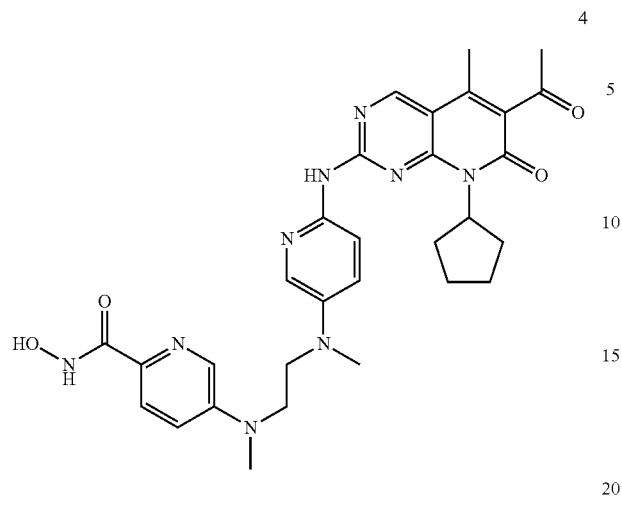
5
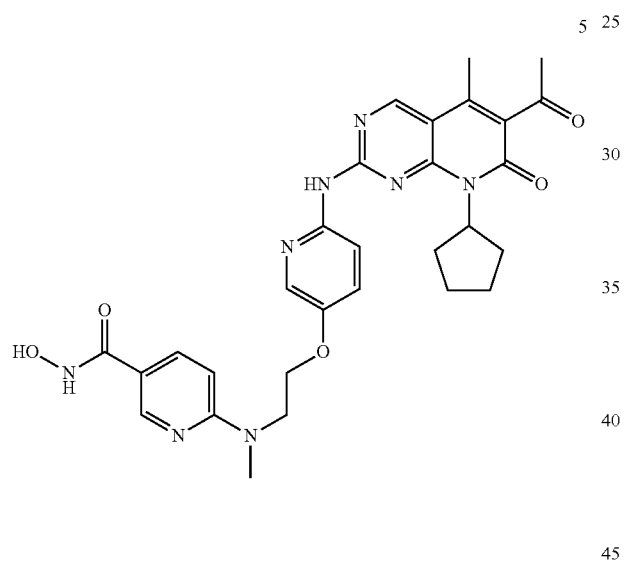
6
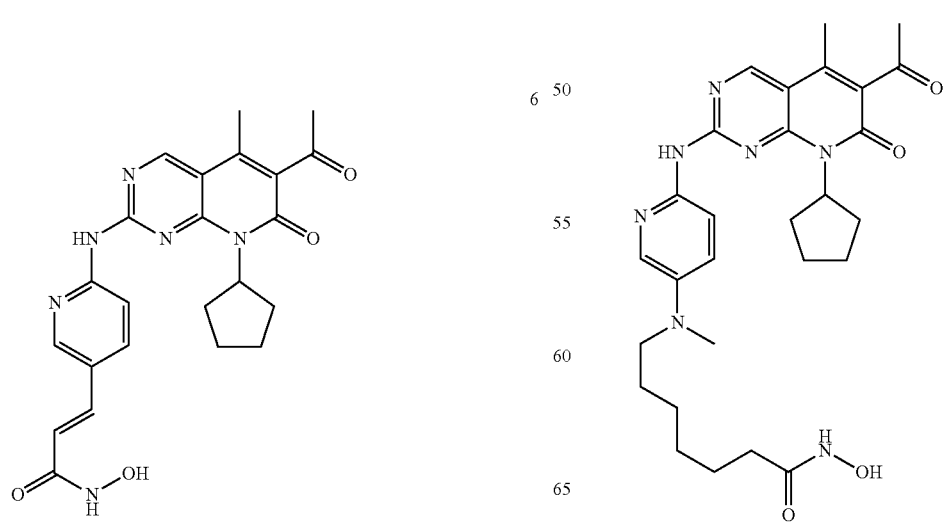
-continued
7
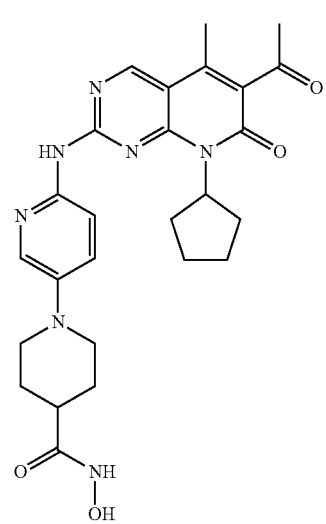
8
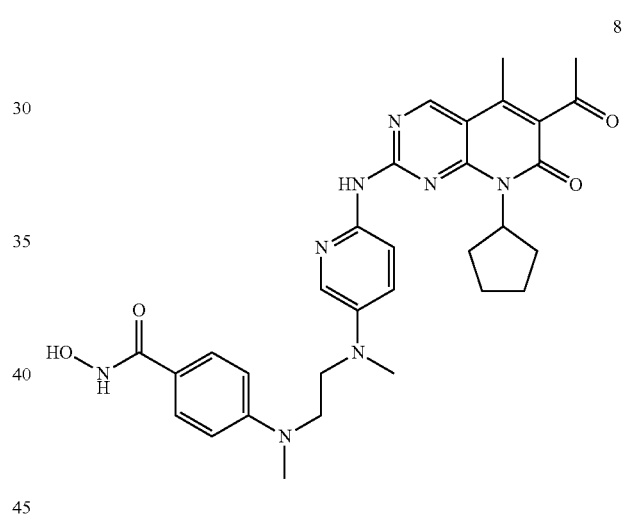
9

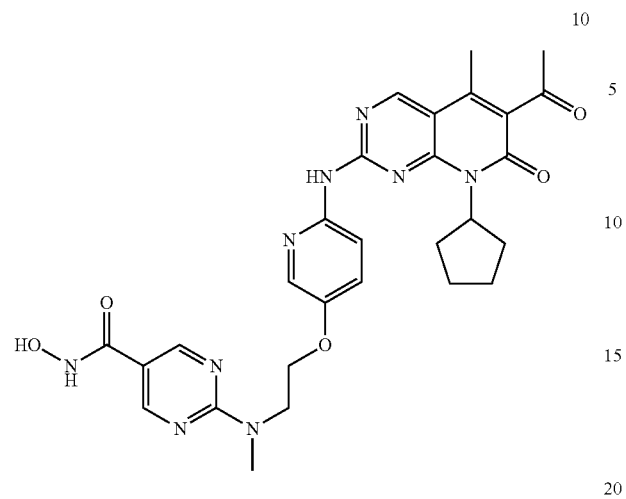
10
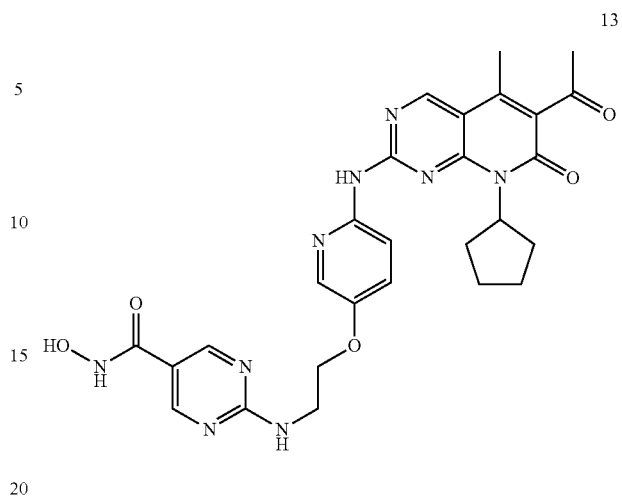
13
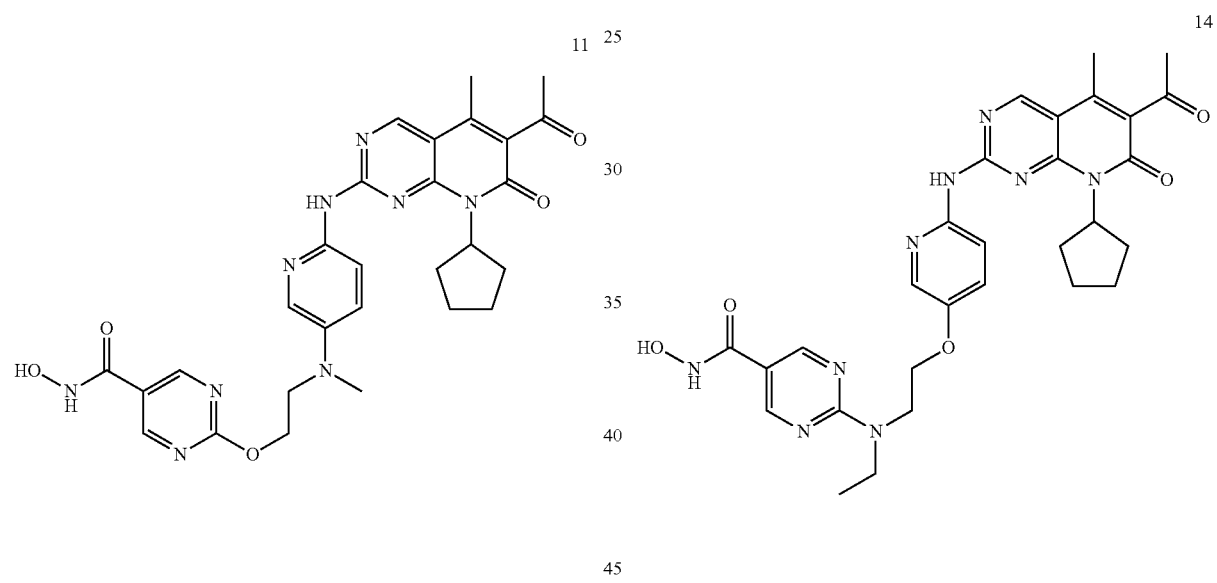
11
12
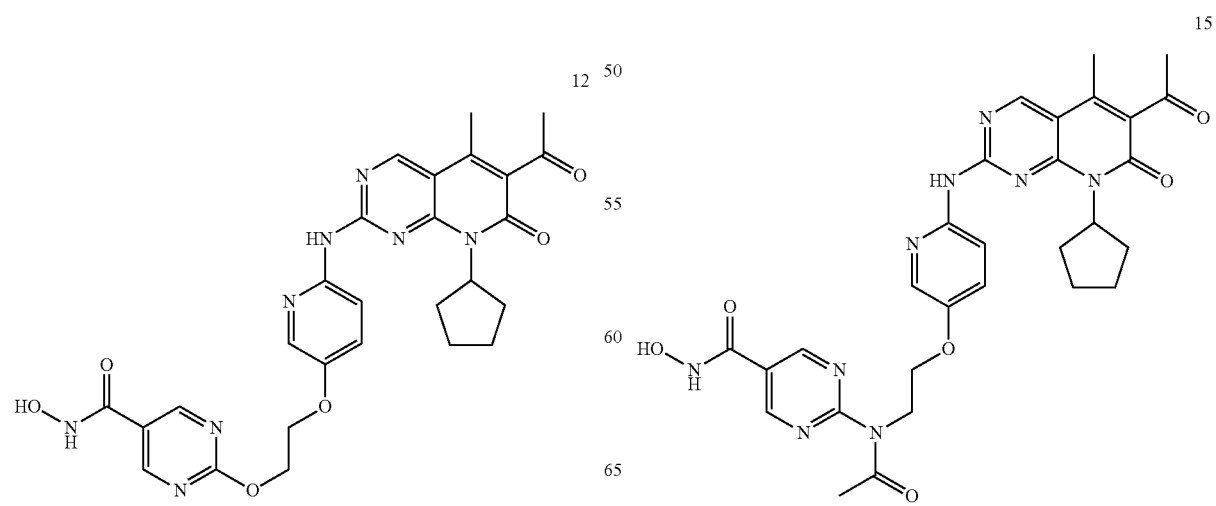
14
15

16
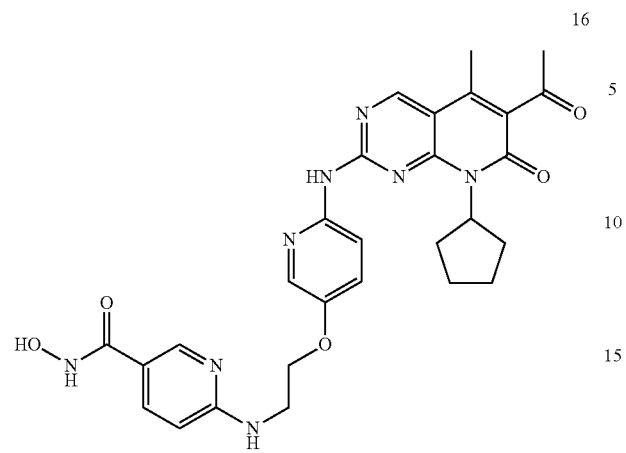
17
19
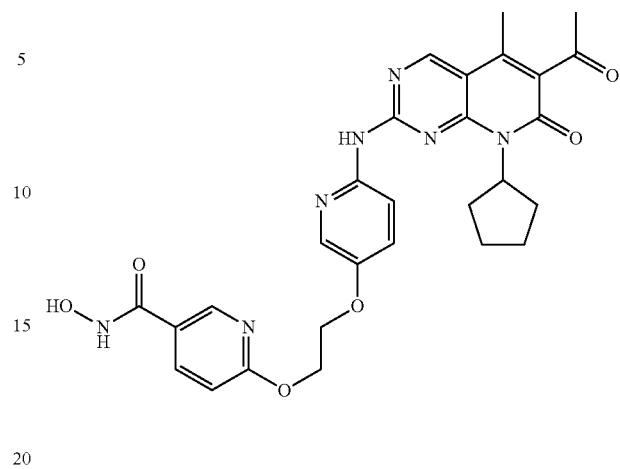
20
18
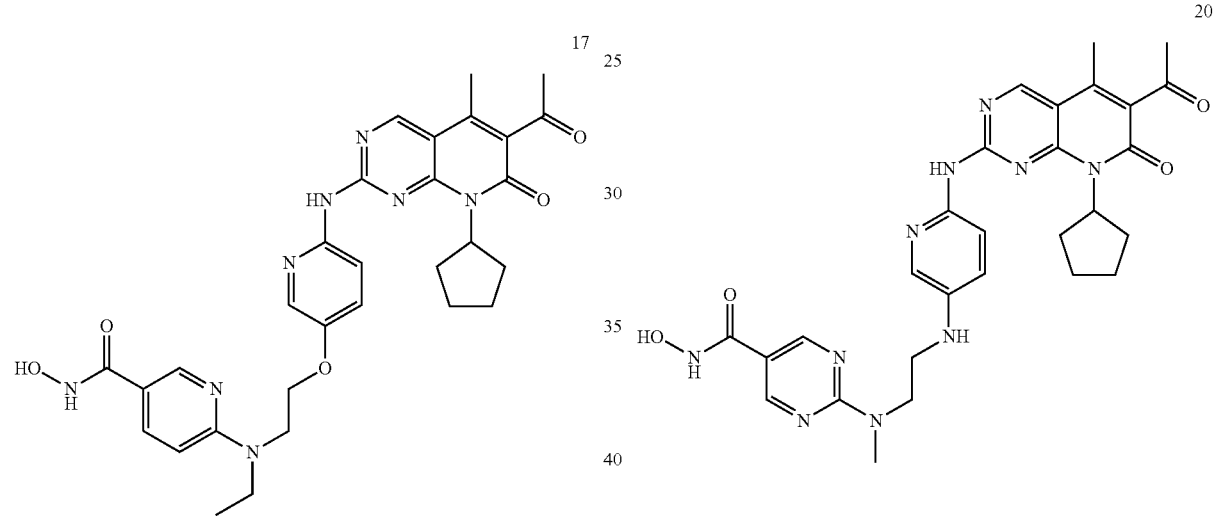
21
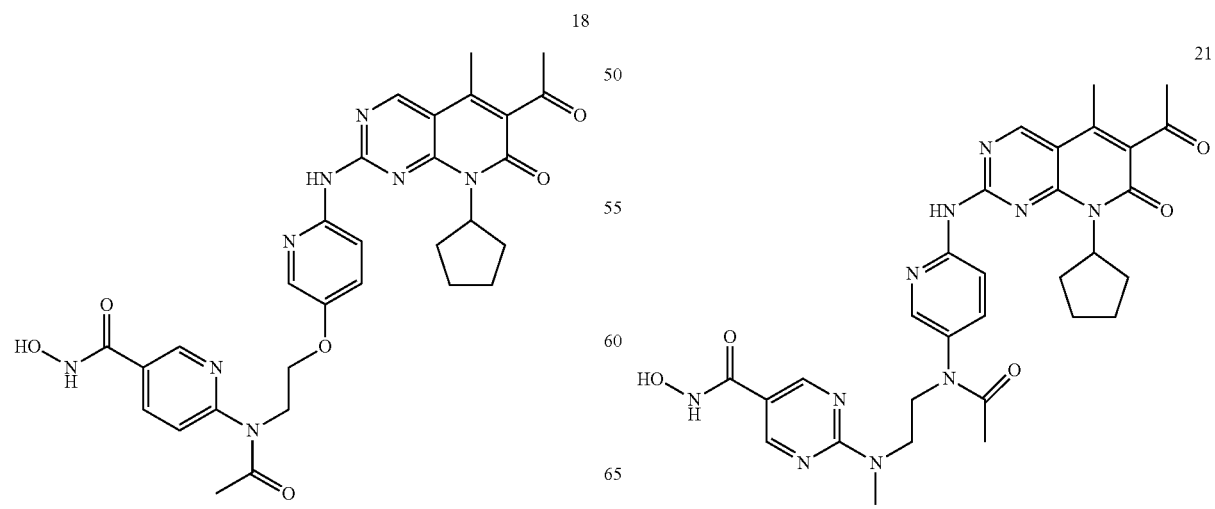

22
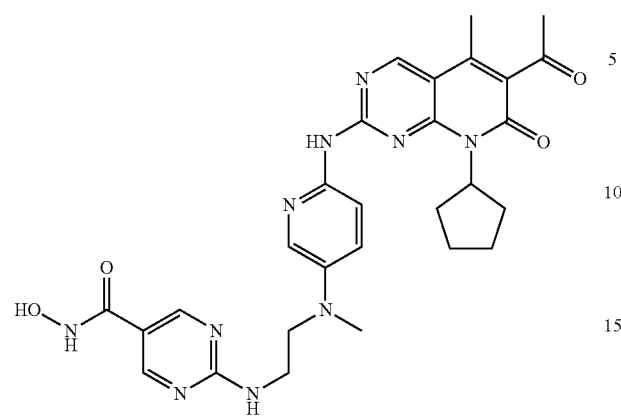
23
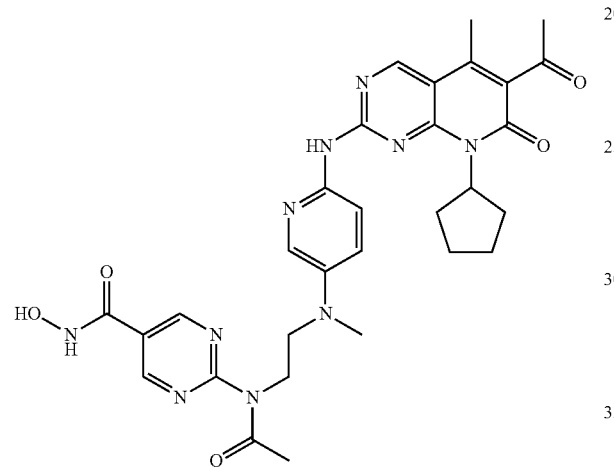
24
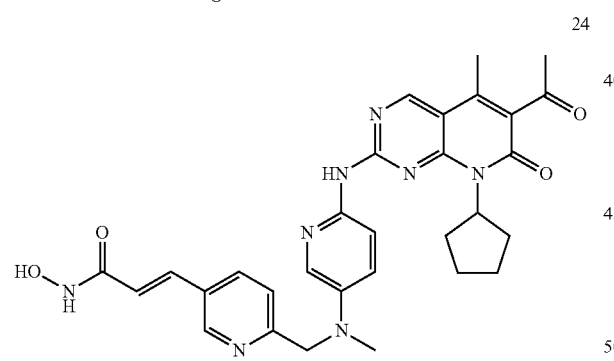
25
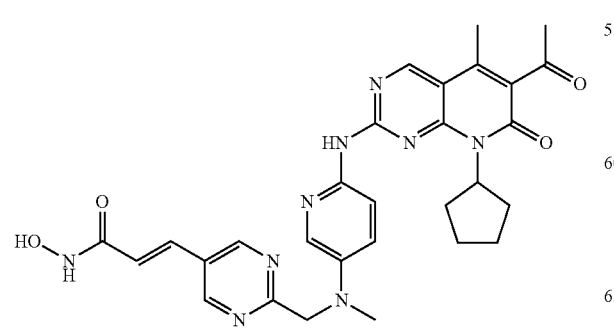
26
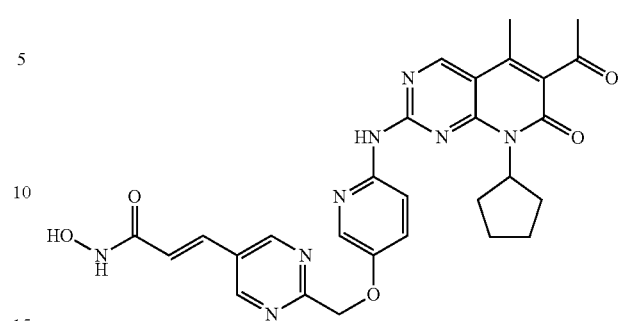
27
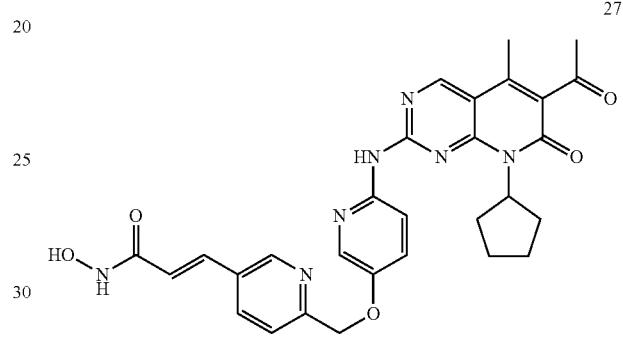
28
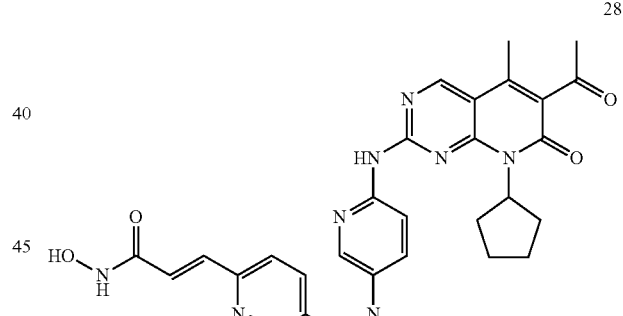
29
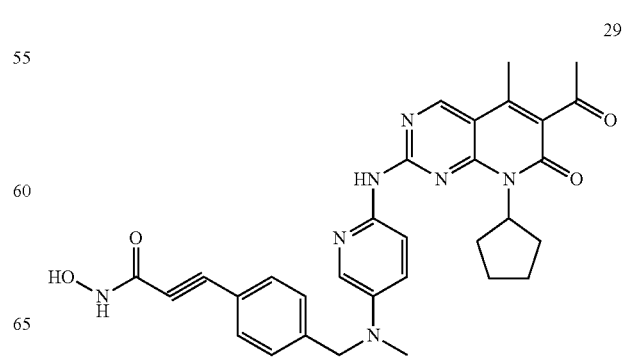

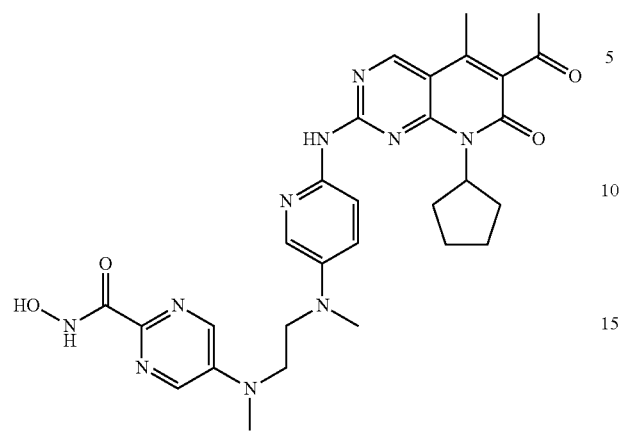
30
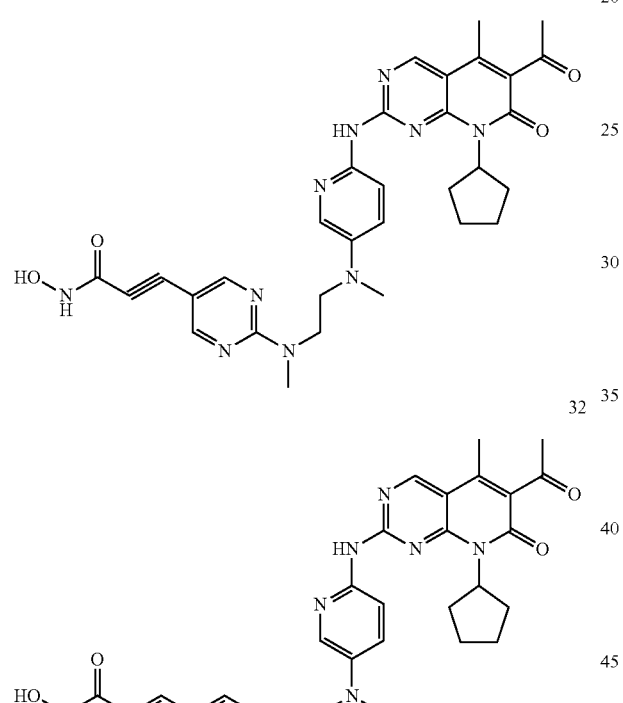
31
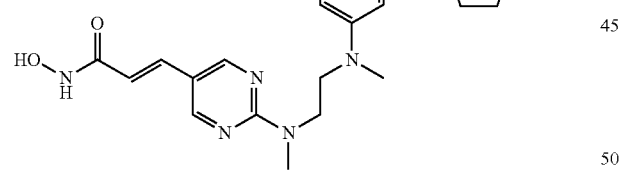
32
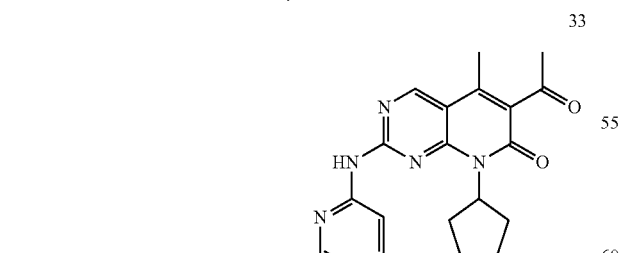
33
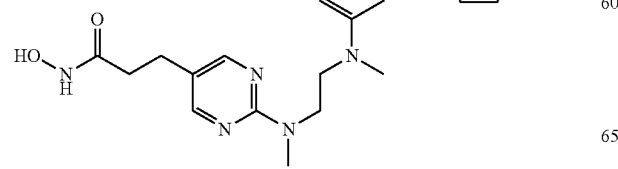
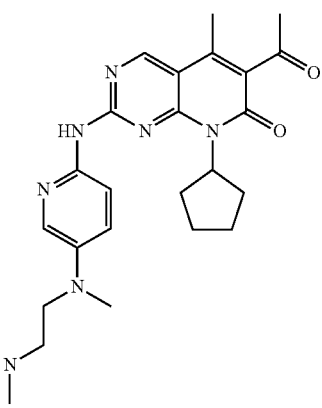
34
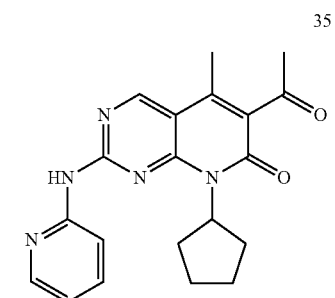
35
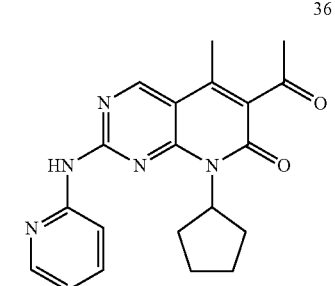
36

37
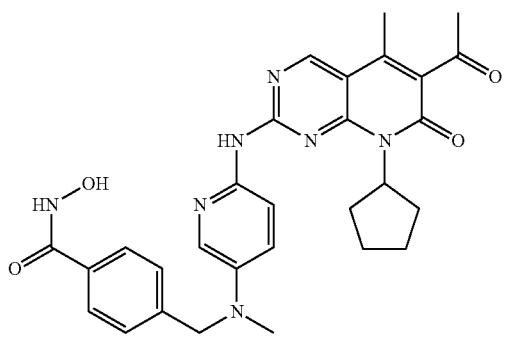
38
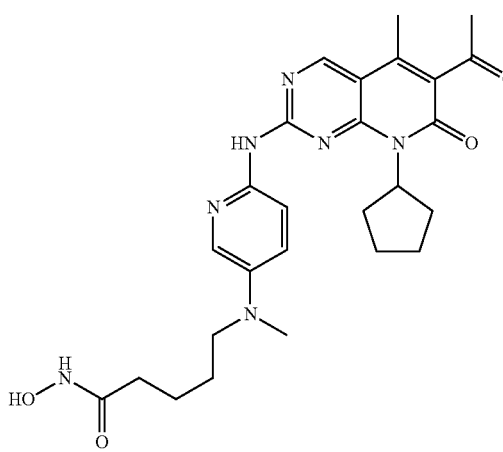
39
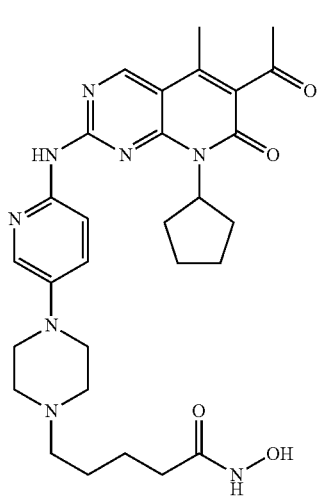
40
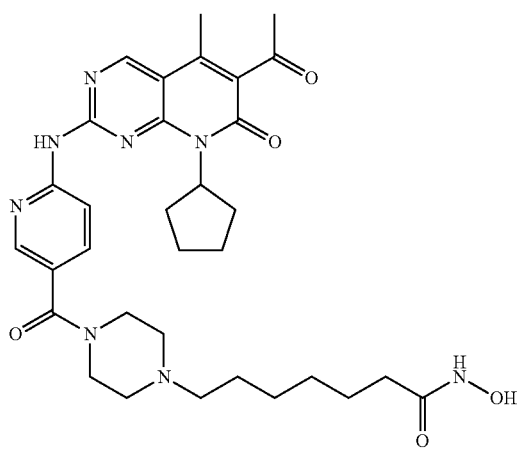
41
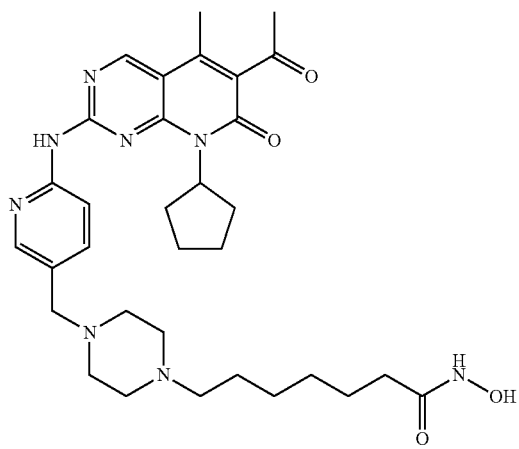
42
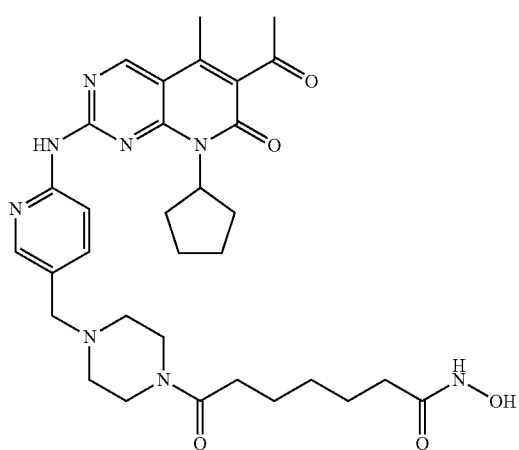

43
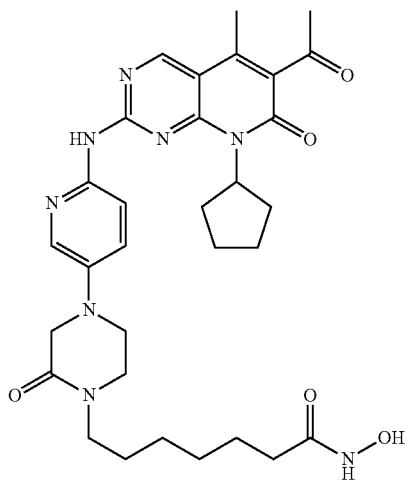
44
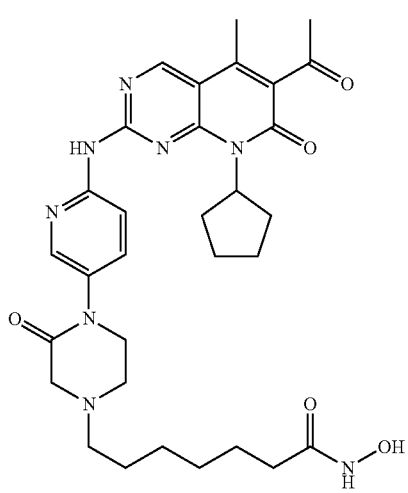
45
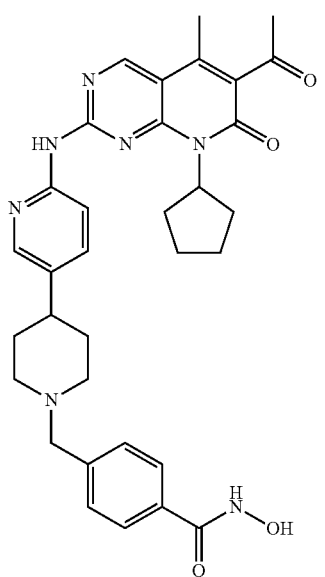
46
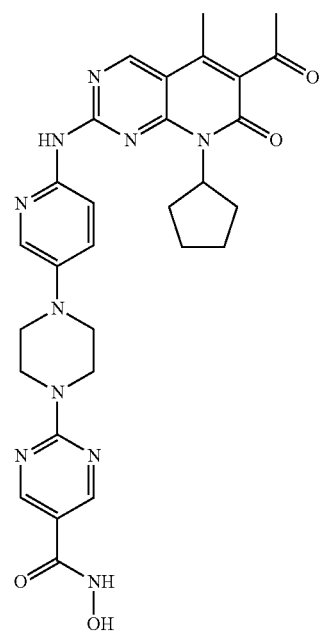
47
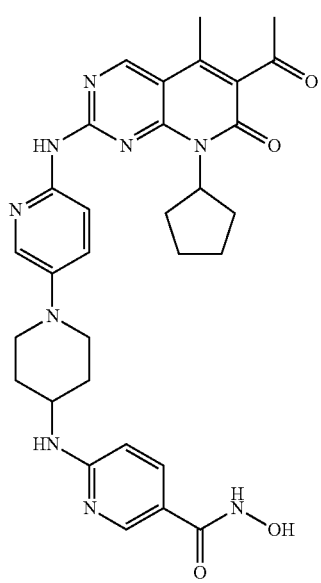
48
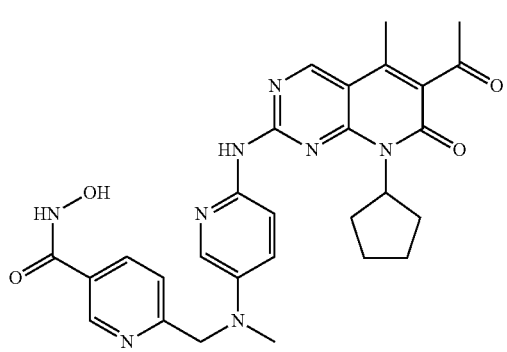

49
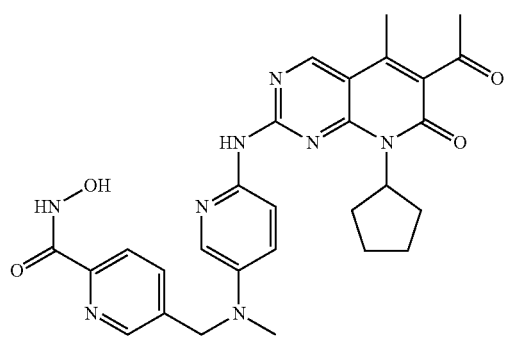
50
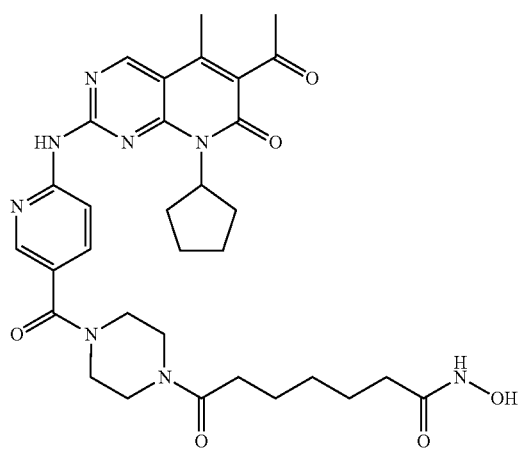
51
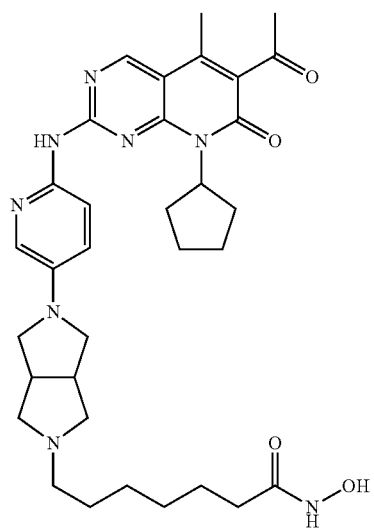
52
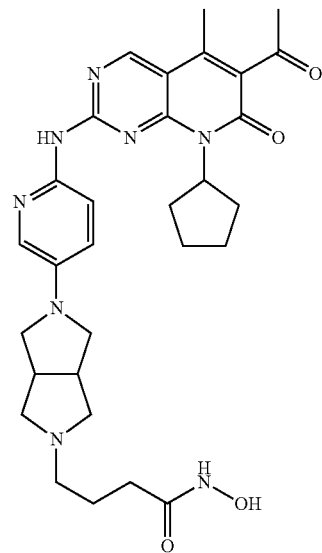
53
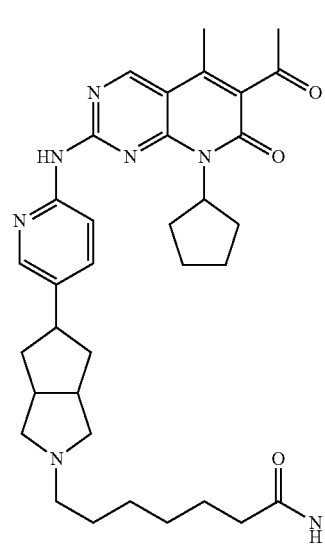
54
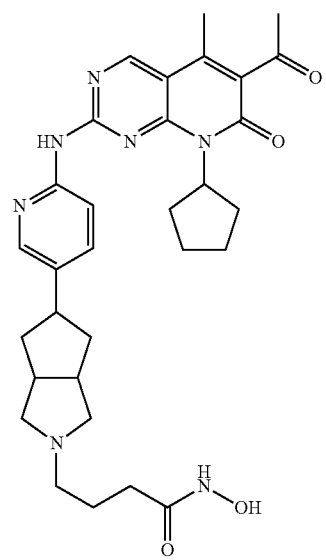

33
-continued

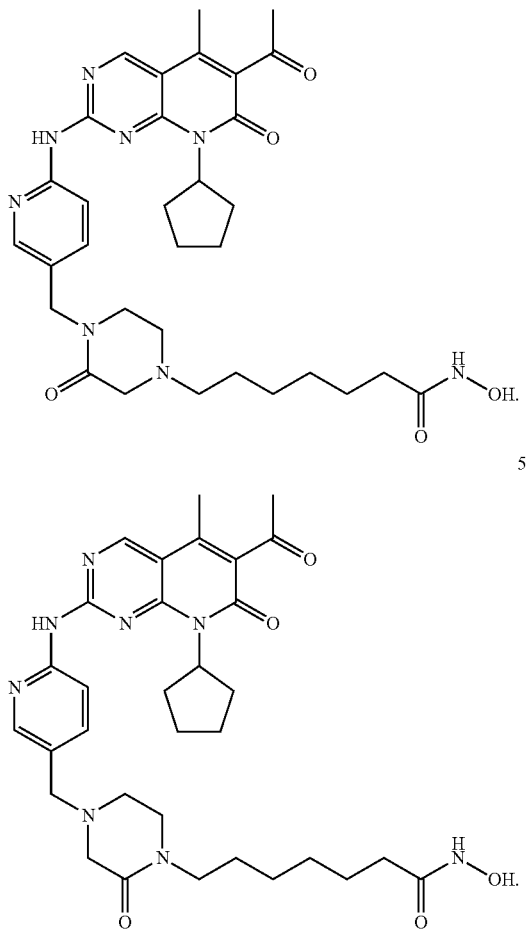

55

56

In the second aspect of the present invention, a pharmaceutical composition is provided, which comprising the compounds of the first aspect of the present invention, or a deuterated derivatives at any possible position in the molecules, their diastereomer, and their enantiomer, or their corresponding pharmaceutically acceptable salts, prodrugs, hydrates, solvates, and pharmaceutically acceptable carriers or excipients.

In the third aspect of the present invention, a compound of the first aspect of the present invention, or deuterated derivatives at any possible position in the molecule, its diastereomer, and its enantiomer, or its corresponding pharmaceutically acceptable salts, prodrugs, hydrates, and solvates in use of the preparation of pharmaceutical compositions for the treatment and/or prevention of diseases or disorders mediated by cyclin-dependent kinases or histone deacetylases use.

In another preferred embodiment, the disease or condition is selected from the group consisting of breast cancer, lymphoma, leukemia, lung cancer, ovarian cancer, liver cancer, melanoma, colon cancer, rectal cancer, kidney cells cancer, small bowel cancer, esophageal cancer, bladder cancer, prostate cancer, or pharyngeal cancer.

It should be understood that, in the present invention, the technical features (such as embodiments) specifically described in the context can be combined with each other to form a new or preferred technical solution, and no special instructions are required.

34
DETAILED DESCRIPTION OF THE INVENTION

Definitions

As use herein, unless clearly indicated otherwise, use of the terms "a", "an" and the like refers to one or more.

As used herein, the word "or" has the meaning of both "or" and "and" and is equivalent to "and/or"—unless otherwise specifically limited to just "or".

As used herein, unless otherwise stated, a chiral carbon atom (or chiral center) of the compound(s) in the invention is optionally R-type, S-type, or a combination thereof.

As used herein, unless otherwise stated, the term "alkyl" by itself or as part of another substituent (which may include the short form of "alk," e.g., alkoxy), refers to a straight (i.e. unbranched), branched chain, or cyclic hydrocarbon radical, or combination thereof, which may be fully saturated, mono- or polyunsaturated and can include di- and multivalent radicals. When an alkyl is preceded by a carbon-number modifier, e.g., $C_{1-10}$, its means the alkyl group contains 1 to 10 carbon atoms. For instance, examples of $C_{1-8}$ alkyl may include a linear or branched alkyl having 1-8 carbon atoms, such as methyl, ethyl, propyl, isopropyl, butyl, isobutyl, sec-butyl, and t-butyl.

As used herein, the term "alkenyl," by itself or as part of another substituent, refers to a straight chain, or branched hydrocarbon chains having at least one carbon-carbon double bond. An alkenyl group with one double bond can be denoted as $-C_nH_{2n-1}$ or $-C_nH_{2n-3}$ with two double bonds. When an alkenyl is preceded by a carbon-number modifier, e.g., $C_{2-8}$, it means the alkenyl group contains 2 to 8 carbon atoms. For instance, examples of $C_{2-8}$ alkenyl may include vinyl, allyl, 1,2-butenyl, 2,3-butenyl, and butadienyl etc.

As used herein, the term "alkynyl," by itself or as part of another substituent, refers to an aliphatic hydrocarbon group with at least one carbon-carbon triple bond. An alkynyl group may be linear or branched or combinations thereof. In some embodiments, it can contain 2 to 12 (e.g., 2 to 8, 2 to 6, or 2 to 4) carbon atoms. When an alkynyl is preceded by a carbon-number modifier, e.g., $C_{2-8}$, it means the alkynyl group contains 2 to 8 carbon atoms. Examples of an alkynyl group (e.g., $C_{2-8}$ alkynyl) may include acetenyl, propynyl, isopropynyl, 1-butynyl, isobutynl, and sec-butynyl etc.

As used herein, the term "cycloalkyl" by itself or as part of another substituent, refers to a saturated or partially saturated carbocyclic mono-, bi-, or tri-cyclic (fused or bridged or spiral) ring system. It can contain 3 to 12 (e.g., 3 to 10, or 5 to 10) carbon atoms. When a cycloalkyl group is preceded by a carbon-number modifier, e.g., $C_{3-10}$, it means the cycloalkyl group contains 3 to 10 carbon atoms. In some embodiments, the term "$C_{3-10}$ cycloalkyl" may refer to a saturated or partially saturated mono- or bicyclic alkyl ring system containing 3 to 10 carbon atoms, such as cyclopropyl, cyclobutyl, cyclopentyl, cyclohexyl, and cycloheptyl. Below are some examples of cycloalkyl group.

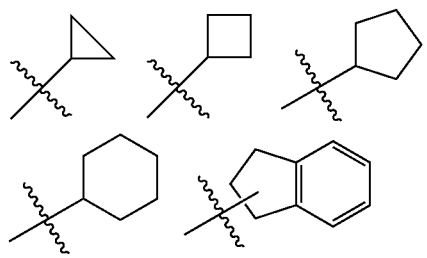

-continued

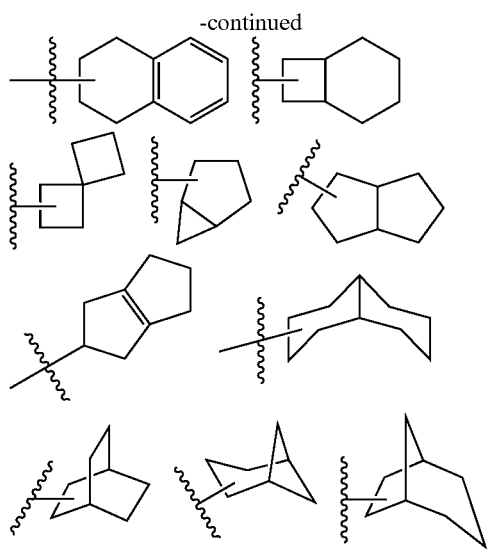

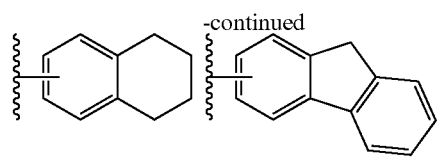
-continued

The cycloalkane structure is derived from the cycloalkyl group, the cyclic structure containing carbon and hydrogen, and has two attaching sites (while the cycloalkyl group has only one attaching site).

As used herein, the term "alkoxy" or "alkyloxy" refers to an alkyl group linked by an oxygen atom (i.e., —O-alkyl), wherein alkyl is as defined above. Specific examples of "alkoxy" include, but are not limited to, methoxy, ethoxy, n-propoxy, isopropoxy, n-butoxy, iso-butoxy, sec-butoxy, t-butoxy, cyclohexyloxy, and cyclopentyloxy. An alkoxy group can be optionally substituted with one or more appropriate substituents such as halogen, amino, cyano, or hydroxyl. An alkoxy group can be straight or branched. When an alkoxy group is preceded by a carbon-number modifier, e.g., $C_{1-8}$, it means the alkoxy group contains 1 to 8 carbon atoms.

As used herein, the term "halo" or "halogen," by itself or as part of another substituent (e.g., haloalkyl), may refer to and include F, Cl, Br, and/or I.

As used herein, a "carbonyl" group refers to —C(O)— or —C(=O)—.

As used herein, the term "aryl," by itself or as part of another substituent, refers to and includes monocyclic, bicyclic, or polycyclic aromatic hydrocarbon radicals. An aryl group can be substituted or unsubstituted. When an aryl group is preceded by a carbon-number modifier, e.g., $C_{6-12}$, it means the aryl group contains 6 to 12 carbon atoms. Aryl group can be fused with another all-carbon containing cyclic structure (including saturated, partially saturated or aromatic ring). But the attaching point to the parent structure has to be from aromatic ring system to be able to qualify as aryl. When attaching point to parent structure is on a saturated carbon atom, it can be called as cycloalkyl instead of aryl. Examples of an aryl group include but are not limited to phenyl, biphenylyl, and naphthyl. Below are some examples of aryl group.

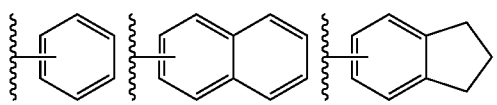

Aromatic ring is derived from the aryl group, has two connection sites, contains carbon and hydrogen atoms, aromatic structural fragments.

As used herein, the term "heteroaryl" by itself or as part of another substituent, refers to a monocyclic or polycyclic aromatic hydrocarbon radicals, having the number of annular carbon atoms designated (e.g., $C_{4-10}$ means four to ten annular carbon atoms) and containing at least one or more of the same or different heteroatoms each independently being N, O, or S. Each carbon atom may be optionally substituted. A heteroaryl group may be 5- to 15-membered aromatic group containing 1 to 4 heteroatoms each independently being N, O, or S. A heteroaryl group may include a nitrogen containing heteroaryl, an oxygen containing heteroaryl, a sulfur containing heteroaryl.

As used herein, the term "nitrogen containing heteroaryl" refers to an aromatic group having one or more nitrogen atoms in the ring(s). Preferably, it is $C_{4-10}$ nitrogen containing heteroaryl which is an aromatic group having 4 to 10 carbon atoms and one or more nitrogen atoms in the ring. Specific examples include but are not limited to substituted or unsubstituted pyridinyl, pyrimidinyl, and pyrrolyl.

As used herein, the term "oxygen containing heteroaryl" refers to an aromatic group having one or more oxygen atoms in the ring(s). Preferably, it is $C_{4-10}$ nitrogen-containing heteroaryl which is an aromatic group having 4 to 10 carbon atoms and one or more oxygen atoms in the ring(s), such as optionally substituted furyl and benzofuryl.

As used herein, the term "sulfur containing heteroaryl" refers to an aromatic group having one or more sulfur atoms in the ring(s). Preferably, it is $C_{4-10}$ sulfur containing heteroaryl which is an aromatic group having 4 to 10 carbon atoms and one or more sulfur atoms in the ring, such as optionally substituted thienyl.

Below are some examples of heteroaryl group.

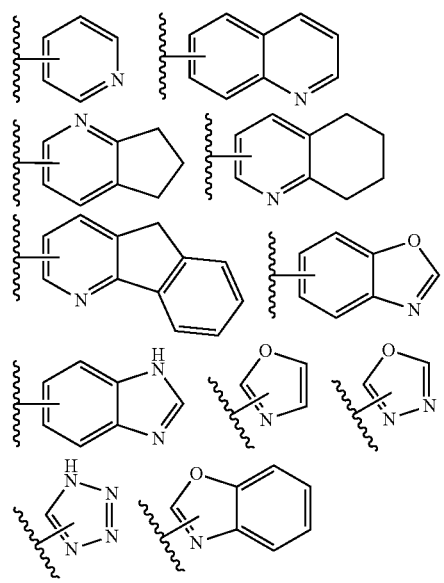

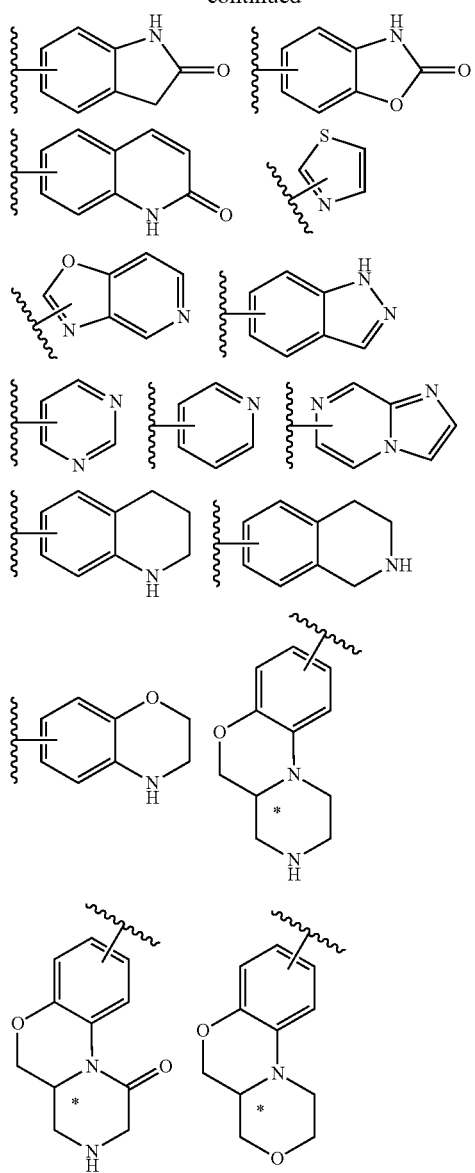
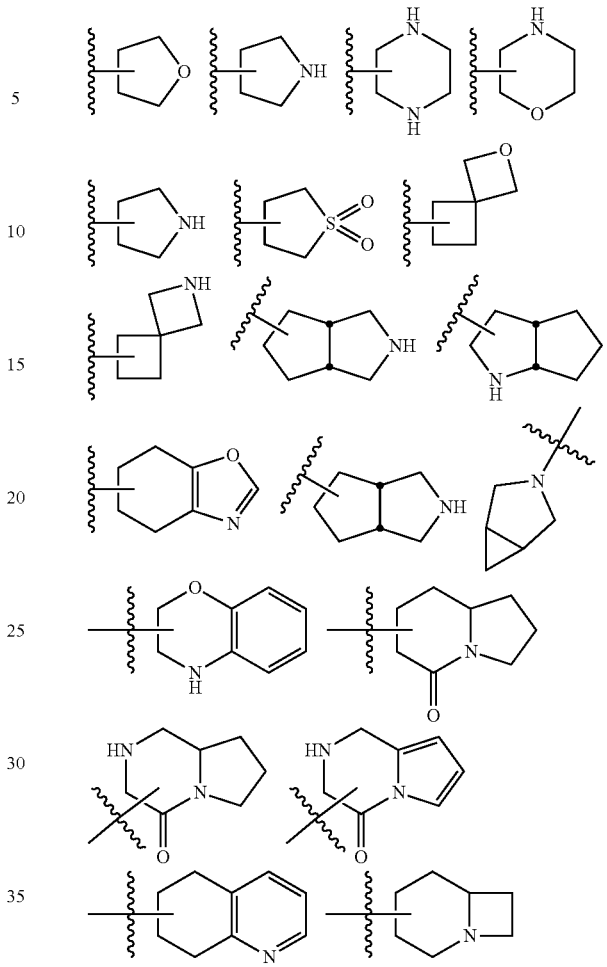

Heteroaryl rings are structural fragments derived from heteroaryl group, which have two connection sites and aromaticity, and contain a least one heteroatom selected from N, S, and O in addition to carbon and hydrogen atoms.

As used herein, the term "heterocyclyl" by itself or as part of another substituent, refers to mono- or polycyclic radicals which may be saturated, partially saturated, or fully unsaturated, having the number of annular carbon atoms designated (e.g., $C_{3-11}$ means three to eleven annular carbon atoms) and containing at least one or more of the same or different heteroatoms each independently being N, S, or O. A heterocyclyl group may be 3- to 15-membered group containing 1 to 4 heteroatoms each independently being N, O, or S. A heteroaryl group may include a nitrogen containing heterocyclyl, oxygen containing heterocyclyl, and sulfur containing heterocyclyl, nitrogen and oxygen containing heterocyclyl, nitrogen and sulfur containing heterocyclyl, sulfur and oxygen containing heterocyclyl, etc. Below are some examples of heterocycle.

Heterocycles are derived from the heterocyclic groups, which have two connection sites, and contain at least one heteroatom selected from N, S, and O cyclic, non-aromatic structure fragments, in addition to carbon and hydrogen atoms.

As used herein, the term "optionally" (e.g., as in "optionally substituted with") means that the moiety at issue is either substituted or not substituted, and that the substitution occurs only when it is chemically feasible. For instance, H cannot be substituted with a substituent and a covalent bond or —C(=O)— group cannot be substituted with a substituent.

As used herein, an "oxo" or "oxide" group refers to =O.

As used herein, the term "pharmaceutically acceptable salt"—unless otherwise specified—refers to salts which are suitable for use in contact with the tissues of a subject (e.g., human) without excessive adverse effect. In some embodiments, pharmaceutically acceptable salts include salts of a compound of the invention having an acidic group (e.g., potassium salts, sodium salts, magnesium salts, calcium salts) or a basic group (e.g., sulfate, hydrochloride, phosphate, nitrate, carbonate).

As used herein, the term "substituted" whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds. Examples of the substituents include but are not limited to $C_{1-8}$ alkyl, $C_{2-8}$ alkenyl, $C_{2-8}$ alkynyl, $C_{3-10}$ cycloalkyl, $C_{1-8}$ alkyloxy, halogen, hydroxyl, carboxyl(—COOH), $C_{1-8}$ aldehyde, $C_{2-10}$ acyl, $C_{2-10}$ ester, amino, amido, phenyl. For instance, a phenyl may be optionally substituted with 1-3 substituents each independently is halogen, $C_{1-10}$ alkyl, cyano, OH, nitro, $C_{3-10}$ cyclic hydrocarbyl, $C_{1-8}$ alkoxy, or amino.

For convenience and as commonly understood, the term "optionally substituted" only applies to the chemical entities that can be substituted with suitable substituents, not to those that cannot be substituted chemically.

Unless specifically otherwise defined, all the terms used herein have their common meanings as known to a skilled person in the art.

In one preferred embodiment, a compound of Formula (I) is selected from the compounds shown above.

In a preferred embodiment, $R^1$, $R^2$, $R^3$,

A, W, V, p and q in Formula (I) independently are selected from the corresponding groups or structure fragments included by the specific compounds shown above.

It should be understood that compounds of formula (I) may also have various derivatives, for example, any hydrogen atom of which may have derivatives rich in deuterium, or crystal forms and salts formed by compounds of formula (I). The derivatives can be easily obtained by those skilled in the art after reading the contents of the present invention.

General Synthetic Schemes for the Compounds of this Invention

Abbreviations $Boc_2O$=di-tert-butyl dicarbonate
$Cs_2CO_3$=cesium carbonate
DCM=dichloromethane
DIPEA=N,N-diisopropylethylamine
DMAP=4-dimethylaminopyridine
DMF=N,N-dimethylformamide
DMSO=dimethyl sulphoxide
e.e.=enantiomeric access
EtOAc or EA=ethyl acetate
HATU=(1-[bis(dimethylamino)methylene]-1H-1,2,3-triazolo[4,5-b]pyridinium 3-oxide hexafluorophosphate)
$MgCl_2$=magnesium chloride
$NH_4HCO_3$=ammonium bicarbonate
$Pd(OAc)_2$=palladium(II) acetate
$Pd_2dba_3$=tris(dibenzylideneacetone)dipalladium(0)
PE=petroleum ether
RT=room temperature
TEA=triethylamine
TFA=trifluoroacetic acid Generally, each reaction is usually carried out in an inert solvent at a reaction temperature of −40° C. to reflux (such as 100 or 120° C.). The reaction time in each step is usually from 1 to 72 h, preferably from 0.1 to 24 h or 0.2-12 h.

Method A describes a general synthetic method for compound (I).

Method A

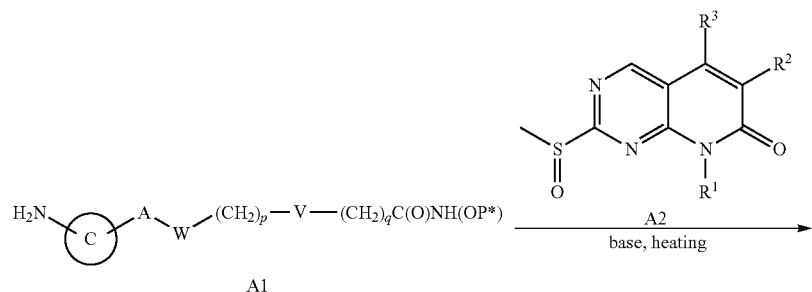

A1

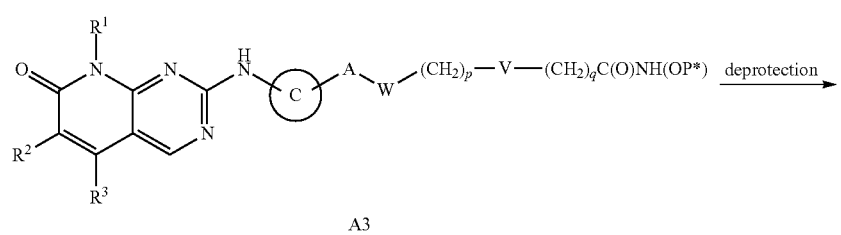

A3

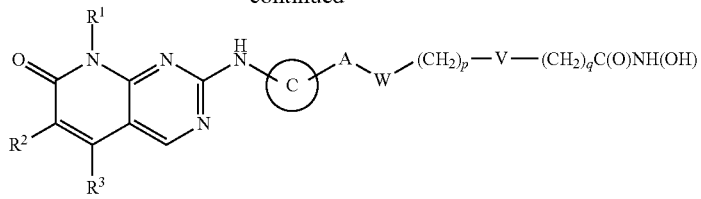
(I)
P*: protecting group
Intermediate A2 was prepared according to WO2017/101763 and the literatures cited therein.
Method B showed the synthesis of intermediate A1.
Method B
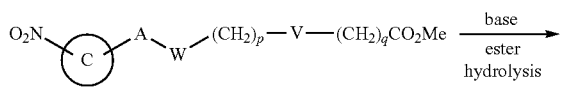
A4
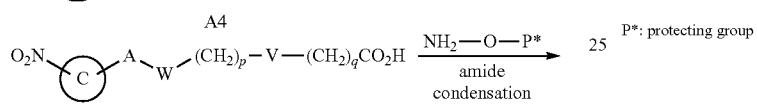
A5
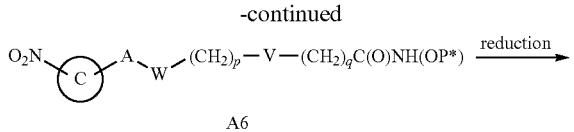
A6
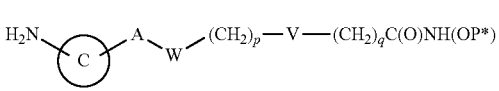
A1
P*: protecting group
Method C showed another synthetic method of formalar (I).
Method C
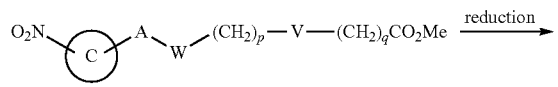
A4
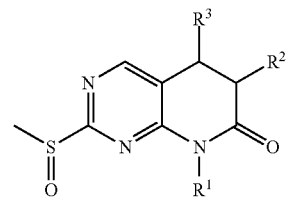
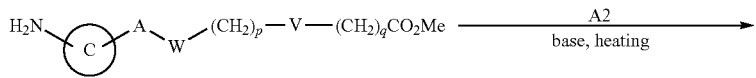
A7
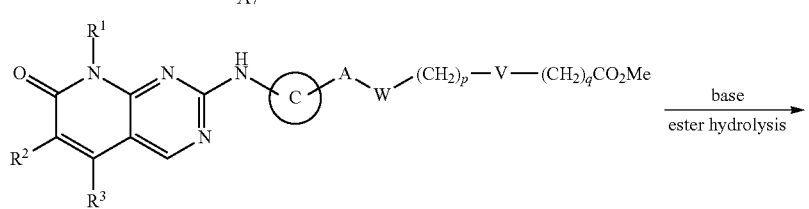
A8
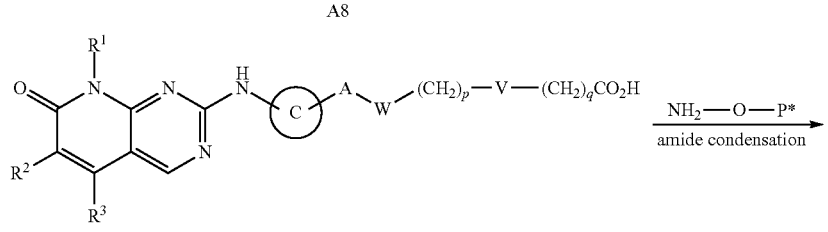
A9

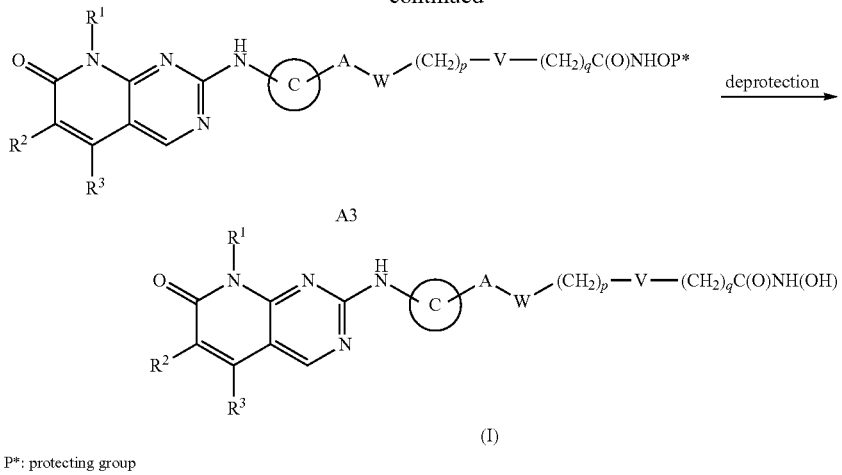

P*: protecting group

In addition to the partial synthesis schemes of formula (I) listed above, there are other schemes for synthesizing formula (I), including the replacement of the synthesis sequence of the schemes listed above, and the use of different catalysts and synthesis methods. These synthesis schemes and methods are understandable and achievable for organic synthesis technicians and workers, so it won't be elaborated further one by one here.

Pharmaceutical Compositions and Administration Thereof

The compounds provided by the present invention are useful as kinase inhibitors, especially as inhibitors of CDK4, CDK6, and HDAC inhibitors. Therefore, these compounds possess outstanding therapeutic effect for cancers.

The pharmaceutical composition according to the present invention comprises (i) a safe and effective amount of the compounds of the invention or the pharmaceutical acceptable salts thereof and (ii) a pharmaceutically acceptable excipient or carrier. As used herein, the term "safe and effective amount" means an amount of the compounds which is sufficient to improve the patient's condition and will not induce any serious side effect. Generally, the pharmaceutical composition contains 0.01-100 mg compounds of the invention/dose, preferably 0.10-10 mg compounds of the invention/dose. In some embodiments, "one dose" refers to a capsule or tablet.

A "pharmaceutically acceptable carrier" means one or more compatible solid or liquid fillers or gel materials, which are suitable for human, and usually must have sufficient purity and sufficiently low toxicity. The term "compatibility" as used herein means that the components of the compositions can be blended with the compounds of the invention or with each other, and would not significantly reduce the efficacy of the compounds. Examples of pharmaceutically acceptable carriers include but are not limited to cellulose and the derivatives thereof (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, and pyrogen-free water.

There is no special limitation to the route of administration for the compounds or pharmaceutical compositions of the invention. The representative administration route includes but is not limited to: oral, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and gum arabic; (c) humectant, such as, glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer.

The solid dosage forms such as tablets, sugar pills, capsules, pills and granules can be prepared by using coating and shell material, such as enteric coatings and other materials known in the art. They can contain opaque agent, and the release of the active compounds or compounds in such compositions can be delayed for releasing in certain portion of the digestive tract. Instance of the embedding components can be polymers and waxes. If necessary, the active compounds and one or more above excipients can be prepared into microcapsules.

Liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides the inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and the suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

The compounds of the invention can be administered alone, or in combination with other pharmaceutically acceptable compounds.

When the pharmaceutical compositions are used, a safe and effective amount of compounds of the present invention is administered or delivered to mammals in need thereof (such as human), wherein the dosage of administration is a pharmaceutically effective amount. For a person weighted about 60 kg, the daily dose is usually 1 to 2000 mg, preferably 20 to 500 mg. Of course, the particular dose should also depend on other factors, such as the route of administration, patient healthy status, etc., which are well within the skill of a skilled physician.

The compounds and pharmaceutical composition of the invention can be used for treating cancer. As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting prostate, lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, hepatic cancer, non-small cell carcinoma of the lung, cancer of the small intestine and cancer of the esophagus. Metastatic lesions of the aforementioned cancers can also be treated or prevented using the methods and compositions of the invention. The subject method can be useful in treating malignancies of the various organ systems, such as those affecting lung, breast, lymphoid, gastrointestinal (e.g., colon), bladder, genitourinary tract (e.g. prostate), pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The examples of cancer include but are not limited to breast cancer, lymph cancer, lung cancer, ovarian cancer, hepatic cancer melanoma, colon cancers, rectal cancer, renal-cell carcinoma, cancer of the small intestine and cancer of the esophagus, bladder cancer, prostate cancer, or pharynx cancer, etc.

The main advantages of the present invention include at least the following:

The invention provides novel heterocyclic compounds useful as kinase inhibitors and histone deacetylase inhibitors. The main feature of the invention is that a single small molecule can simultaneously inhibit multiple different signal pathways, such as cell dependent kinase and histone deacetylase.

The invention reveals that these novel heterocyclic compounds of Formula (I) possess outstanding effect for inhibiting activity of CDK4, CDK6, and HDACs.

The present invention will be further illustrated below with reference to the specific examples. It should be understood that these examples are only to illustrate the invention but not to limit the scope of the invention. Unless indicated otherwise, parts and percentage are calculated by weight.

Example 1. Preparation of 2-((2-((6-(((6-acetyl-8-cyclopentyl-5-methyl-7-oxo-7,8-dihydropyrido[2,3-d]pyrimidin-2-yl) amino) pyridin-3-yl) (methyl) amino) ethyl) (methyl) amino)-N-hydroxypyrimidine-5-carboxamide (Compound 1)

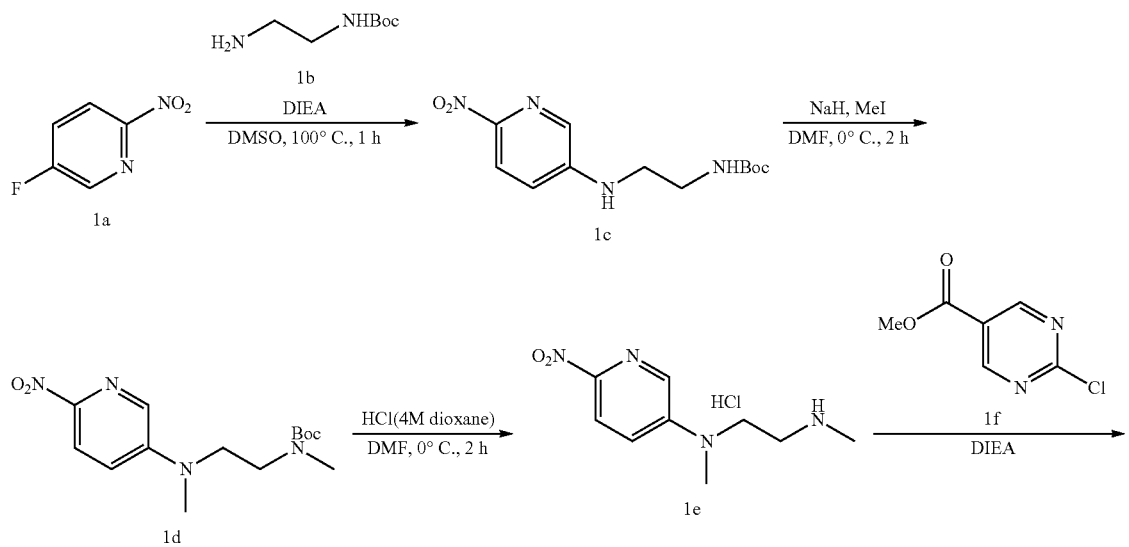

-continued
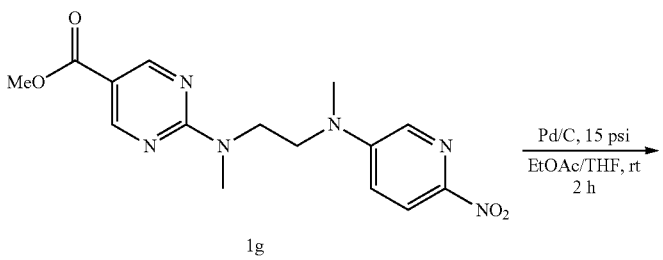
1g
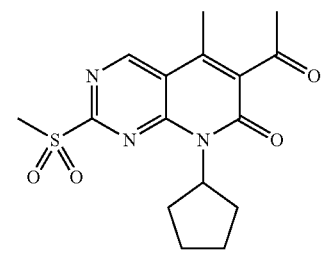
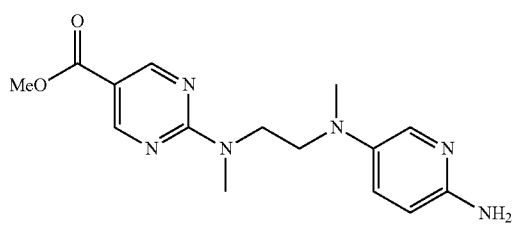
1h
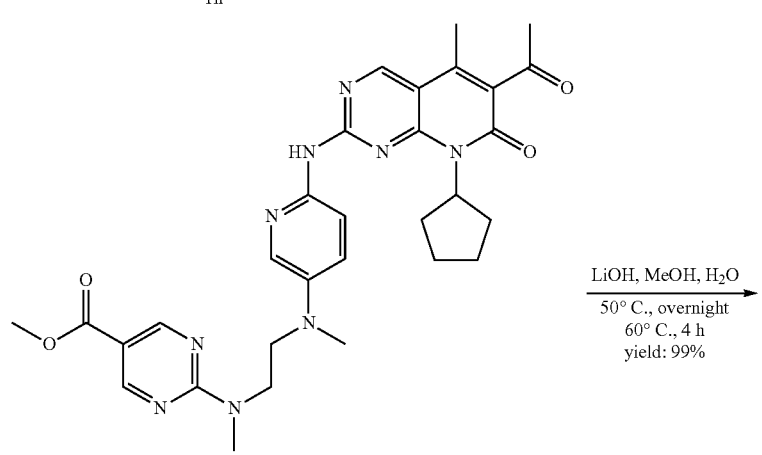
1k
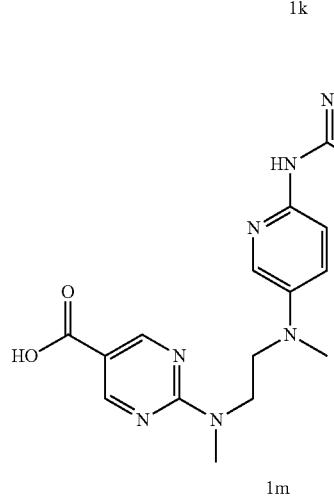
1m
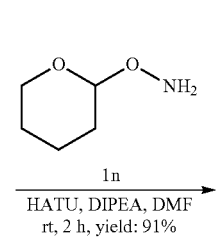
1n

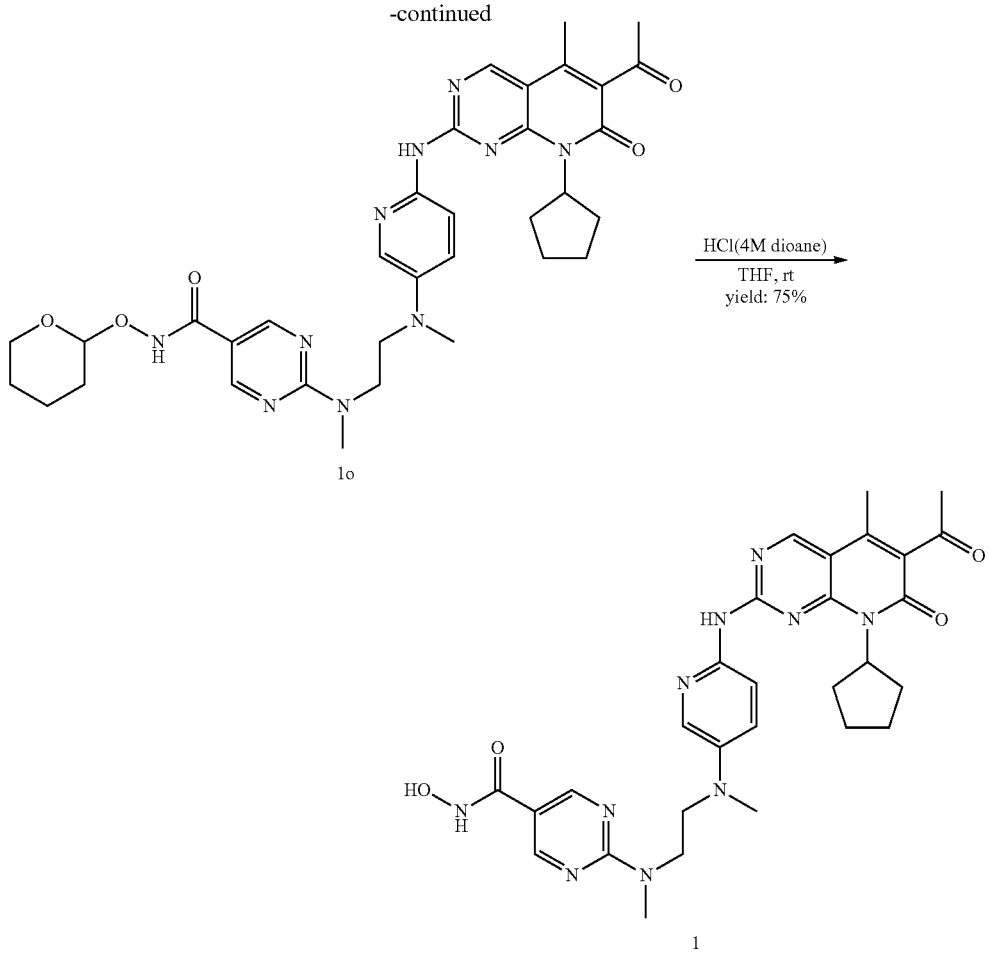

Compound 1a (0.2 g, 1.41 mmol), compound 1b (0.27 g, 1.69 mmol), and DIPEA (0.36 g, 2.82 mmol) were added to DMSO (5 mL). The reaction mixture was heated to 100° C. for 1 hour. The reaction was monitored by TLC for completion. After cooling to room temperature, it was poured in water, and extracted with EtOAc (3 times). The combined organic layers were washed with brine, dried over anhydrous sodium sulfate, and concentrated under reduced pressure. The residue was purified by $SO_2$ column chromatography ($CH_2Cl_2$:MeOH=20:1) to afford compound 1c (0.3 g, yield: 76%) as a yellow oil.

Compound 1c (0.3 g, 1.06 mmol) was added to DMF (10 mL). The reaction mixture was cooled to 0° C. NaH (0.1 g, 2.66 mmol, 60%) was added and the reaction mixture was stirred for 1 hour. $CH_3I$ (0.45 g, 3.19 mmol) was added and the reaction mixture was stirred until the reaction was completed monitored by TLC. It was poured into water, and extracted with EtOAc (3 times). The combined organic layers were washed with brine, dried over anhydrous sodium sulfate, and concentrated to afford compound 1d (0.28 g, yield: 85%) as a yellow solid, which was used in next step without further purification.

Compound 1d (0.28 g, 0.09 mmol) was added to $CH_2Cl_2$ (5 mL) followed by the addition of a solution of HCl in 1,4-dioxane (4 M, 1 mL) at 0° C. The reaction mixture was stirred at room temperature for 2 hours. The reaction was monitored by TLC for completion. It was concentrated under reduced pressure to afford compound 1e (180 mg, yield: 95%) as a yellow solid (This compound was used in next step without further purification).

Compound 1e (280 mg, 1.14 mmol), 1f (254 mg, 1.36 mmol), and DIPEA (293 mg, 2.27 mmol) were added to DMSO (5 mL). The reaction mixture was stirred at 100° C. for 1 hour. The reaction was monitored by TLC for completion. After cooling to room temperature, it was poured into water, and extracted with EtOAc (3 times). The combined organic layers were washed with brine, dried over anhydrous sodium sulfate, and concentrated. The residue was stirred in a mixture of $CH_2Cl_2$ and petroleum ether (1:5) and filtered to afford compound 1g (250 mg, yield: 63.3%) as a yellow solid.

Compound 1h was prepared from compound 1g via Pd—C catalyzed hydrogenation reaction. The reaction mixture was filtered and concentrated under reduced pressure to give crude product, which was used in next step without further purification. MS m/z 317.2 [M+H]$^+$.

Compound 1j was prepared following the procedure in patent WO2017101763.

Compound 1h (200 mg, 0.63 mmol) and compound 1j (64 mg, 0.18 mmol) were added to dry toluene (4 mL) in a sealed tube. The reaction mixture was stirred at 130° C. overnight. The reaction was monitored by LCMS for completion. It was concentrated under reduced pressure and the residue was purified by preparative TLC ($CH_2Cl_2$:MeOH=25:1) to afford 1k (30 mg, yield: 28%) as a yellow solid. MS m/z 586.4 [M+H]$^+$.

Compound 1k (30 mg, 0.05 mmol) and lithium hydroxide hydrate (65 mg, 1.54 mmol) were dissolved in a mixture of methanol (14 mL) and water (6 ml), and the reaction mixture was stirred at 50° C. overnight. The reaction mixture was uncompleted monitored by TLC. It was stirred at 60° C. for 4 hours. The reaction was monitored by TLC for completion. It was concentrated to remove methanol, acidified with aqueous HCl (2 M) to pH=5, and extracted with EtOAc (3 times). The combined organic layers were concentrated to afford compound 1m (30 mg, yield: 99%) as a yellow solid (This compound can be directly used in the next step without further purification). MS m/z 572.2 [M+H]$^+$.

Compound 1m (30 mg, 0.05 mmol), DIEA (20 mg, 0.16 mmol), HATU (30 mg, 0.08 mmol), and o-(tetrahydro-2H-pyran-2-yl) hydroxylamine (in, 9.2 mg, 0.08 mmol) were added to DMF (5 mL). The reaction mixture was stirred at room temperature for 2 hours. The reaction was monitored by LCMS for completion. It was poured into water and filtered. The solid was washed with a solution of AcOH (1 drop) in water (30 mL), and purified by preparative TLC ($CH_2Cl_2$:MeOH=25:1~15:1) to afford compound 1o (32 mg, yield: 91%) as a yellow solid. MS m/z 671.4 [M+H]$^+$.

Compound 1o (29 mg, 0.043 mmol) was added to THF (1 mL) followed by the addition of a solution of HCl in 1,4-dioxane (4 M, 10 drops) and deionized water (10 drops). The reaction mixture was stirred at room temperature for 5 hours. The reaction was monitored by TLC for completion. $Et_2O$ was added and the precipitate was collected via filtration, washed with $Et_2O$ and $CH_3CN$, and dried to afford compound 1 (19 mg, yield: 75%, hydrochloride salt) as a yellow solid. $^1$H NMR (400 MHz, DMSO-$d_6$): δ 11.43 (brs, 1H), 11.13 (brs, 1H), 9.03 (s, 1H), 8.75 (brs, 1H), 8.62 (brs, 1H), 7.96 (d, J=8.4 Hz, 1H), 7.84 (s, 1H), 7.65 (d, J=9.6 Hz, 1H), 5.93-5.75 (m, 1H), 4.37 (brs, 4H), 3.88-3.77 (m, 2H), 3.74-3.64 (m, 2H), 3.15 (s, 3H), 2.98 (s, 3H), 2.45 (s, 3H), 2.37 (s, 3H), 2.28-2.14 (m, 2H), 2.01-1.87 (m, 2H), 1.87-1.74 (m, 2H), 1.66-1.49 (m, 2H). MS m/z 587.3 [M+H]$^+$.

Example 2. Preparation of (E)-3-(4-(((6-((6-acetyl-8-cyclopentyl-5-methyl-7-oxo-7,8-dihydropyrido[2,3-d]pyrimidin-2-yl)amino)pyridin-3-yl)(methyl)amino)methyl)phenyl)-N-hydroxyacrylamide (Compound 2)

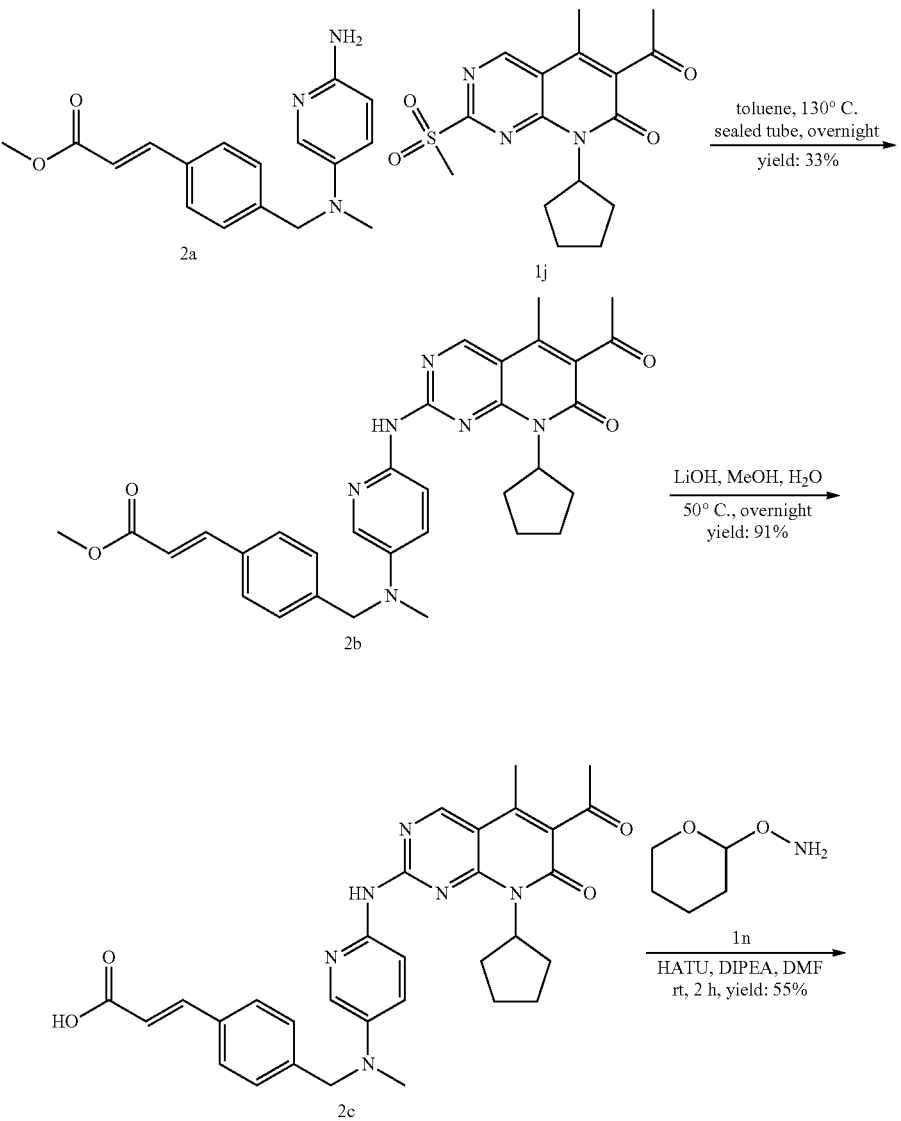

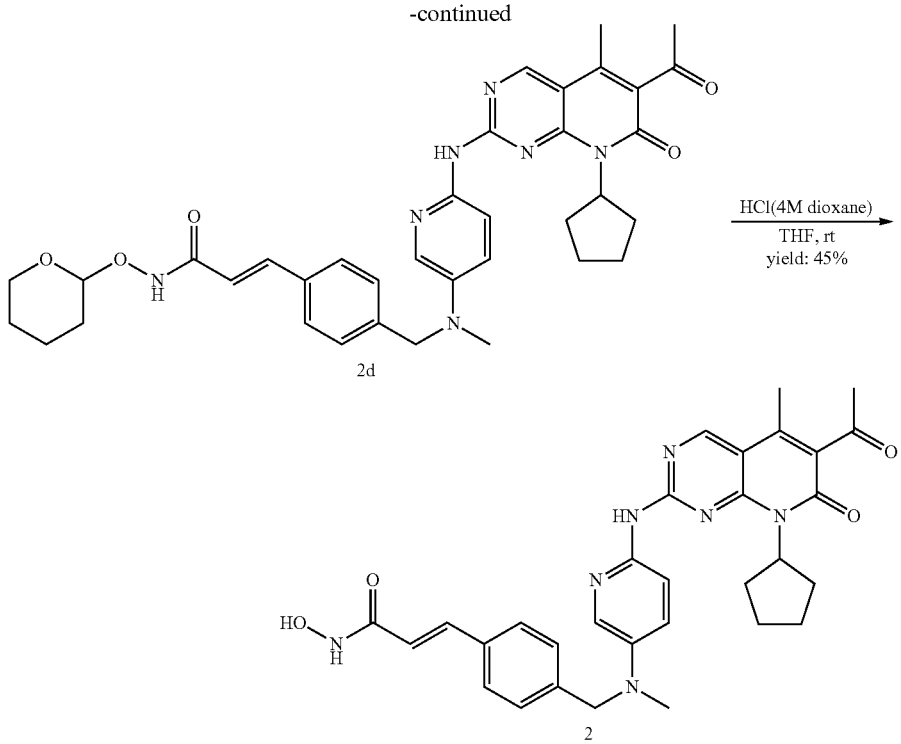

Compound 2a (217 mg, 0.73 mmol) and compound 1j (85 mg, 0.34 mmol) were dissolved in dry toluene (5 mL). The reaction mixture was heated at 130° C. overnight. It was concentrated under reduced pressure. The residue was dispended in saturated aqueous NaHCO$_3$, and extracted with EtOAc (3 times). The combined organic layers were washed with brine, dried over anhydrous sodium sulfate, and concentrated under reduced pressure. The residue was purified by preparative TLC (CH$_2$Cl$_2$:MeOH=25:1) to afford compound 2b (45 mg, yield: 33%) as a yellow solid. MS m/z 567.2 [M+H]$^+$.

Compound 2b (45 mg, 0.08 mmol) and lithium hydroxide hydrate (13 mg, 0.31 mmol) were dissolved in a mixture of methanol (20 mL) and water (5 mL). The reaction mixture was stirred at 50° C. overnight. It was concentrated under reduced pressure to remove methanol, acidified with aqueous HCl to pH=6, and extracted with EtOAc (3 times). The combined organic layers were concentrated under reduced pressure and the residue was purified by SO$_2$ column chromatography (CH$_2$Cl$_2$:MeOH=10:1) to afford compound 2c (40 mg, yield: 91%) as a yellow solid. MS m/z 553.2 [M+H]$^+$.

Compound 2c (40 mg, 0.072 mmol), DIEA (28 mg, 0.217 mmol), HATU (41 mg, 0.109 mmol), and compound in (13 mg, 0.109 mmol) were added to dry THF (5 mL). The reaction mixture was stirred at room temperature overnight. The reaction was monitored by LCMS for completion. It was poured into water and filtered. The solid was washed with a solution of AcOH (1 drop) in water (30 mL), and purified by preparative TLC (CH$_2$Cl$_2$:MeOH=20:1) to afford compound 2d (26 mg, yield: 55%) as a yellow solid. MS m/z 652.4 [M+H]$^+$.

Compound 2d (23 mg, 0.035 mmol) was added to THF (1 mL) followed by the addition of a solution of HCl in 1,4-dioxane (4 M, 10 drops) and deionized water (10 drops) at room temperature. The reaction mixture was stirred at room temperature for 10 hours. The reaction was monitored by LCMS for completion. Et$_2$O was added and the precipitate was collected via filtration. The solid was washed with Et$_2$O and dried to afford crude product, which was further purified by preparative HPLC to afford compound 2 (9 mg, yield: 45%, hydrochloride salt) as a yellow solid. $^1$H NMR (400 MHz, DMSO-d$_6$): δ 10.75 (brs, 1H), 10.00 (s, 1H), 9.04 (brs, 1H), 8.92 (s, 1H), 7.87 (d, J=3.2 Hz, 1H), 7.69 (d, J=9.2 Hz, 1H), 7.52 (d, J=8.0 Hz, 2H), 7.42 (d, J=15.2 Hz, 1H), 7.31-7.20 (m, 3H), 6.42 (d, J=16.0 Hz, 1H), 5.83-5.69 (m, 1H), 4.62 (s, 2H), 3.06 (s, 3H), 2.41 (s, 3H), 2.29 (s, 3H), 2.26-2.13 (m, 2H), 1.87-1.65 (m, 4H), 1.56-1.42 (m, 2H). MS m/z 568.4 [M+H]$^+$.

Example 3. Preparation of 6-((2-((6-((6-acetyl-8-cyclopentyl-5-methyl-7-oxo-7,8-dihydropyrido[2,3-d]pyrimidin-2-yl)amino)pyridin-3-yl)(methyl)amino)ethyl)(methyl)amino)-N-hydroxynicotinamide (Compound 3)

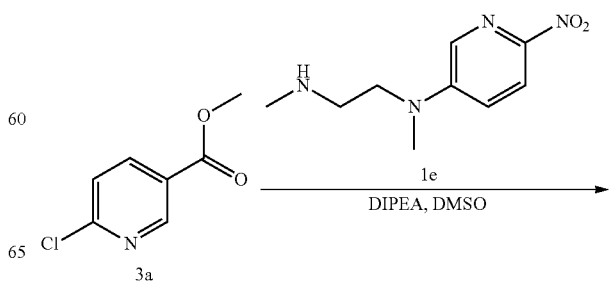

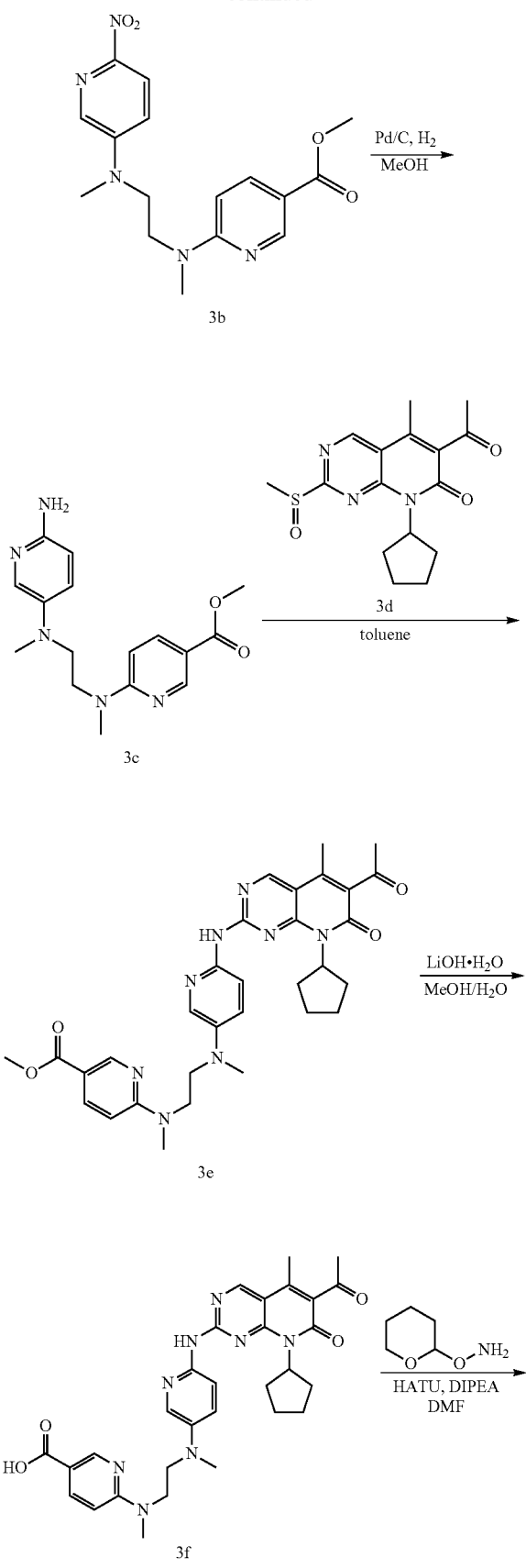

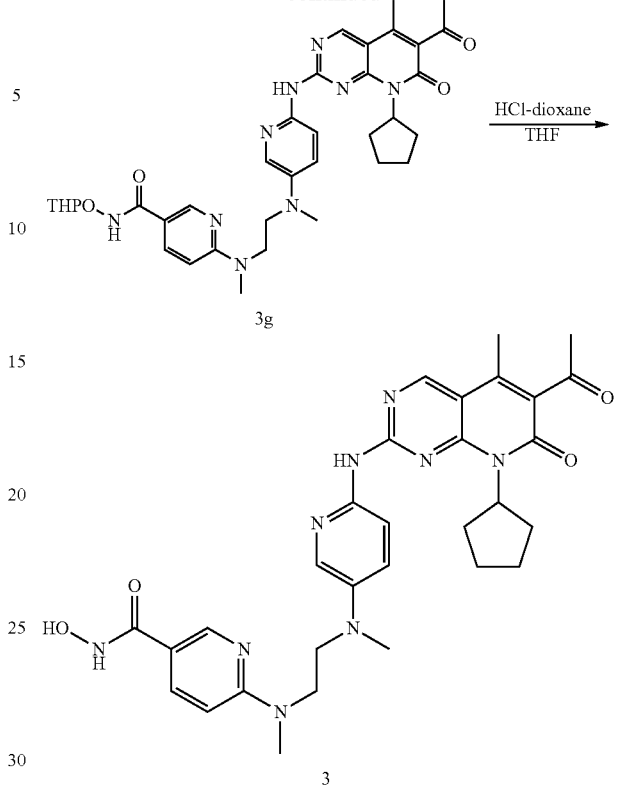

Compound 3a (1.0 g, 5.83 mmol), compound 1e (1.23 g, 5.83 mmol), and DIPEA (1.50 g, 11.66 mmol) were added to DMSO (10 mL). The reaction mixture was heated at 100° C. for 16 hours. The reaction was monitored by LCMS for completion. After cooling to room temperature, it was poured into water, and extracted with EtOAc (3 times). The combined organic layers were washed with brine, dried over anhydrous sodium sulfate, and concentrated under reduced pressure. The residue was stirred in a mixture of $CH_2Cl_2$ and petroleum ether (1:5), and filtered to afford compound 3b (1.0 g, yield: 49.7%).

Compound 3b (1.0 g, 2.90 mmol) and Pd/C (10%, 100 mg) were added to methanol (15 mL). The reaction mixture was stirred at 60° C. under 1 atmospheric pressure of $H_2$ for 1 hour. The reaction was monitored by TLC for completion. It was concentrated through celite and the filtrate was concentrated under reduce pressure. The residue was purified by $SO_2$ column chromatography ($CH_2Cl_2$:MeOH=20:1) to afford compound 3c (680 mg, yield 74%) as a purple solid. MS m/z 316.2 $[M+H]^+$.

Intermediate 3d was prepared by following the procedure in reference *Journal of Medicinal Chemistry*, 2005, 2371-2387.

Compound 3c (250 mg, 0.79 mmol), compound 3d (264 mg, 0.79 mmol), and toluene (1 mL) in a sealed tube were heated at 100° C. overnight. The reaction was monitored by TLC for completion. It was concentrated under reduced pressure. The residue was purified by $SO_2$ column chromatography ($CH_2Cl_2$:MeOH=20:1) to afford compound 3e (118 mg, yield 25%) as a yellow solid. MS m/z 585.3 $[M+H]^+$.

Compound 3e (118 mg, 0.20 mmol) was dissolved in a mixture of MeOH (5 mL) and water (0.5 mL). Lithium hydroxide monohydrate (43 mg, 1.00 mmol) was added. The reaction mixture was stirred at 60° C. overnight. The reaction was monitored by TLC for completion. It was concentrated under reduced pressure to remove MeOH. Water (5 mL) and EtOAc (10 mL) were added, acidified with aqueous HCl (2 M) to pH=4-5, and extracted with EtOAc (3×10 mL). The combined organic layers were washed with brine, dried over anhydrous sodium sulfate, filtered and concentrated under reduced pressure to afford compound 3f (62 mg, yield 54%) as a yellow solid, which was used in next step. MS m/z 571.3 [M+H]$^+$.

Compound 3f (62 mg, 0.11 mmol), o-(tetrahydro-2H-pyran-2-yl) hydroxylamine (15 mg, 0.13 mmol), HATU (63 mg, 0.17 mmol), and DIEA (43 mg, 0.33 mmol) were dissolved in DMF (2 mL). The reaction mixture was stirred at room temperature for 1 hour. The reaction was monitored by TLC for completion. It was poured into water, and extracted with CH$_2$Cl$_2$ (3×10 mL). The combined organic layers were washed with brine, dried over anhydrous sodium sulfate, and concentrated under reduced pressure. The residue was purified by preparative TLC (CH$_2$Cl$_2$:MeOH=20:1) to afford compound 3g (33 mg, yield 45%) as a yellow solid. MS m/z 670.3 [M+H]$^+$.

Compound 3g (33 mg, 0.05 mmol) was dissolved in THF (1 mL) and a solution of HCl in 1,4-dioxane (4.0 M, 5 drops) was added. The reaction mixture was stirred at room temperature for 2 hours. The reaction was monitored by TLC for completion. It was filtered and the solid was washed with acetonitrile to afford compound 3 (15 mg, yield 52%, hydrochloride salt) as a yellow solid. $^1$H NMR (500 MHz, CD$_3$OD) δ 9.12 (s, 1H), 8.34 (s, 1H), 8.24 (d, J=9.4 Hz, 1H), 8.02 (dd, J=9.7, 3.1 Hz, 1H), 7.75 (s, 1H), 7.50 (d, J=9.7 Hz, 1H), 7.30 (d, J=9.5 Hz, 1H), 6.06-5.95 (m, 1H), 4.01 (t, J=6.1 Hz, 2H), 3.84 (t, J=5.7 Hz, 2H), 3.36 (s, 3H), 3.07 (s, 3H), 2.49 (s, 3H), 2.43 (s, 3H), 2.35-2.26 (m, 2H), 2.14-2.05 (m, 2H), 1.95-1.85 (m, 2H), 1.74-1.64 (m, 2H). MS m/z 586.7 [M+H]$^+$.

Example 4. Preparation of 5-((2-(((6-((6-acetyl-8-cyclopentyl-5-methyl-7-oxo-7,8-dihydropyrido[2,3-d]pyrimidin-2-yl)amino)pyridin-3-yl)(methyl)amino)ethyl)(methyl)amino)-N-hydroxypicolinamide (Compound 4)

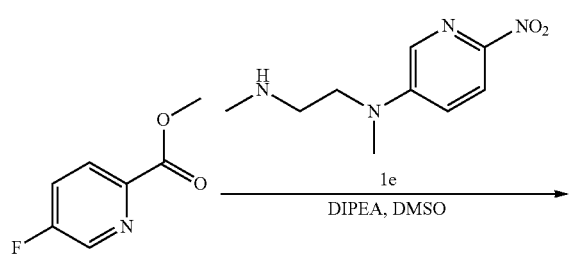

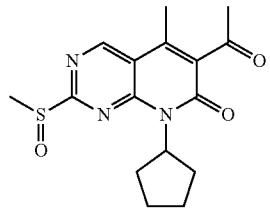

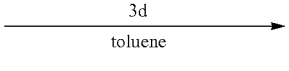

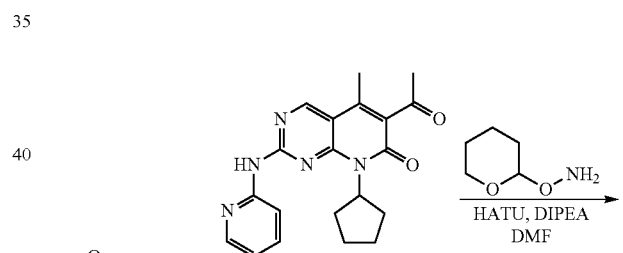

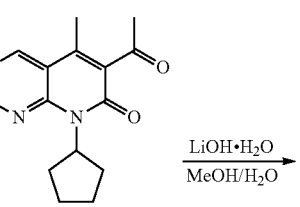

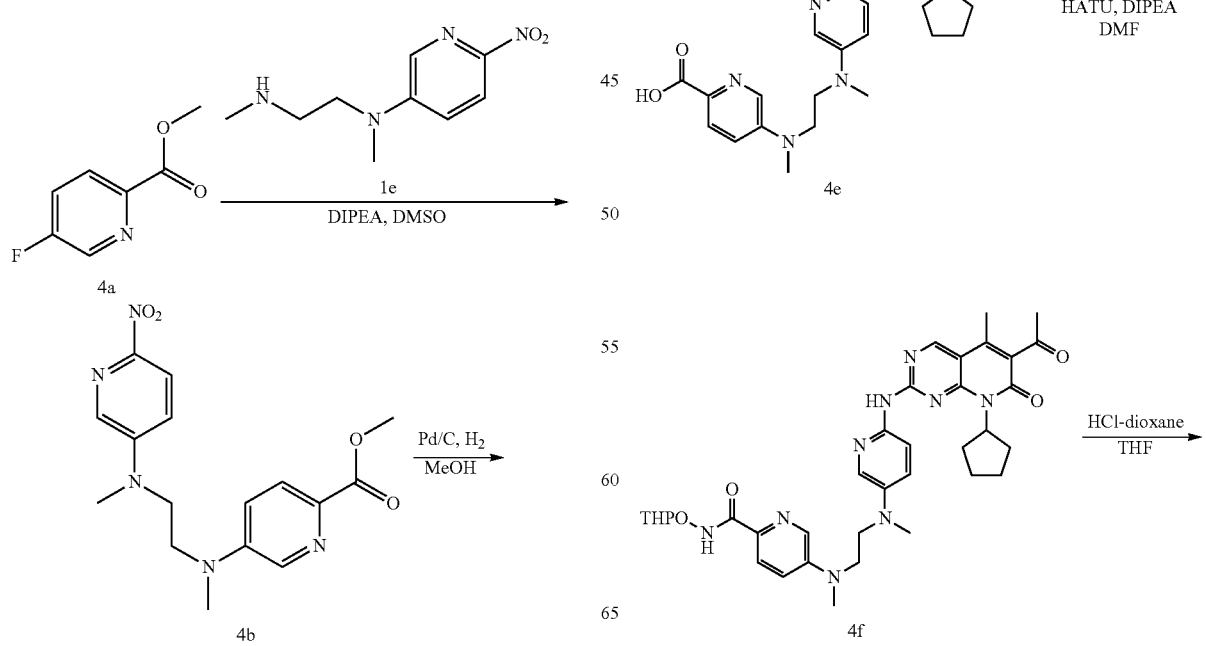

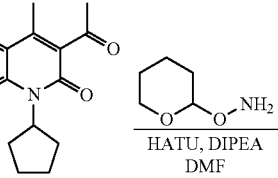

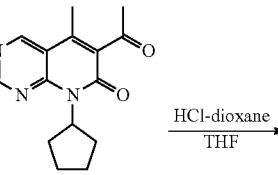

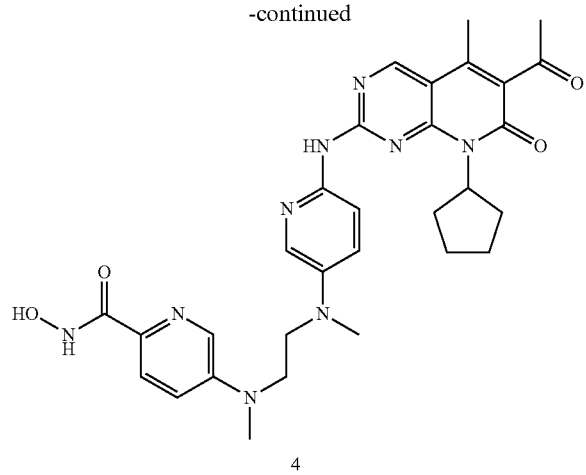

4

Compound 4a (295 mg, 1.90 mmol) and 1e (400 mg, 1.90 mmol) were dissolved in DMSO (5 mL). DIEA (735 mg, 5.70 mmol) was added. The reaction mixture was stirred at 90° C. for 3 hours. The reaction was monitored by TLC for completion. It was poured into water (10 mL), and extracted with EtOAc (3×20 mL). The combined organic layers were washed with brine, dried over anhydrous sodium sulfate, and concentrated under reduced pressure. The residue was purified by $SO_2$ column chromatography ($CH_2Cl_2$:MeOH=20:1) to afford compound 4b (238 mg, yield 36%) as a yellow solid. MS m/z 346.2 $[M+H]^+$.

Compound 4b (238 mg, 0.69 mmol) and Pd/C (10%, 24 mg) were added to MeOH (15 mL). The reaction mixture was stirred at room temperature under 1 atmospheric pressure of $H_2$ for 1 hour. The reaction was monitored by TLC for completion. It was filtered and the filtrate was concentrated under reduced pressure to afford compound 4c (198 mg) as a brown oil. MS m/z 316.2 $[M+H]^+$.

Compound 4c (198 mg, 0.63 mmol), compound 3d (209 mg, 0.63 mmol), and toluene (1 mL) in a sealed tube were stirred at 100° C. overnight. The reaction was monitored by TLC for completion. It was concentrated under reduced pressure. The residue was purified by $SO_2$ column chromatography ($CH_2Cl_2$:MeOH=20:1) to afford compound 4d (89 mg, yield 23%) as a yellow solid. MS m/z 585.3 $[M+H]^+$.

Compound 4d (89 mg, 0.15 mmol) was dissolved in a mixture of MeOH (5 mL) and water (0.5 mL). Lithium hydroxide monohydrate (32 mg, 0.75 mmol) was added. The reaction mixture was stirred at 60° C. overnight. The reaction was monitored by TLC for completion. It was concentrated under reduced pressure to remove MeOH. Water (5 mL) and EtOAc (10 mL) were added, acidified with aqueous HCl (2 M) to pH=4-5, and extracted with EtOAc (3×10 mL). The combined organic layers were washed with brine, dried over anhydrous sodium sulfate, filtered and concentrated under reduced pressure to afford compound 4e (48 mg, yield 55%) as a yellow solid, which was used in next step. MS m/z 571.3 $[M+H]^+$.

Compound 4e (48 mg, 0.08 mmol), o-(tetrahydro-2H-pyran-2-yl)hydroxylamine (11 mg, 0.10 mmol), HATU (46 mg, 0.12 mmol), and DIEA (31 mg, 0.24 mmol) were dissolved in DMF (2 mL). The reaction mixture was stirred at room temperature for 1 hour. The reaction was monitored by TLC for completion. It was poured into ice water, and extracted with $CH_2Cl_2$ (3×10 mL). The combined organic layers were washed with brine, dried over anhydrous sodium sulfate, and concentrated under reduced pressure. The residue was purified by preparative TLC ($CH_2Cl_2$:MeOH=20:1) to afford compound 4f (21 mg, yield 37%) as a yellow solid. MS m/z 670.3 $[M+H]^+$.

Compound 4f (21 mg, 0.03 mmol) was dissolved in THF (1 mL). A solution of HCl in 1,4-dioxane (4.0 M, 2 drops) was added. The reaction mixture was stirred at room temperature for 2 hours. The reaction was monitored by TLC for completion. It was filtered and the solid was washed with acetonitrile to afford compound 4 (7 mg, yield 38%, hydrochloride salt) as a yellow solid. $^1H$ NMR (500 MHz, $CD_3OD$) δ 9.10 (s, 1H), 8.07-8.00 (m, 2H), 7.95 (dd, J=9.9, 2.9 Hz, 1H), 7.71-7.64 (m, 2H), 7.47 (d, J=9.5 Hz, 1H), 6.04-5.96 (m, 1H), 3.86 (t, J=5.5 Hz, 2H), 3.80 (t, J=5.5 Hz, 2H), 3.17 (s, 3H), 3.04 (s, 3H), 2.49 (s, 3H), 2.43 (s, 3H), 2.35-2.27 (m, 2H), 2.13-2.06 (m, 2H), 1.93-1.86 (m, 2H), 1.73-1.65 (m, 2H). MS m/z 586.6 $[M+H]^+$.

Example 5. Preparation of 6-((2-((6-((6-acetyl-8-cyclopentyl-5-methyl-7-oxo-7,8-dihydropyrido[2,3-d]pyrimidin-2-yl)amino)pyridin-3-yl)oxy)ethyl)(methyl)amino)-N-hydroxynicotinamide (Compound 5)

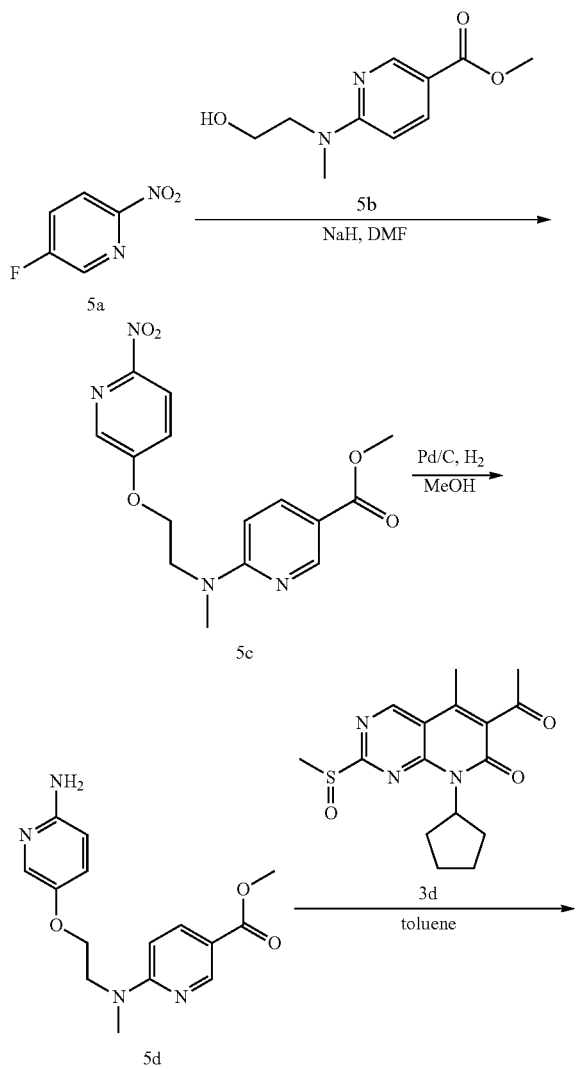

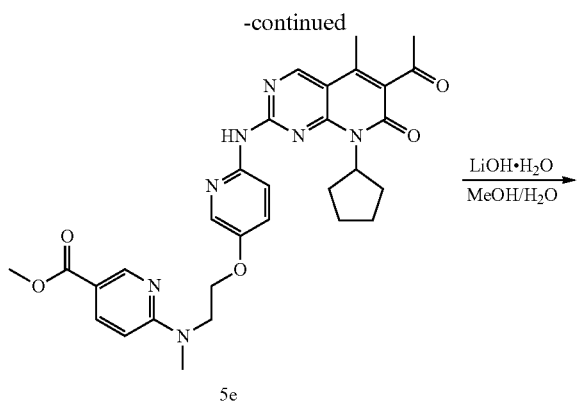

5e

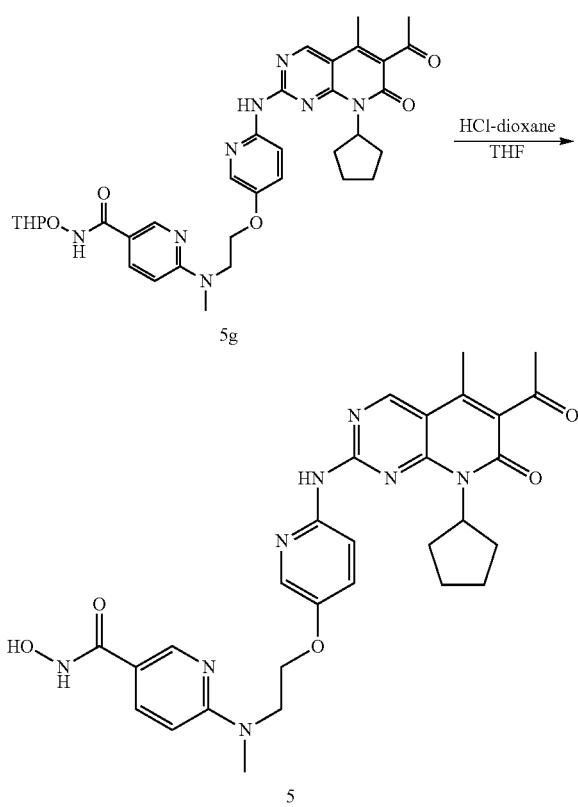

5f

5g

5

Compound 5a (676 g, 4.76 mmol) and compound 5b (1.0 g, 4.76 mmol) were dissolved in DMF (10 mL). NaH (60%, 381 mg, 9.52 mmol) was added at 0° C. The reaction mixture was stirred at 0° C. for 0.5 hour. The reaction was monitored by TLC for completion. Saturated aqueous $NH_4Cl$ (15 mL) was added, and the mixture was extracted with EtOAc (3×20 mL). The combined organic layers were washed with brine, dried over anhydrous sodium sulfate, filtered and concentrated under reduced pressure. The residue was purified by $SO_2$ column chromatography ($CH_2Cl_2$:MeOH=20:1) to afford compound 5c (1.1 g, yield 70%) as a yellow solid. MS m/z 333.1 $[M+H]^+$.

Compound 5c (500 mg, 1.50 mmol) and Pd/C (10%, 50 mg) were added to MeOH (15 mL). The reaction mixture was stirred at room temperature under 1 atmospheric pressure of $H_2$ for 1 hour. The reaction was monitored by TLC for completion. It was filtered and the filtrate was concentrated under reduced pressure to afford compound 5d (438 mg, yield 96%) as a brown oil. MS m/z 303.2 $[M+H]^+$.

Compound 5d (250 mg, 0.83 mmol), compound 3d (276 mg, 0.83 mmol), and toluene (1 mL) in a sealed tube were stirred at 100° C. overnight. The reaction was monitored by TLC for completion. It was concentrated under reduced pressure to remove the solvent. The residue was purified by $SO_2$ column chromatography ($CH_2Cl_2$:MeOH=20:1) to afford compound 5e (101 mg, yield 21%) as a yellow solid. MS m/z 572.3 $[M+H]^+$.

Compound 5e (101 mg, 0.18 mmol) was dissolved in a mixture of MeOH (5 mL) and water (0.5 mL). Lithium hydroxide monohydrate (39 mg, 0.90 mmol) was added. The reaction mixture was stirred at 60° C. overnight. The reaction was monitored by TLC for completion. It was concentrated under reduced pressure. Water (5 mL) and EtOAc (10 mL) were added, acidified with aqueous HCl (2 M) to pH=4-5, and extracted with EtOAc (3×10 mL). The combined organic layers were washed with brine, dried over anhydrous sodium sulfate, filtered and concentrated under reduced pressure to afford compound 5f (48 mg, yield 49%) as a yellow solid, which was used in next step. MS m/z 558.4 $[M+H]^+$.

Compound 5f (48 mg, 0.09 mmol), o-(tetrahydro-2H-pyran-2-yl)hydroxylamine (12 mg, 0.10 mmol), HATU (51 mg, 0.14 mmol), and DIEA (36 mg, 0.28 mmol) were dissolved in DMF (2 mL). The reaction mixture was stirred at room temperature for 1 hour. The reaction was monitored by TLC for completion. It was poured into ice water, and extracted with $CH_2Cl_2$ (3×10 mL). The combined organic layers were washed with brine, dried over anhydrous sodium sulfate, and concentrated under reduced pressure. The residue was purified by preparative TLC ($CH_2Cl_2$:MeOH=20:1) to afford compound 5g (26 mg, yield 46%) as a yellow solid. MS m/z 657.3 $[M+H]^+$.

Compound 5g (26 mg, 0.04 mmol) was dissolved in THF (1 mL). A solution of HCl in 1,4-dioxane (4.0 M, 2 drops) was added. The reaction mixture was stirred at room temperature for 2 hours. The reaction was monitored by TLC for completion. It was filtered and the solid was washed with acetonitrile to afford compound 5 (7 mg, yield 30%, hydrochloride salt) as a yellow solid. $^1H$ NMR (500 MHz, $CD_3OD$) δ 9.10 (s, 1H), 8.39 (s, 1H), 8.25 (d, J=9.7 Hz, 1H), 8.10 (d, J=2.9 Hz, 1H), 8.00 (dd, J=9.5, 2.9 Hz, 1H), 7.55 (d, J=9.5 Hz, 1H), 7.41 (d, J=9.5 Hz, 1H), 6.03-5.95 (m, 1H), 4.48 (t, J=5.1 Hz, 2H), 4.22 (t, J=5.0 Hz, 2H), 3.42 (s, 3H), 2.49 (s, 3H), 2.42 (s, 3H), 2.34-2.26 (m, 2H), 2.12-2.06 (m, 2H), 1.93-1.86 (m, 2H), 1.72-1.65 (m, 2H). MS m/z 573.6 $[M+H]^+$.

Example 6. Preparation of (E)-3-(6-((6-acetyl-8-cyclopentyl-5-methyl-7-oxo-7,8-dihydropyrido[2,3-d]pyrimidin-2-yl) amino) pyridin-3-yl)-N-hydroxy-acrylamide (Compound 6)

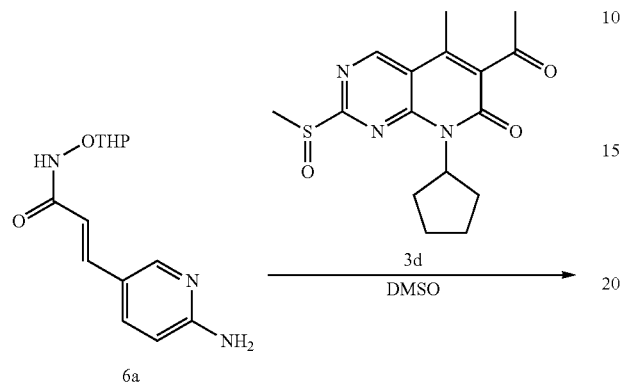

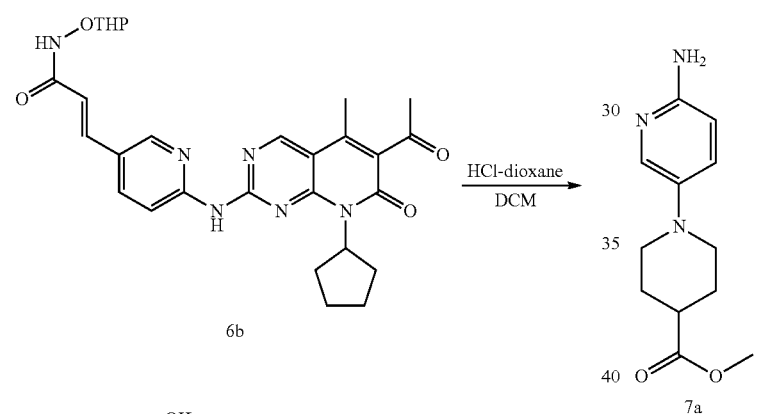

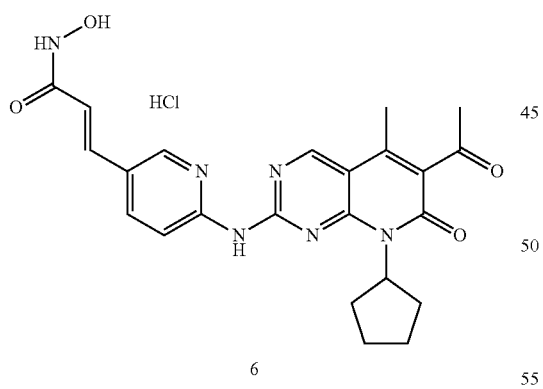

Compound 6a (50 mg, 0.15 mmol) and compound 3d (79 mg, 0.30 mmol) were dissolved in DMSO (1 mL). The reaction mixture was stirred at 75° C. overnight. Some of starting material was found by TLC. After cooling to room temperature, it was concentrated under reduce pressure to afford crude product, which was purified by SO$_2$ column chromatography (CH$_2$Cl$_2$:EtOAc=3:2) to afford compound 6b (8 mg, yield 11%) as a yellow solid. MS m/z 533.6 [M+H]$^+$.

Compound 6b (8 mg, 0.02 mmol) was dissolved in CH$_2$Cl$_2$ (1.5 mL) followed by the addition of a solution of HCl in 1,4-dioxane (4.0 M, 4 drops). The reaction mixture was stirred at room temperature for 30 mins. The reaction was monitored by TLC. It was filtered and the solid was washed with Et$_2$O to afford compound 6 (15 mg, yield 100%, hydrochloride salt) as a yellow solid. $^1$H NMR (500 MHz, DMSO-d$_6$) δ 9.25 (s, 1H), 8.49 (bs, 2H), 8.36-8.29 (m, 2H), 7.61 (d, J=15.7 Hz, 1H), 7.30 (d, J=15.7 Hz, 1H), 7.02 (d, J=9.3 Hz, 1H), 5.72-5.64 (m, 1H), 2.45 (s, 3H), 2.39 (s, 3H), 2.22-2.12 (m, 2H), 1.90-1.80 (m, 2H), 1.72-1.63 (m, 2H), 1.42-1.32 (m, 2H). MS m/z 449.5 [M+H]$^+$.

Example 7. Preparation of 1-(6-((6-acetyl-8-cyclopentyl-5-methyl-7-oxo-7,8-dihydropyrido[2,3-d]pyrimidin-2-yl) amino) pyridin-3-yl)-N-hydroxypiperidine-4-carboxamide (Compound 7)

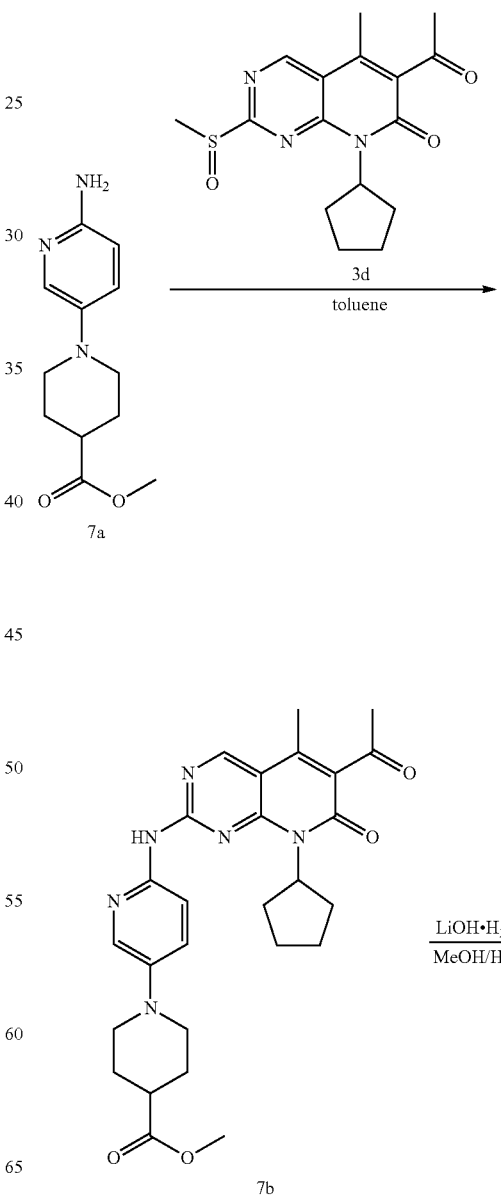

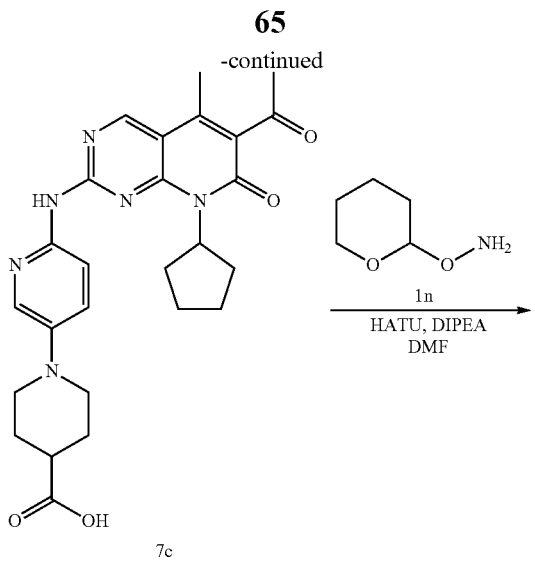

A mixture of compound 7a (169 mg, 0.72 mmol), compound 3d (120 mg, 0.36 mmol), and toluene (4 mL) in a sealed tube was stirred at 100° C. overnight. The reaction was monitored by TLC. It was concentrated under reduced pressure to give crude product, which was purified by SO$_2$ column chromatography (CH$_2$Cl$_2$:MeOH=20:10) to afford compound 7b (50 mg, yield 27%) as a yellow solid.

Compound 7b (40 mg, 0.08 mmol) was dissolved in a mixture of methanol (5 mL) and water (0.5 mL). Lithium hydroxide hydrate (17 mg, 0.40 mmol) was added. The reaction mixture was stirred at 60° C. overnight. The reaction was monitored by TLC. After cooling to room temperature, it was acidified with a solution of HCl in methanol (4.0 M) to pH=3-4, and concentrated under reduced pressure to afford compound 7c (39 mg) as a yellow solid, which was used in next step. MS m/z 491.2 [M+H]$^+$.

Compound 7c (39 mg, 0.08 mmol), o-(tetrahydro-2H-pyran-2-yl) hydroxylamine (11 mg, 0.10 mmol), HATU (46 mg, 0.12 mmol), and DIEA (31 mg, 0.24 mmol) were dissolved in DMF (2 mL). The reaction mixture was stirred at room temperature for 1 hour. The reaction was monitored by TLC. It was poured into water, and extracted with CH$_2$Cl$_2$ (3×10 mL). The combined organic layers were washed with brine, dried over anhydrous sodium sulfate, filtered and concentrated under reduced pressure. The residue was purified by preparative TLC (CH$_2$Cl$_2$:MeOH=20:1) to give compound 7d (27 mg, yield of two steps 58%) as a yellow solid. MS m/z 590.4 [M+H]$^+$.

Compound 7d (27 mg, 0.05 mmol) was dissolved in THF (2 mL) followed by the addition of a solution of HCl in 1,4-dioxane (4.0 M, 3 drops). The reaction mixture was stirred at room temperature for 2 hours. The reaction was monitored by TLC. It was filtered and the solid was washed with acetonitrile to afford compound 7 (14 mg, yield 61%, hydrochloride salt) as a yellow solid. $^1$H NMR (500 MHz, CD$_3$OD) δ 9.10 (s, 1H), 8.19 (dd, J=9.7, 3.0 Hz, 1H), 7.85 (d, J=3.0 Hz, 1H), 7.50 (d, J=9.6 Hz, 1H), 6.05-5.96 (m, 1H), 3.87-3.80 (m, 2H), 2.97-2.88 (m, 2H), 2.49 (s, 3H), 2.43 (s, 3H), 2.37-2.27 (m, 3H), 2.13-2.06 (m, 2H), 1.96-1.83 (m, 6H), 1.73-1.65 (m, 2H). MS m/z 506.4 [M+H]$^+$.

Example 8. Preparation of 4-((2-((6-(((6-acetyl-8-cyclopentyl-5-methyl-7-oxo-7,8-dihydropyrido[2,3-d]pyrimidin-2-yl) amino) pyridin-3-yl) (methyl) amino) ethyl) (methyl) amino)-N-hydroxybenzamide (Compound 8)

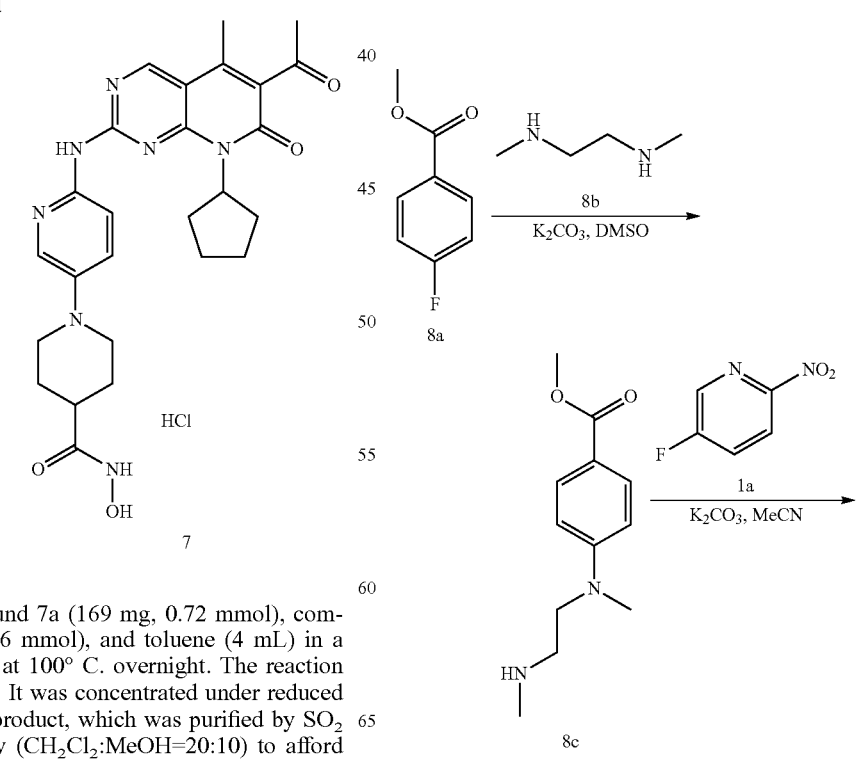

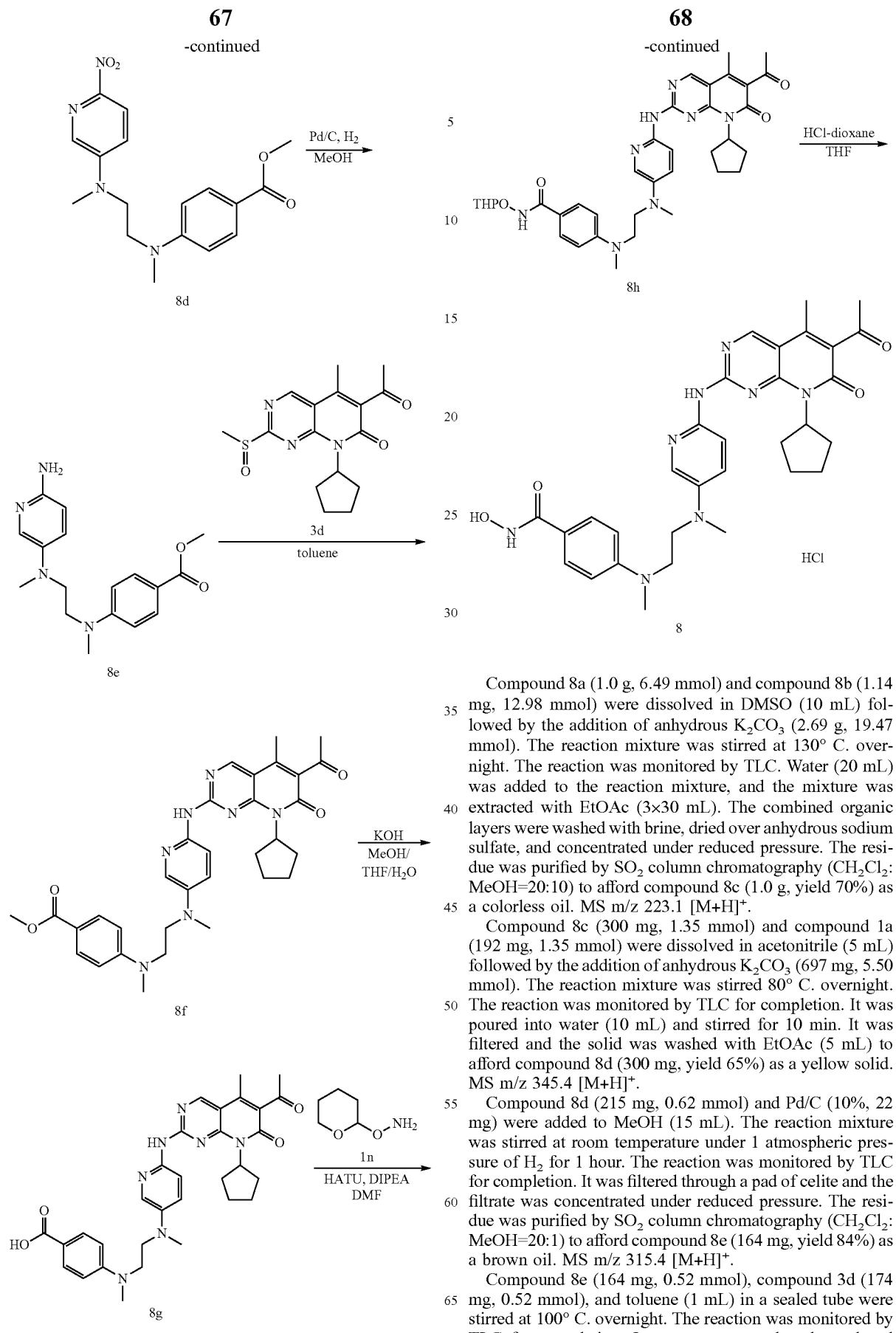

Compound 8a (1.0 g, 6.49 mmol) and compound 8b (1.14 mg, 12.98 mmol) were dissolved in DMSO (10 mL) followed by the addition of anhydrous $K_2CO_3$ (2.69 g, 19.47 mmol). The reaction mixture was stirred at 130° C. overnight. The reaction was monitored by TLC. Water (20 mL) was added to the reaction mixture, and the mixture was extracted with EtOAc (3×30 mL). The combined organic layers were washed with brine, dried over anhydrous sodium sulfate, and concentrated under reduced pressure. The residue was purified by $SO_2$ column chromatography ($CH_2Cl_2$: MeOH=20:10) to afford compound 8c (1.0 g, yield 70%) as a colorless oil. MS m/z 223.1 $[M+H]^+$.

Compound 8c (300 mg, 1.35 mmol) and compound 1a (192 mg, 1.35 mmol) were dissolved in acetonitrile (5 mL) followed by the addition of anhydrous $K_2CO_3$ (697 mg, 5.50 mmol). The reaction mixture was stirred 80° C. overnight. The reaction was monitored by TLC for completion. It was poured into water (10 mL) and stirred for 10 min. It was filtered and the solid was washed with EtOAc (5 mL) to afford compound 8d (300 mg, yield 65%) as a yellow solid. MS m/z 345.4 $[M+H]^+$.

Compound 8d (215 mg, 0.62 mmol) and Pd/C (10%, 22 mg) were added to MeOH (15 mL). The reaction mixture was stirred at room temperature under 1 atmospheric pressure of $H_2$ for 1 hour. The reaction was monitored by TLC for completion. It was filtered through a pad of celite and the filtrate was concentrated under reduced pressure. The residue was purified by $SO_2$ column chromatography ($CH_2Cl_2$: MeOH=20:1) to afford compound 8e (164 mg, yield 84%) as a brown oil. MS m/z 315.4 $[M+H]^+$.

Compound 8e (164 mg, 0.52 mmol), compound 3d (174 mg, 0.52 mmol), and toluene (1 mL) in a sealed tube were stirred at 100° C. overnight. The reaction was monitored by TLC for completion. It was concentrated under reduced pressure to remove solvent. The residue was purified by SO₂ column chromatography (CH₂Cl₂:MeOH=20:1) compound 8f (74 mg, yield 24%) as a yellow solid. MS m/z 584.7 [M+H]⁺.

Compound 8f (74 mg, 0.13 mmol) was dissolved in a mixture of MeOH (3 mL), THF (3 mL) and water (0.5 mL). KOH (36 mg, 0.65 mmol) was added. The reaction mixture was stirred at 70° C. overnight. The reaction was monitored by TLC for completion. It was concentrated under reduced pressure. Water (5 mL) and EtOAc (10 mL) were added, acidified with aqueous HCl (2 M) to pH=4-5, and extracted with EtOAc (3×10 mL). The combined organic layers were washed with brine, dried over anhydrous sodium sulfate, filtered and concentrated under reduced pressure to afford compound 8g (41 mg, yield 57%) as a yellow solid, which was used in next step. MS m/z 570.7 [M+H]⁺.

Compound 8g (41 mg, 0.07 mmol), o-(tetrahydro-2H-pyran-2-yl) hydroxylamine (10 mg, 0.09 mmol), HATU (40 mg, 0.11 mmol), and DIEA (27 mg, 0.21 mmol) were dissolved in DMF (2 mL). The reaction mixture was stirred at room temperature for 1 hour. The reaction was monitored by TLC for completion. It was poured into ice water and extracted with CH₂Cl₂ (3×10 mL). The combined organic layers were washed with brine, dried over anhydrous sodium sulfate, filtered and concentrated under reduced pressure. The residue was purified by preparative TLC (CH₂Cl₂:MeOH=20:1) to afford compound 8h (10 mg, yield 21%) as a yellow solid. MS m/z 669.5 [M+H]⁺.

Compound 8h (10 mg, 0.01 mmol) was dissolved in THF (1 mL). A solution of HCl in 1,4-dioxane (4.0 M, 2 drops) was added slowly. The reaction mixture was stirred at room temperature for 2 hours. The reaction was monitored by TLC for completion. It was filtered and the solid was washed with acetonitrile to afford compound 8 (3 mg, yield 30%, hydrochloride salt) as a yellow solid. ¹H NMR (500 MHz, CD₃OD) δ 9.06 (s, 1H), 7.82 (dd, J=9.7, 3.1 Hz, 1H), 7.56 (d, J=9.0 Hz, 2H), 7.43 (d, J=3.1 Hz, 1H), 7.33 (d, J=9.6 Hz, 1H), 6.65 (d, J=8.9 Hz, 2H), 6.05-5.95 (m, 1H), 3.74 (s, 4H), 3.00 (s, 3H), 2.97 (s, 3H), 2.49 (s, 3H), 2.44 (s, 3H), 2.35-2.27 (m, 2H), 2.13-2.06 (m, 2H), 1.93-1.85 (m, 2H), 1.72-1.66 (m, 2H). MS m/z 585.7 [M+H]⁺.

Example 9. Preparation of 7-((6-(((6-acetyl-8-cyclopentyl-5-methyl-7-oxo-7,8-dihydropyrido[2,3-d]pyrimidin-2-yl)amino)pyridin-3-yl)(methyl)amino)-N-hydroxyheptanamide (Compound 9)

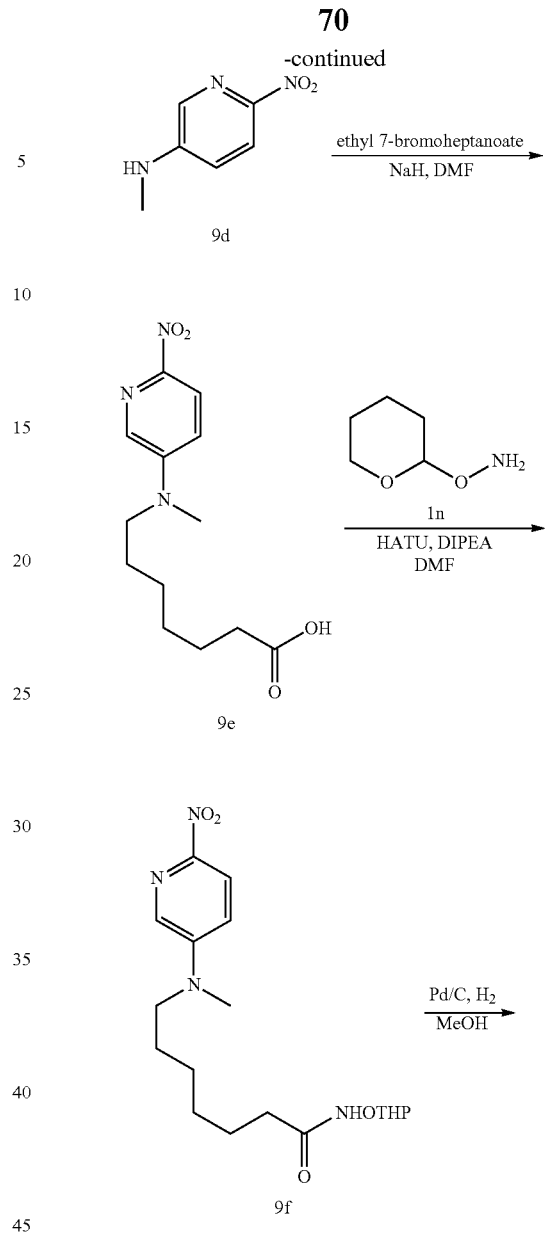

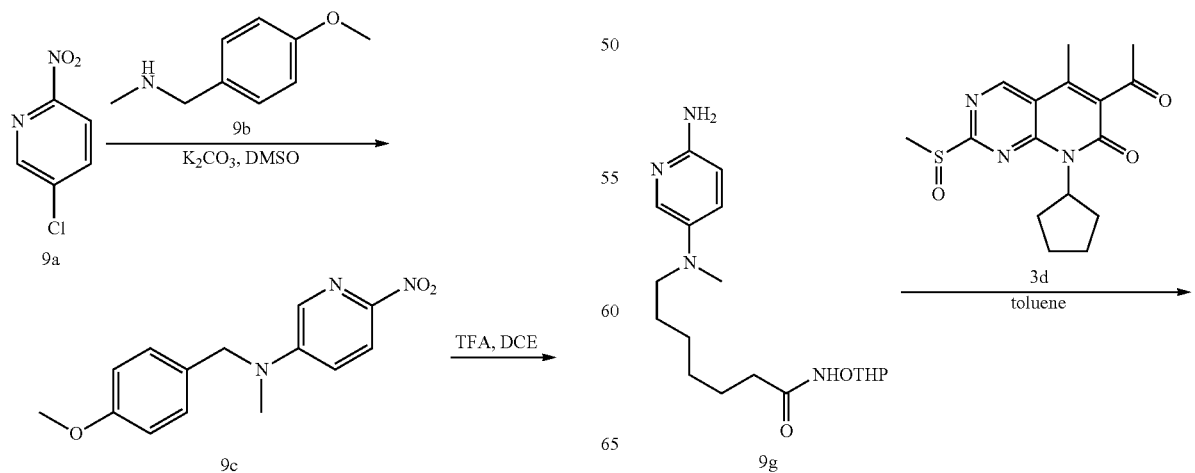

-continued

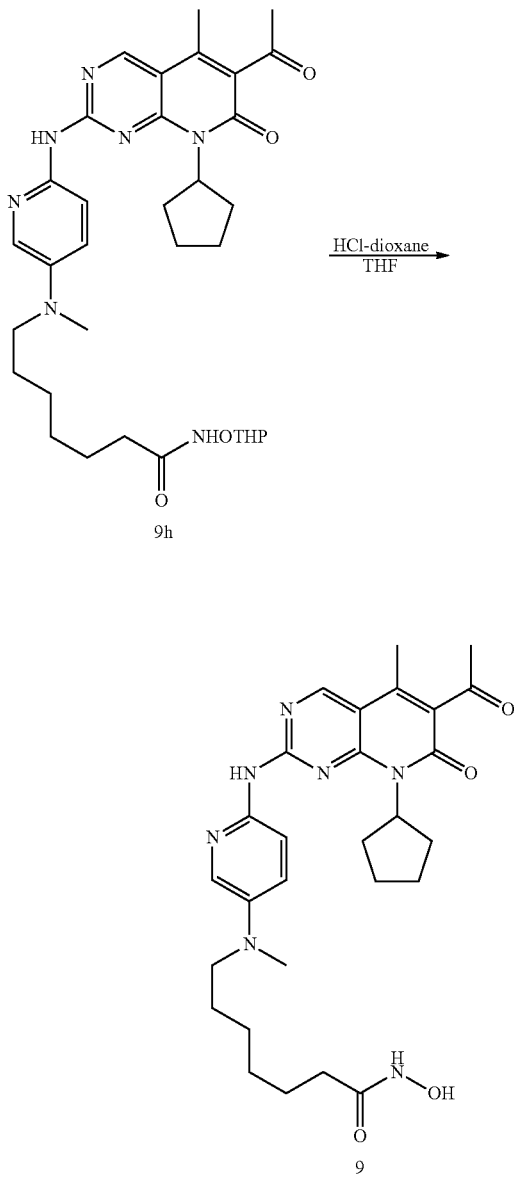

Compound 9a (10.00 g, 63.29 mmol) and compound 9b (9.54 g, 63.29 mmol) were dissolved in DMSO (50 mL). Anhydrous $K_2CO_3$ (26.00 g, 188.41 mmol) was added. The reaction mixture was stirred at 120° C. overnight. The reaction was monitored by TLC for completion. It was filtered. The filtrated was poured into water (100 mL) and extracted with EtOAc (3×150 mL). The combined organic layers were washed with brine, dried over anhydrous sodium sulfate, filtered and concentrated under reduced pressure. The residue was stirred in EtOAc (20 ml) and filtered to afford compound 9c (8.47 g, yield 49%) as a yellow solid. MS m/z 274.3 $[M+H]^+$.

Compound 9c (8.00 g, 29.27 mmol) was dissolved in 1,2-dichloroethane (30 mL). TFA (20 mL) was added and the reaction mixture was stirred at room temperature for 1 hour. The reaction was monitored by TLC for completion. It was concentrated under reduced pressure. Water (20 mL) and EtOAc (30 mL) were added. It was neutralized with aqueous NaOH (1 M) to pH=7-8, and extracted with EtOAc (3×50 mL). The combined organic layers were washed with brine, dried over anhydrous sodium sulfate, filtered and concentrated under reduced pressure. The residue was stirred in EtOAc (10 ml) and filtered to afford compound 9d (4.84 g) as a yellow solid. MS m/z 154.3 $[M+H]^+$.

Compound 9d (200 mg, 1.31 mmol), and ethyl 7-bromo-heptanoate (310 mg, 1.31 mmol) were dissolved in DMF (5 mL). NaH (60%, 157 mg, 3.93 mmol) was added at 0° C. The reaction mixture as stirred at room temperature for 2 hours. The reaction was monitored by TLC for completion. It was poured into water (20 mL), and stirred at room temperature for 0.5 hour. It was acidified with aqueous HCl (2 M) to pH=4-5, and extracted with EtOAc (3×20 mL). The combined organic layers were washed with brine, dried over anhydrous sodium sulfate, filtered and concentrated under reduced pressure to afford compound 9e (140 mg, yield 38%) as a yellow solid. MS m/z 282.2 $[M+H]^+$.

Compound 9e (140 mg, 0.50 mmol), o-(tetrahydro-2H-pyran-2-yl) hydroxylamine (84 mg, 0.72 mmol), HATU (285 mg, 0.75 mmol), and DIEA (194 mg, 1.50 mmol) were dissolved in DMF (5 mL). The reaction mixture was stirred at room temperature for 1 hour. The reaction was monitored by TLC for completion. It was poured into ice water, and extracted with $CH_2Cl_2$ (3×20 mL). The combined organic layers were washed with brine, dried over anhydrous sodium sulfate, filtered and concentrated under reduced pressure. The residue was purified by preparative TLC ($CH_2Cl_2$: MeOH=20:1) to afford compound 9f (118 mg, yield 62%) as a yellow solid. MS m/z 381.4 $[M+H]^+$.

Compound 9f (118 mg, 0.31 mmol) and Pd/C (10%, 20 mg) were added to MeOH (15 mL) at room temperature. The reaction mixture was stirred at room temperature under 1 atmospheric pressure of $H_2$ for 1 hour. The reaction was monitored by TLC for completion. It was filtered through celite and the filtrate was concentrated under reduced pressure. The residue was purified by $SO_2$ column chromatography ($CH_2Cl_2$:MeOH=20:1) to afford compound 9g (88 mg, yield 81%) as a brown oil. MS m/z 351.2 $[M+H]^+$.

Compound 9g (88 mg, 0.25 mmol), compound 3d (84 mg, 0.25 mmol), and toluene (1 mL) in a sealed tube were stirred at 100° C. overnight. The reaction was monitored by TLC for completion. It was concentrated under reduced pressure and the residue was purified by $SO_2$ column chromatography ($CH_2Cl_2$:MeOH=20:1) to afford compound 9h (17 mg, yield 11%) as a yellow solid. MS m/z 620.3 $[M+H]^+$.

Compound 9h (17 mg, 0.03 mmol) was dissolved in THF (1 mL). A solution of HCl in 1,4-dioxane (4.0 M, 3 drops) was added slowly. The reaction mixture was stirred at room temperature for 2 hours. The reaction was monitored by TLC for completion. It was filtered and the solid was washed with acetonitrile to afford compound 9 (5 mg, yield 33%, hydrochloride salt) as a yellow solid. $^1H$ NMR (500 MHz, $CD_3OD$) δ 9.09 (s, 1H), 7.95 (dd, J=9.7, 3.1 Hz, 1H), 7.64 (d, J=3.1 Hz, 1H), 7.48 (d, J=9.6 Hz, 1H), 6.04-5.95 (m, 1H), 3.44 (t, J=7.4 Hz, 2H), 3.04 (s, 3H), 2.49 (s, 3H), 2.42 (s, 3H), 2.35-2.27 (m, 2H), 2.14-2.04 (m, 4H), 1.94-1.87 (m, 2H), 1.72-1.66 (m, 2H), 1.66-1.58 (m, 4H), 1.44-1.36 (m, 4H). MS m/z 536.7 $[M+H]^+$.

Example 10. Preparation of 2-((2-((6-(((6-acetyl-8-cyclopentyl-5-methyl-7-oxo-7,8-dihydropyrido[2,3-d]pyrimidin-2-yl)amino)pyridin-3-yl)oxy)ethyl)(methyl)amino)-N-hydroxypyrimidine-5-carboxamide (Compound 10)

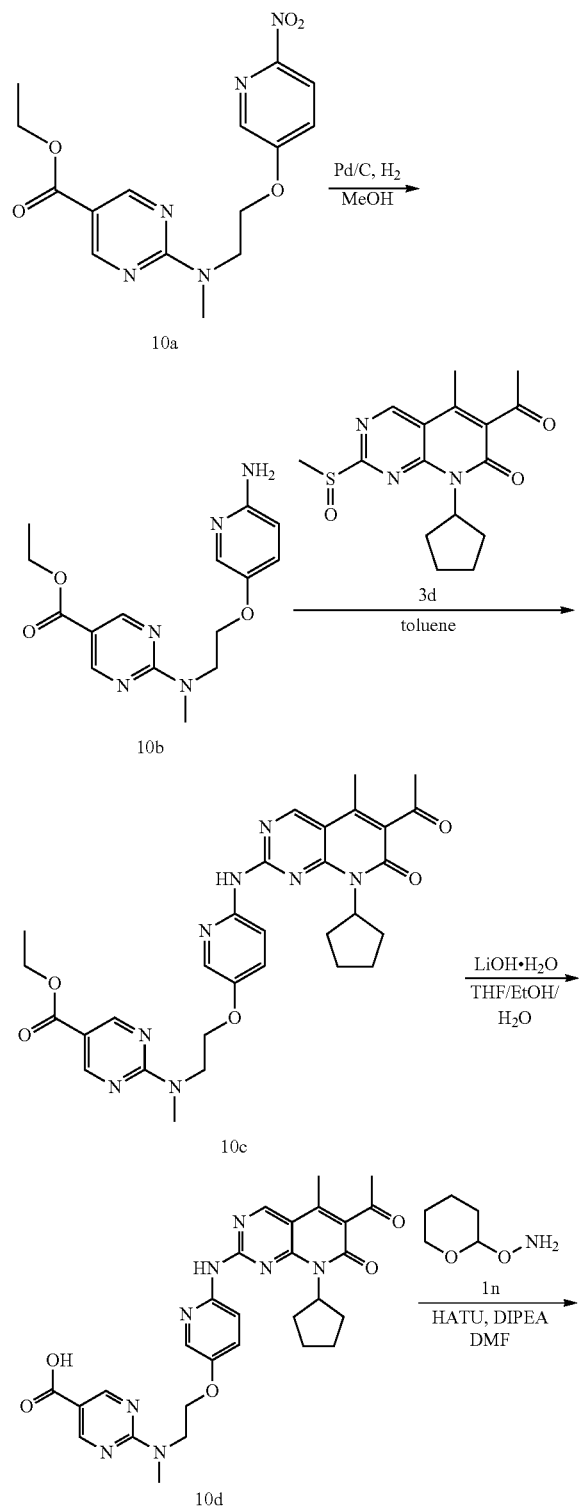

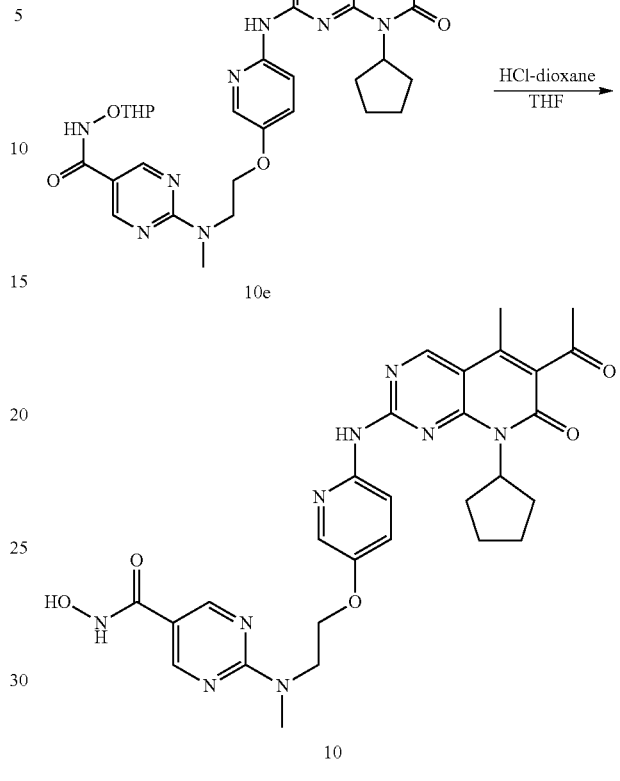

Compound 10a (300 mg, 0.86 mmol) and Pd/C (10%, 100 mg) were added to MeOH (12 mL) at room temperature. The reaction mixture was stirred at room temperature under 1 atmospheric pressure of $H_2$ for 1 hour. The reaction was monitored by TLC for completion. It was filtered through celite and the filtrate was concentrated under reduced pressure. The residue was purified by $SO_2$ column chromatography ($CH_2Cl_2$:MeOH=20:1) to afford compound 10b (198 mg, yield 72%) as a yellow solid. MS m/z 318.3 $[M+H]^+$.

Compound 10b (198 mg, 0.62 mmol) and compound 3d (207 mg, 0.62 mmol) were dissolved in toluene (3 mL). The reaction mixture was stirred at 100° C. overnight. Some of starting material was found by TLC. After cooling to room temperature, it was concentrated under reduced pressure. The residue was purified by $SO_2$ column chromatography ($CH_2Cl_2$:EtOAc=2:1, 2% aqueous ammonium hydroxide solution) to afford compound 10c (52 mg, yield 14%) as a yellow solid. MS m/z 587.7 $[M+H]^+$.

Compound 10c (52 mg, 0.09 mmol) was dissolved in a mixture of THF (5 mL), EtOH (2 mL) and water (1 mL). Lithium hydroxide hydrate (37 mg, 0.89 mmol) was added. The reaction mixture was stirred at 60° C. for 2 hours. The reaction was monitored by TLC. After the cooling to room temperature, it was acidified with a solution of HCl in methanol (4.0 M) to pH=3-4, and concentrated under reduced pressure. The residue was purified by $SO_2$ column chromatography ($CH_2Cl_2$:MeOH=20:1) to afford compound 10d (82 mg) as a yellow solid, which was used in next step. MS m/z 559.7 $[M+H]^+$.

Compound 10d (82 mg, 0.15 mmol), o-(tetrahydro-2H-pyran-2-yl) hydroxylamine (21 mg, 0.18 mmol), HATU (86 mg, 0.23 mmol), and DIEA (57 mg, 0.44 mmol) were dissolved in DMF (3 mL). The reaction mixture was stirred at room temperature for 1 hour. The reaction was monitored by TLC for completion. The reaction mixture was concentrated under reduced pressure. The residue was purified by SO$_2$ column chromatography (CH$_2$Cl$_2$:MeOH=20:1) to afford compound 10e (48 mg, yield of two steps 82%) as a yellow solid. MS m/z 658.8 [M+H]$^+$.

Compound 10e (48 mg, 0.07 mmol) was dissolved in THF (3 mL). A solution of HCl in 1,4-dioxane (4.0 M, 6 drops) was added slowly. The reaction mixture was stirred at room temperature for 2 hours. The reaction was monitored by TLC for completion. It was filtered and the solid was washed with THF to afford compound 10 (30 mg, yield 67%, hydrochloride salt) as a yellow solid. $^1$H NMR (500 MHz, CD$_3$OD) δ 9.10 (s, 1H), 8.70 (s, 2H), 8.10-8.01 (m, 2H), 7.53 (d, J=9.4 Hz, 1H), 6.07-5.94 (m, 1H), 4.43 (t, J=5.3 Hz, 2H), 4.17 (t, J=5.4 Hz, 2H), 3.00 (s, 3H), 2.49 (s, 3H), 2.43 (s, 3H), 2.36-2.26 (m, 2H), 2.14-2.06 (m, 2H), 1.95-1.88 (m, 2H), 1.74-1.65 (m, 2H). MS m/z 574.6 [M+H]$^+$.

Example 11. Biology Assays

1. CDK2, CDK4 and CDK6 Kinase Assays
    Method 1: In vitro enzymatic activity of the CDK isoforms CDK2/CycA2, CDK4/CycD3 and CDK6/cycD3 were measured using Mobility Shift Assay that monitors phosphorylation ratio of FAM labelled peptide (Peptide 18 for CDK2/CycA2, Peptide 8 for CDK4/CycD3). CDK2/CycA2 and CDK6/CycD3 were assayed under buffer conditions in the presence of 50 mM HEPES (pH 7.5), 10 mM MgCl$_2$, 0.0015% Brij-35 and 2 mM dithiothreitol; CDK4/CycD3 with buffer condition of 20 mM HEPES (pH 7.5), 10 mM MgCl$_2$, 0.01% Triton X-100 and 2 mM dithiothreitol. Prepare compounds to 50× of the final desired highest inhibitor concentration by 100% DMSO and serial dilution in 3-fold for total of 10 concentrations. For each isoform, dosage of enzyme and substrate are CDK2/CycA2 12 nM, ATP Km 39 μM; CDK4/CycD3 10 nM, ATP Km 221 μM; CDK6/cycD3 15 nM, ATP Km 800 μM. After assay for 60 min, 180 min, 60 min respectively at 28° C., reactions were terminated with stop solution (50 mM EDTA, 0.015% Brij-35, 0.2% Coating Reagent #3 and 100 mM HEPES (pH 7.5)). Collect conversion on Caliper EZ Reader. IC$_{50}$ values were calculated by fitting the dose-response curves with Xlfit excel add-in version 4.3.1.
    Method 2: In vitro enzymatic activity of the CDK isoforms CDK2/CycA2, CDK4/CycD3 and CDK6/CycD3 were measured using Mobility Shift Assay that monitors phosphorylation ratio of FAM labelled peptide (Peptide 18 for CDK2/CycA2, Peptide 8 for CDK4/CycD3 and CDK6/CycD3). CDK2/CycA2, CDK4/CycD3 and CDK6/cycD3 were assayed under buffer conditions in the presence of 50 mM HEPES (pH 7.5), 10 mM MgCl$_2$, 0.0015% Brij-35 and 2 mM dithiothreitol. Prepare compounds to 100× of the final desired highest inhibitor concentration by 100% DMSO and serial dilution in 3-fold for total of 10 concentrations, each concentration contains 1% DMSO. For each isoform, dosage of enzyme and substrate are CDK2/CycA2 2.5 nM, ATP Km 17 μM; CDK4/CycD3 10 nM, ATP Km 250 μM; CDK6/cycD3 5 nM, ATP Km 550 μM. After assay for 30 min, 150 min, 150 min respectively at 28° C., reactions were terminated with stop solution (50 mM EDTA, 0.015% Brij-35, 0.2% Coating Reagent #3 and 100 mM HEPES (pH 7.5)). Collect conversion on Caliper EZ Reader. IC$_{50}$ values were calculated by fitting the dose-response curves with GraphPad Prism V5.0.

The testing results of the representative compounds are listed in Table 1 below.

TABLE 1

| CDK2, CDK4 and CDK6 assays | | | |
|---|---|---|---|
| Compounds | CDK4 (IC$_{50}$, nM) | CDK6 (IC$_{50}$, nM) | CDK2 (IC$_{50}$, nM) |
| 1 | ≤10 | >25 and ≤50 | >10000 |
| 2 | >10 and ≤25 | >50 and ≤100 | >2000 |
| 3 | >10 and ≤25 | >25 and ≤50 | >2000 |
| 4 | ≤10 | >25 and ≤50 | >5000 |
| 5 | ≤10 | >25 and ≤50 | >2000 |
| 7 | ≤10 | >25 and ≤50 | >2000 |
| 8 | ≤10 | >25 and ≤50 | >5000 |
| 9 | >10 and ≤25 | >25 and ≤50 | >5000 |
| 10 | >10 and ≤25 | >25 and ≤50 | >10000 |

Note:
Compounds 1-2 are tested by method 1, Compound 3-5, 7-10 are tested by method 2

2. HDAC-1 and HDAC-6 Assays:
    Method 1: The inhibitory effect of compounds on HDAC-1 and HDAC-6 function was determined in vitro using an optimized homogenous assay performed in 384-well plate format. In this assay, recombinant, full-length HDAC-1 or HDAC-6 protein (BPS Biosciences) was incubated with Ac-peptide-AMC with concentration in Km plot. Reactions were performed in Tris-based assay buffer and followed for fluorogenic release of 7-amino-4-methylcoumarin from substrate upon deacetylase and trypsin enzymatic activity. Fluorescence measurements were obtained using a multilabel plate reader (Synergy MX with excitation at 355 nm and emission at 460 nm.). Data were analyzed on a plate-by-plate basis for the linear range of fluorescence over time. Fit the data in GraphPad Prism V5.0 software to obtain ICso values using equation (Y=Bottom+(Top−Bottom)/(1+10^((Log IC$_{50}$−X)*Hill Slope), Y is % inhibition and X is compound concentration).

The testing results of the representative compounds are listed in Table 1 below.

Method 2: The inhibitory effect of compounds on HDAC-1 and HDAC-6 function was determined in vitro using an optimized homogenous assay performed in 384-well plate format. In this assay, recombinant, full-length HDAC-1 (Active Motif) and HDAC-6 protein (BPS Biosciences) was incubated with Ac-peptide-AMC with concentration in Km plot. Reactions were performed in Tris-based assay buffer and followed for fluorogenic release of 7-amino-4-methylcoumarin from substrate upon deacetylase and trypsin enzymatic activity. Fluorescence measurements were obtained using a multilabel plate reader (Synergy with excitation at 355 nm and emission at 460 nm.). Data were analyzed on a plate-by-plate basis for the linear range of fluorescence over time. Fit the data in GraphPad Prism V5.0 software to obtain IC$_{50}$ values using equation (Y=Bottom+(Top−Bottom)/(1+10^((Log IC$_{50}$−X)*Hill Slope), Y is % inhibition and X is compound concentration).

The testing results of the representative compounds are listed in Table 2 below.

TABLE 2

HDAC-1 and HDAC-6 assays ($IC_{50}$, nM)

| Compounds | HDAC-1 | HDAC-6 |
|---|---|---|
| 1 | >5 and ≤10 | >10 and ≤50 |
| 2 | >10 and ≤50 | >50 and ≤75 |
| 3 | >50 and ≤75 | >75 and ≤100 |
| 5 | ≤5 | >5 and ≤10 |
| 9 | >5 and ≤10 | >10 and ≤50 |
| 10 | ≤5 | >10 and ≤50 |

Note:
Compounds 1-2 were tested using method 1, Compound 3, 5, 9 and 10 were tested using method 2. The result shows that unlike compounds bearing similar structure selectively inhibiting HD AC-6 in the current art, the compounds of this invention exhibit better inhibitory activity against HDAC-1 than HDAC-6, and are selective HDAC-1 inhibitors, thus they might have application potential for treating diseases related to HDAC-1 activity or expression.

Other Embodiments of the Invention

The present invention has been described above with reference to specific examples and embodiments, but is not constructed in any way to limit the scope of the present invention. It should be understood that various modifications and additions can be made to the disclosed specific examples and embodiments without departing from the spirit of the present invention, and such modifications and additions are considered part of the present invention.

The invention claimed is:
1. A compound selected from the group consisting of:

1

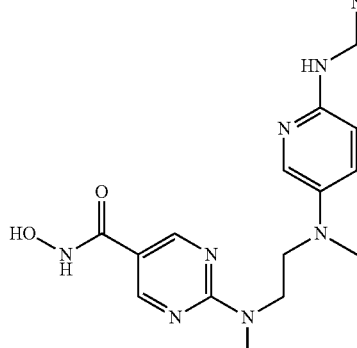

2

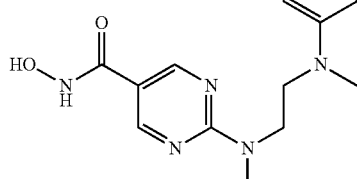

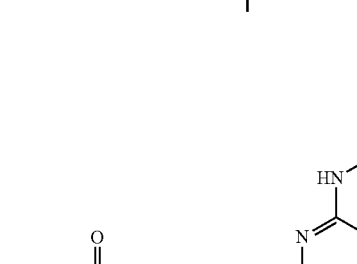

3

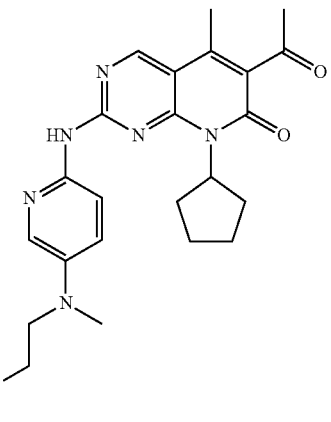

4

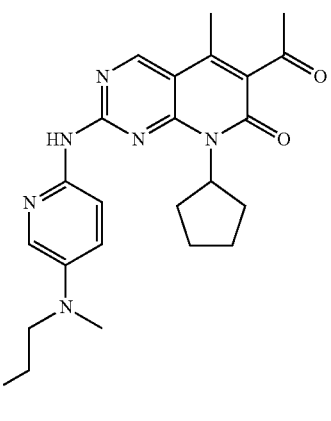

5

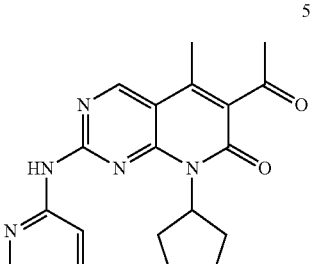

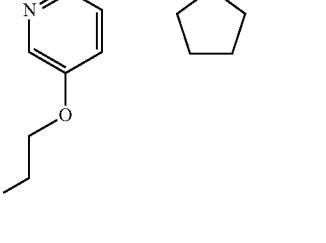

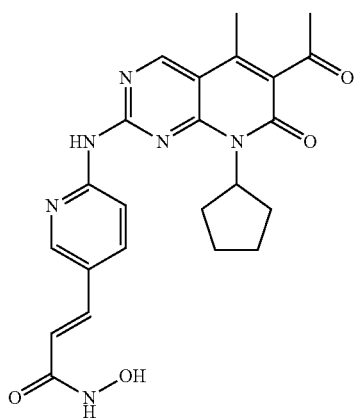
6
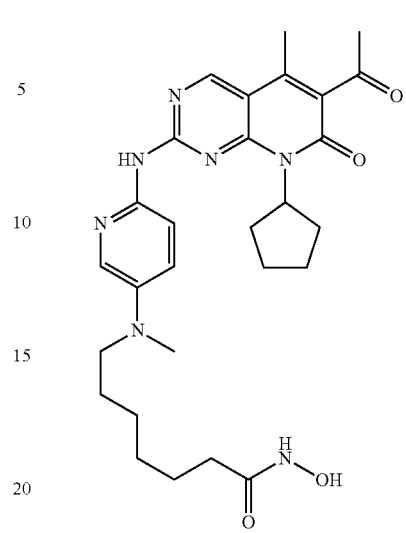
9
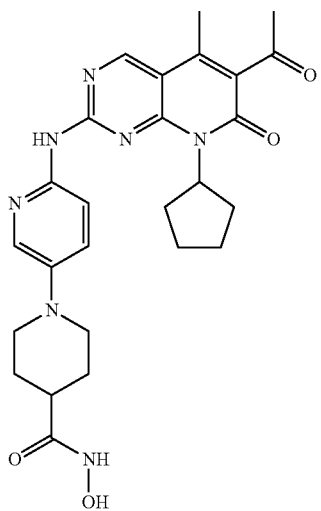
7
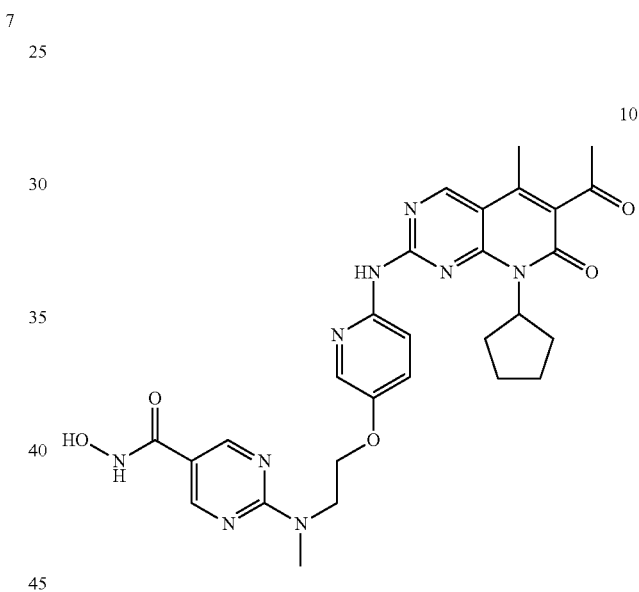
10
8
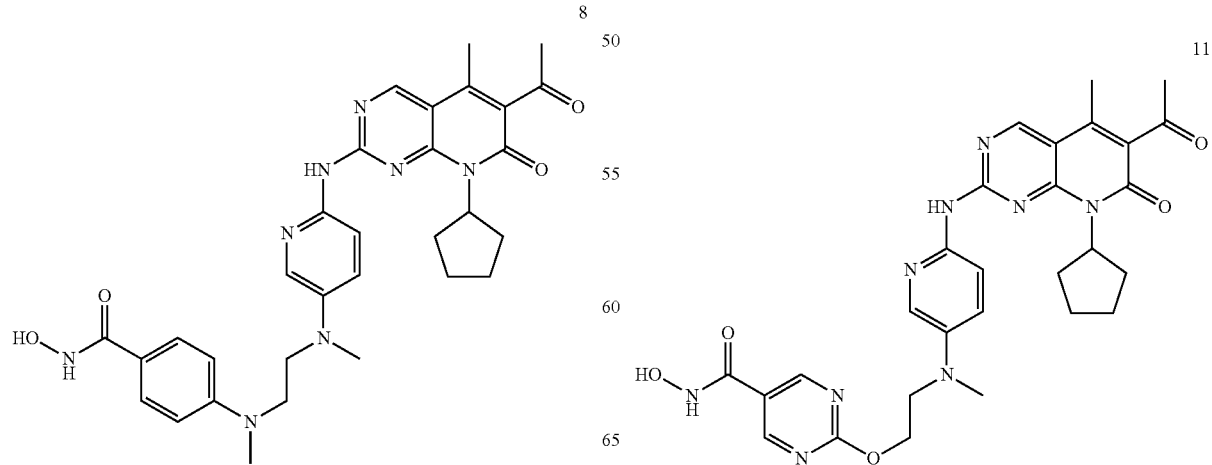
11

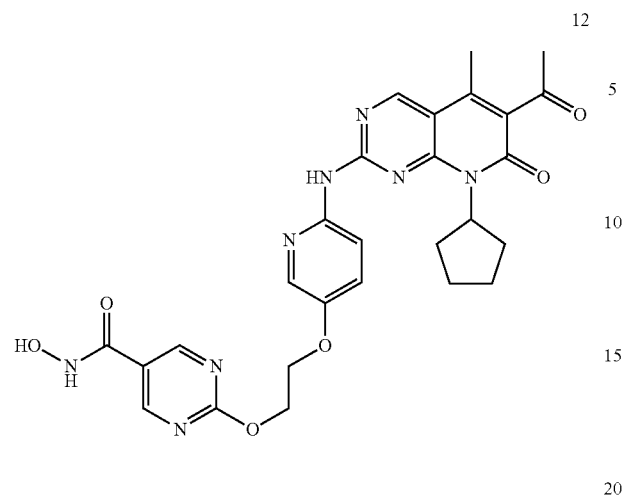
12
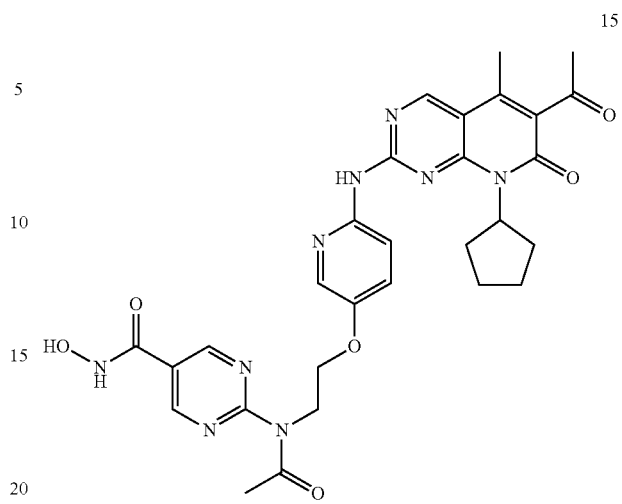
15
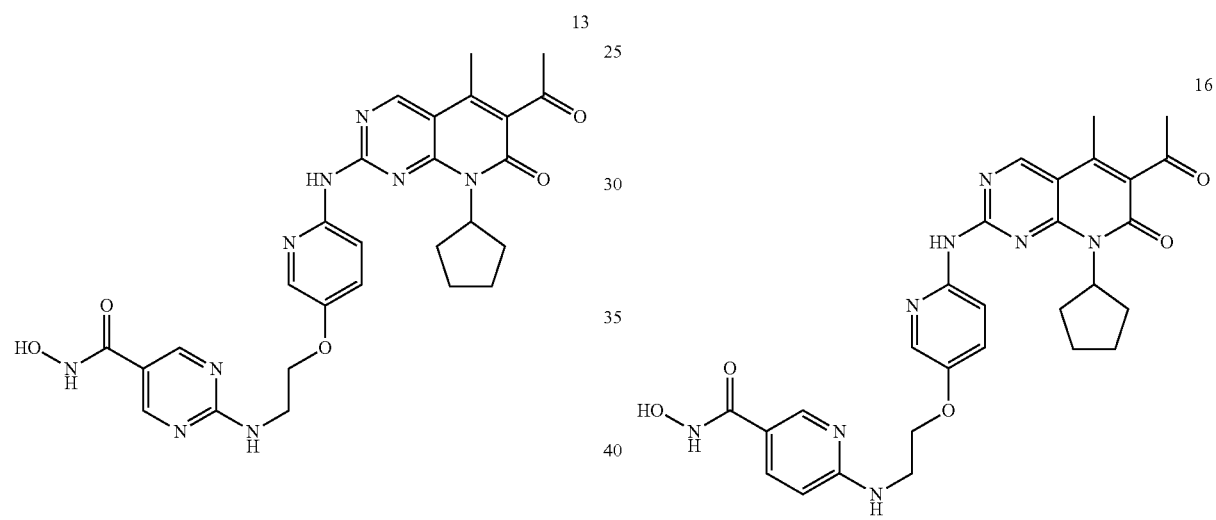
13
16
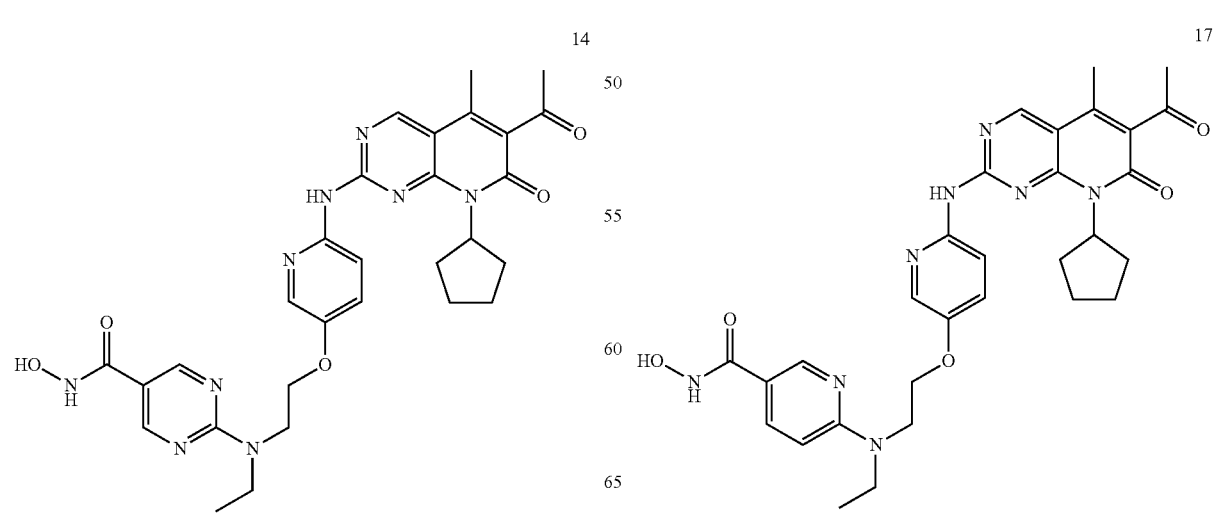
14
17

18
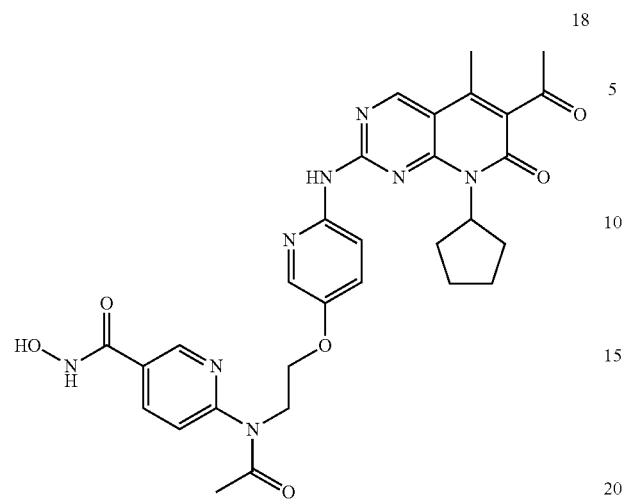
21
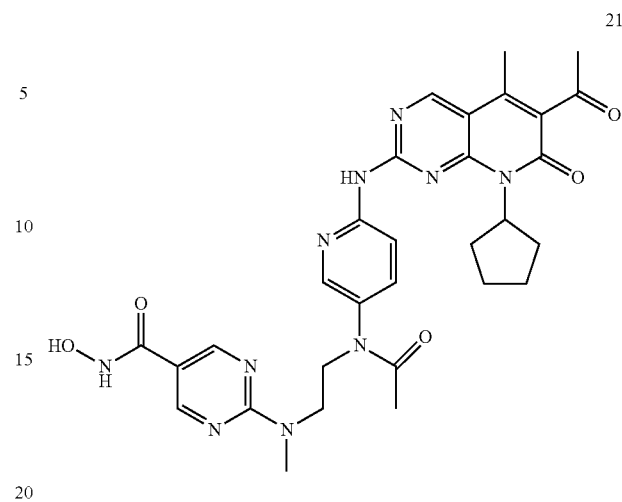
19
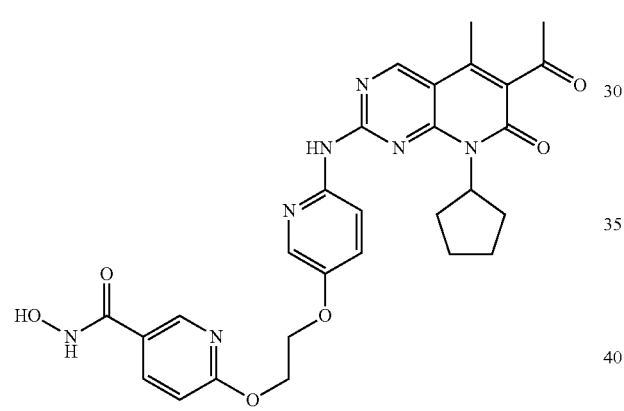
22
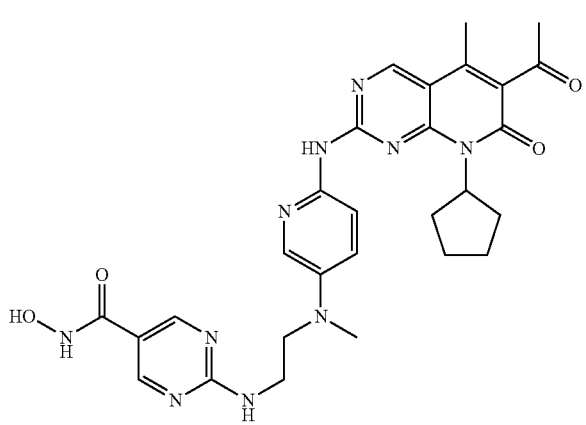
20
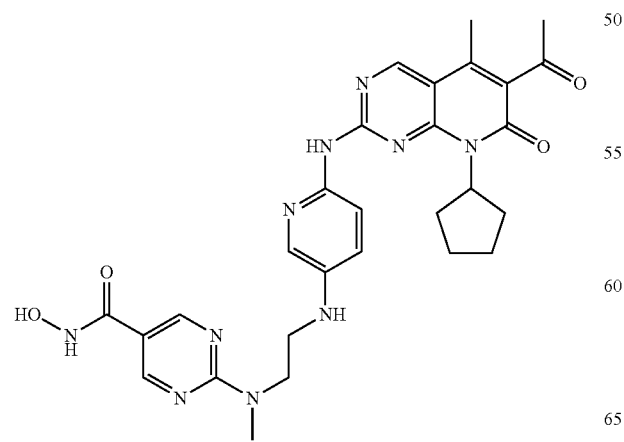
23
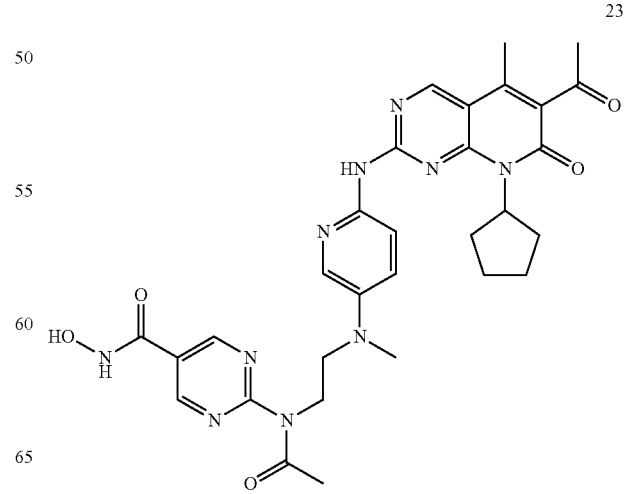

-continued

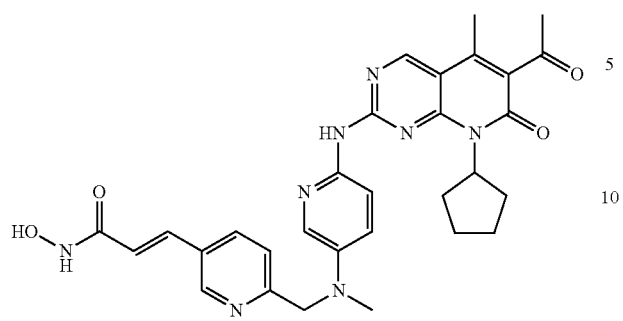

24

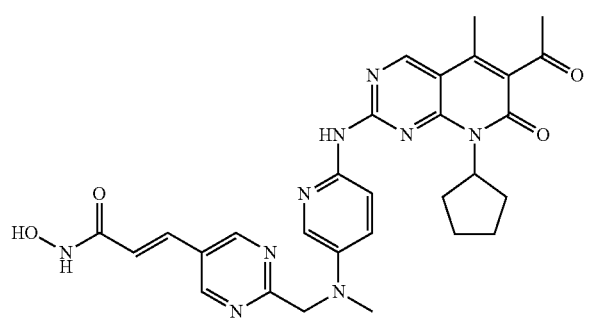

25

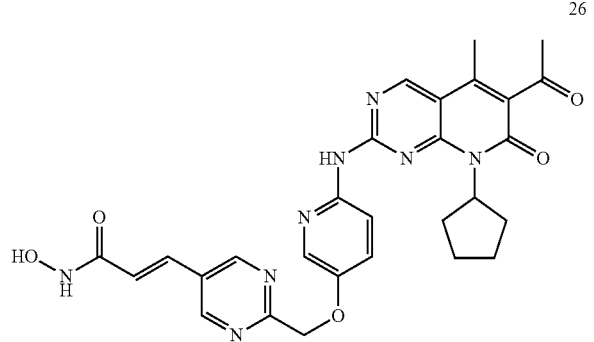

26

-continued

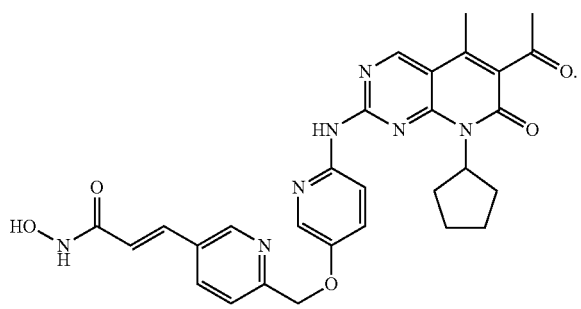

27 and

2. A pharmaceutical composition comprising the compound of claim 1, and pharmaceutically acceptable carriers or excipients.

3. A method for treating or preventing a disease or disorder mediated by cyclin-dependent kinases or histone deacetylases in a subject in need thereof, the method comprising administering to the subject the compound of claim 1.

4. The method according to claim 3, wherein the disease or disorder is selected from the group consisting of breast cancer, lymphoma, leukemia, lung cancer, ovarian cancer, liver cancer, melanoma, colon cancer, rectal cancer, kidney cells cancer, small bowel cancer, esophageal cancer, bladder cancer, prostate cancer, and pharyngeal cancer.

* * * * *